(12) United States Patent
Han et al.

(10) Patent No.: US 11,858,911 B2
(45) Date of Patent: Jan. 2, 2024

(54) SQUARYLIUM COMPOUNDS AND INFRARED CUT FILMS, INFRARED CUT FILTERS AND ELECTRONIC DEVICES INCLUDING THE SAME

(71) Applicant: Samsung Electronics Co., Ltd., Suwon-si (KR)

(72) Inventors: Moon Gyu Han, Suwon-si (KR); Kyung Bae Park, Hwaseong-si (KR); Dongseon Lee, Suwon-si (KR); Yong Wan Jin, Seoul (KR); Chul Joon Heo, Busan (KR)

(73) Assignee: Samsung Electronics Co., Ltd., Gyeonggi-do (KR)

( * ) Notice: Subject to any disclaimer, the term of this patent is extended or adjusted under 35 U.S.C. 154(b) by 0 days.

(21) Appl. No.: 17/674,200

(22) Filed: Feb. 17, 2022

(65) Prior Publication Data

US 2022/0169633 A1     Jun. 2, 2022

Related U.S. Application Data

(63) Continuation of application No. 15/934,069, filed on Mar. 23, 2018, now Pat. No. 11,261,172.

(30) Foreign Application Priority Data

Mar. 31, 2017 (KR) ........................ 10-2017-0041844

(51) Int. Cl.
| C07D 401/14 | (2006.01) |
| C09B 57/00 | (2006.01) |
| G02B 5/20 | (2006.01) |
| G02B 5/22 | (2006.01) |
| C09B 23/00 | (2006.01) |
| C07C 211/54 | (2006.01) |
| C07D 401/04 | (2006.01) |
| C07D 403/04 | (2006.01) |
| C09B 23/01 | (2006.01) |
| H04N 23/57 | (2023.01) |
| H10K 85/60 | (2023.01) |
| H01L 27/146 | (2006.01) |
| H10K 39/32 | (2023.01) |

(52) U.S. Cl.
CPC .......... *C07D 401/14* (2013.01); *C07C 211/54* (2013.01); *C07D 401/04* (2013.01); *C07D 403/04* (2013.01); *C09B 23/0066* (2013.01); *C09B 57/007* (2013.01); *G02B 5/208* (2013.01); *G02B 5/223* (2013.01); *H04N 23/57* (2023.01); *H10K 85/631* (2023.02); *H10K 85/633* (2023.02); *H10K 85/636* (2023.02); *H10K 85/654* (2023.02); *H10K 85/655* (2023.02); *H10K 85/657* (2023.02); *H10K 85/6572* (2023.02); *H01L 27/14621* (2013.01); *H10K 39/32* (2023.02)

(58) Field of Classification Search
CPC .. C07D 401/14; C07D 401/04; C07D 403/04; H04N 23/57; H10K 85/654; H10K 85/636; H10K 85/633; H10K 85/631; H10K 85/655; H10K 85/657; H10K 85/6572; H10K 39/32; C07C 211/54; C09B 23/0066; C09B 57/007; C09B 57/00; G02B 5/208; G02B 5/223; H01L 27/14621
USPC ........................................................ 252/587
See application file for complete search history.

(56) References Cited

U.S. PATENT DOCUMENTS

| 4,353,971 | A | 10/1982 | Chang et al. |
| 5,380,635 | A | 1/1995 | Gomez et al. |
| 8,614,440 | B2 | 12/2013 | Sramek et al. |
| 8,642,806 | B2 | 2/2014 | Kato et al. |
| 2014/0350146 | A1 | 11/2014 | Tsubouchi |

FOREIGN PATENT DOCUMENTS

| EP | 2053618 A1 | 4/2009 |
| JP | H03-282481 A | 12/1991 |
| JP | 2009180875 A | 8/2009 |
| WO | WO-2008-023489 A1 | 2/2008 |

OTHER PUBLICATIONS

Kim et al., "Absorption spectra, aggregation and photofading behaviour of near-infrared absorbing squarylium dyes containing perimidine moiety", Dyes and Pigments, Elsevier Applied Science Publishers, vol. 55, No. 1, Oct. 1, 2002, pp. 1-7. (Year: 2002).*
Extended European Search Report dated Jun. 6, 2018 issued in corresponding European Application No. 18164034.3-1110.
Kim S-H et al., "Absorption spectra, aggregation and photofading behaviour of near-infrared absorbing squarylium dyes containing perimidine moiety", Dyes and Pigments, Elsevier Applied Science Publishers, Barking, GB, vol. 55, No. 1, Oct. 1, 2002, pp. 1-7, XP004381028, ISSN: 0143-7208, DOI: 10:1016/S0143-728(02)00051-7.
U. Santhosh, Triplet Excited-State Properties of the Monomer and Aggregate of Bis(2,4,6-trihydroxyphenyl)squaraine. J. Phys. Chem. A, vol. 104, No. 9, 2000 pp. 1842-1847.
Daniel Citterio, Dyes for use in integrated optical sensors. Sensors and Actuators B—Chemical, 38-39 (1997) 1-3, 202-206.

(Continued)

*Primary Examiner* — Ling Siu Choi
*Assistant Examiner* — Ronald Grinsted
(74) *Attorney, Agent, or Firm* — Harness, Dickey & Pierce, P.L.C.

(57) ABSTRACT

A squarylium compound has high transmittance in a visible wavelength spectrum of light and is configured to selectively absorb light in an infrared/near infrared wavelength spectrum of light.

19 Claims, 26 Drawing Sheets

(56) References Cited

OTHER PUBLICATIONS

Daniel Citterio, Development of new dyes for use in integrated optical sensors. Frensenius Journal of Analytical Chemistry, 354, 7-8, (1996), p. 836-840.
This application is a Continuation of U.S. Appl. No. 15/934,069. None of the documents listed on the attached Form PTO-SBO8a/1449 are enclosed because they were previously cited in U.S. Appl. No. 15/934,069.

* cited by examiner

SQUARYLIUM COMPOUNDS AND INFRARED CUT FILMS, INFRARED CUT FILTERS AND ELECTRONIC DEVICES INCLUDING THE SAME

CROSS-REFERENCE TO RELATED APPLICATIONS

This application is a continuation of U.S. application Ser. No. 15/934,069, filed Mar. 23, 2018, which claims priority to and the benefit of, under 35 U.S.C. § 119, Korean Patent Application No. 10-2017-0041844 filed in the Korean Intellectual Property Office on Mar. 31, 2017, the entire contents of each of which are incorporated herein by reference.

BACKGROUND

1. Field

A squarylium compound and infrared cut films, infrared cut filters, and electronic devices including the same are disclosed.

2. Description of the Related Art

A display device may display a color image based on emitting light of a combination of three primary colors of red, blue, and green. In some cases, in order to be configured to provide an image having a clear tone, a display device may include a color filter having a color correction function. Such a filter having a color correction function may be an infrared/near infrared cut filter configured to selectively transmit or cut light in a certain wavelength spectrum of light, of light passing through the filter. Such light passing through the filter may include light emitted by one or more portions of the display device.

Such infrared/near infrared cut filters have been manufactured according to various methods. For example, there is a method of depositing a metal such as silver on a surface of a transparent substrate such as glass, so that the deposited metal may reflect a near infrared ray. Another method may include adding a near infrared ray absorption dye to a transparent resin such as an acrylic resin or a polycarbonate resin.

In some cases, an infrared/near infrared cut filter manufactured by depositing a metal on a glass substrate may include foreign particles mixed therein. Such foreign particles may include, for example, glass pieces of the glass substrate.

Accordingly, there are needs for development of an absorption dye having improved near infrared ray absorption performance.

SUMMARY

Some example embodiments provide a squarylium compound having high transmittance in a visible wavelength spectrum of light and capable of selectively absorbing light in an infrared/near infrared wavelength spectrum of light.

Some example embodiments provide an infrared cut film and an infrared cut filter including the squarylium compound.

Yet some example embodiments provide an electronic device including the squarylium compound.

According to some example embodiments, a squarylium compound represented by Chemical Formula 1 is provided.

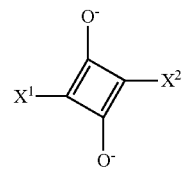

[Chemical Formula 1]

In Chemical Formula 1, $X^1$ and $X^2$ are the same or different and are each independently one of a functional group represented by Chemical Formula 1A, a functional group represented by Chemical Formula 1B, a functional group represented by Chemical Formula 1C, and a functional group represented by Chemical Formula 1D, provided that at least one of $X^1$ and $X^2$ is a functional group represented by Chemical Formula 1A or a functional group represented by Chemical Formula 1B,

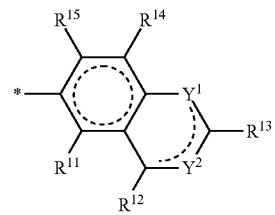

[Chemical Formula 1A]

wherein, in Chemical Formula 1A,
$Y^1$ and $Y^2$ are independently N or $NR^{16}$,
$R^{11}$ and $R^{12}$ are linked with each other to collectively comprise a fused ring with a quinazoline ring, or $R^{11}$ and $R^{12}$ are each independently one compound of a first set of compounds, the first set of compounds including hydrogen, a halogen, a cyano group, a nitro group, a hydroxyl group, a carboxyl group, an ester group, a substituted or unsubstituted C1 to C20 alkyl group, a substituted or unsubstituted C1 to C20 alkoxy group, a substituted or unsubstituted C6 to C30 aryl group, a substituted or unsubstituted C3 to C20 cycloalkyl group, a substituted or unsubstituted C3 to C20 heteroaryl group, and a substituted or unsubstituted C2 to C20 heterocycloalkyl group,
$R^{13}$ is one compound of a second set of compounds, the second set of compounds including a substituted or unsubstituted C6 to C30 aryl group, a substituted or unsubstituted C3 to C20 heteroaryl group, a substituted or unsubstituted C6 to C20 arylamine group, and a substituted or unsubstituted C3 to C30 heteroarylamine group, and
$R^{14}$ and $R^{15}$ are linked with each other to collectively comprise a fused ring with a quinazoline ring, or $R^{14}$, $R^{15}$, and $R^{16}$ are independently one compound of the first set of compounds,

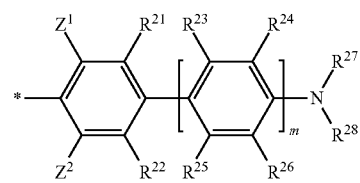

[Chemical Formula 1B]

wherein, in Chemical Formula 1B, m is 1 or 2, $Z^1$ and $Z^2$ are independently one of hydrogen or a hydroxyl group, $R^{21}$ to $R^{26}$ are independently one compound of the first set of compounds, and $R^{27}$ and $R^{28}$ are linked with each other to collectively comprise an N-containing aromatic ring group or an N-containing alicyclic cyclic group, or $R^{27}$ and $R^{28}$ are independently one compound of a third set of compounds, the third set of compounds including a substituted or unsubstituted C1 to C20 alkyl group, a substituted or unsubstituted C1 to C20 alkoxy group, a substituted or unsubstituted C6 to C30 aryl group, a substituted or unsubstituted C3 to C20 cycloalkyl group, a substituted or unsubstituted C3 to C20 heteroaryl group, and a substituted or unsubstituted C2 to C20 heterocycloalkyl group,

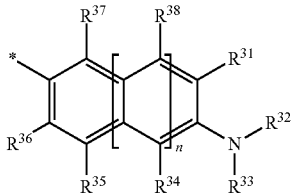

[Chemical Formula 1C]

wherein, in Chemical Formula 1C, n is 1 or 2, $R^{31}$ and $R^{32}$ are linked with each other to collectively comprise an aromatic ring group or an alicyclic cyclic group, $R^{33}$ and $R^{34}$ are linked with each other to collectively comprise an aromatic ring group or an alicyclic cyclic group, and $R^{35}$ to $R^{38}$ are independently one compound of the first set of compounds,

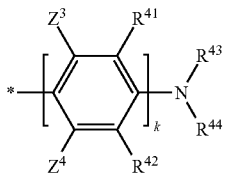

[Chemical Formula 1D]

wherein, in Chemical Formula 1 D, k is 0 or 1, $Z^3$ and $Z^4$ are independently one of hydrogen or a hydroxyl group, $R^{41}$ and $R^{42}$ are independently one compound of the first set of compounds, and $R^{43}$ and $R^{44}$ are linked with each other to collectively comprise an N-containing aromatic ring group or an N-containing alicyclic cyclic group, or $R^{43}$ and $R^{44}$ are independently one of a substituted or unsubstituted C1 to C20 alkyl group, a substituted or unsubstituted C1 to C20 alkoxy group, a substituted or unsubstituted C6 to C30 aryl group, a substituted or unsubstituted C3 to C20 cycloalkyl group, a substituted or unsubstituted C3 to C20 heteroaryl group, and a substituted or unsubstituted C2 to C20 heterocycloalkyl group.

$R^{11}$ and $R^{12}$ of Chemical Formula 1A may be linked with each other to collectively comprise a C6 or C7 aromatic ring fused with a quinazoline ring and the aromatic ring may not include a heteroatom.

The functional group represented by Chemical Formula 1A may be a functional group represented by Chemical Formula 1A-1.

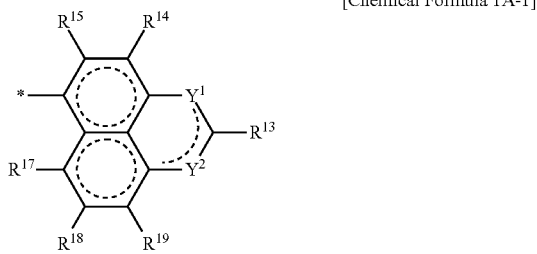

[Chemical Formula 1A-1]

In Chemical Formula 1A-1, $Y^1$ and $Y^2$ are independently N or $NR^{16}$, $R^{16}$, $R^{17}$, $R^{18}$, and $R^{19}$ are one of N or $NR^{16}$, wherein $R^{16}$ is one of hydrogen or a substituted or unsubstituted C1 to C6 alkyl group, $R^{17}$, $R^{18}$, and $R^{19}$ are independently one compound of the first set of compounds, $R^{13}$ is one compound of the second set of compounds, and $R^{14}$ and $R^{15}$ are linked with each other to collectively comprise a ring fused with a quinazoline ring, or $R^{14}$ and $R^{15}$ are independently one compound of the first set of compounds.

$R^{13}$ of Chemical Formula 1A or Chemical Formula 1A-1 may be selected from a substituted or unsubstituted phenyl group, a substituted or unsubstituted naphthyl group, a substituted or unsubstituted anthracenyl group, a substituted or unsubstituted phenanthrenyl group, a substituted or unsubstituted pyrenyl group, a substituted or unsubstituted chrysenyl group, a substituted or unsubstituted fluorenyl group, and a substituted or unsubstituted perylenyl group.

$R^{13}$ of Chemical Formula 1A or Chemical Formula 1A-1 may be selected from a substituted or unsubstituted pyridyl group, a substituted or unsubstituted pyrazinyl group, a substituted or unsubstituted pyrimidinyl group, a substituted or unsubstituted pyridazinyl group, a substituted or unsubstituted quinolyl group, a substituted or unsubstituted isoquinolyl group, a substituted or unsubstituted phthalazinyl group, a substituted or unsubstituted quinazolinyl group, a substituted or unsubstituted quinoxalinyl group, a substituted or unsubstituted naphthyridinyl group, a substituted or unsubstituted cinnolinyl group, a substituted or unsubstituted pyrrolyl group, a substituted or unsubstituted pyrazolyl group, a substituted or unsubstituted imidazolyl group, a substituted or unsubstituted triazolyl group, a substituted or unsubstituted tetrazolyl group, a substituted or unsubstituted thienyl group, a substituted or unsubstituted thiazolyl group, a substituted or unsubstituted oxazolyl group, a substituted or unsubstituted indolyl group, a substituted or unsubstituted isoindolyl group, a substituted or unsubstituted indazolyl group, a substituted or unsubstituted benzoimidazolyl group, a substituted or unsubstituted benzotriazolyl group, a substituted or unsubstituted benzothiazolyl group, a substituted or unsubstituted benzooxazolyl group, a substituted or unsubstituted carbazole group, a substituted or unsubstituted phenazinyl group, and a substituted or unsubstituted acridinyl group.

$R^{13}$ of Chemical Formula 1A or Chemical Formula 1A-1 may be one functional group of a plurality of functional groups represented by Chemical Formula 2.

[Chemical Formula 2]

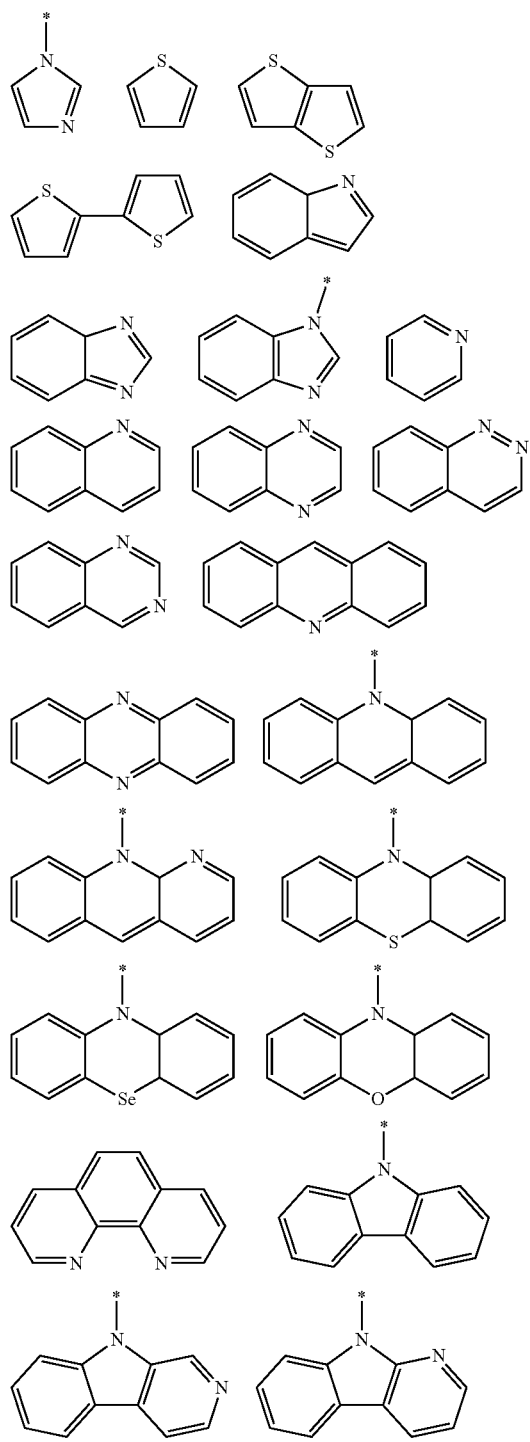

In Chemical Formula 2, hydrogen of each aromatic ring may be replaced by a substituent selected from a halogen, a cyano group, a nitro group, a hydroxyl group, a carboxyl group, an ester group, a substituted or unsubstituted C1 to C20 alkyl group, a substituted or unsubstituted C1 to C20 alkoxy group, a substituted or unsubstituted C6 to C30 aryl group, a substituted or unsubstituted C3 to C20 cycloalkyl group, a substituted or unsubstituted C3 to C20 heteroaryl group, and a substituted or unsubstituted C2 to C20 heterocycloalkyl group, and each position of a plurality of aromatic rings of the plurality of functional groups that is not indicated by an asterisk (*) is a binding position at $R^{13}$ of Chemical Formula 1A.

$R^{13}$ of Chemical Formula 1A or Chemical Formula 1A-1 may be selected from a substituted or unsubstituted pyrrolidinyl group, a substituted or unsubstituted piperidinyl group, a substituted or unsubstituted piperazinyl group, a substituted or unsubstituted morpholinyl group, a substituted or unsubstituted thiomorpholinyl group, a substituted or unsubstituted tetrahydropyridyl group, a substituted or unsubstituted tetrahydroquinolinyl group, a substituted or unsubstituted tetrahydroisoquinolinyl group, a substituted or unsubstituted tetrahydrofuryl group, a substituted or unsubstituted tetrahydropyranyl group, a substituted or unsubstituted dihydrobenzofuranyl group, a substituted or unsubstituted indolinyl group, a substituted or unsubstituted isoindolinyl group, and a substituted or unsubstituted tetrahydrocarbazolyl group.

In $R^{13}$ of Chemical Formula 1A or Chemical Formula 1A-1, the substituted or unsubstituted C6 to C20 arylamine group and the substituted or unsubstituted C3 to C30 heteroarylamine group may be represented by —$NR^xR^y$ wherein $R^x$ and $R^y$ are independently selected from a substituted or unsubstituted C6 to C30 aryl group and a substituted or unsubstituted C3 to C20 heteroaryl group.

Chemical Formula 1B may be one functional group of a plurality of functional groups represented by Chemical Formula 1B-1, Chemical Formula 1B-2, and Chemical Formula 1B-3.

[Chemical Formula 1B-1]

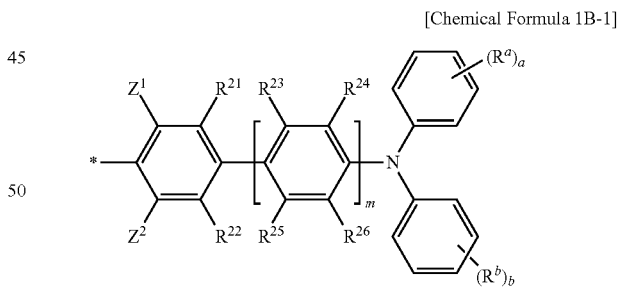

In Chemical Formula 1B-1, m is 1 or 2, $Z^1$ and $Z^2$ are independently hydrogen or a hydroxyl group, $R^{21}$ to $R^{26}$ are independently one compound of the first set of compounds, $R^a$ and $R^b$ are independently one compound of the first set of compounds, and a and b are independently an integer that is inclusively between 0 to 5.

[Chemical Formula 1B-2]

In Chemical Formula 1B-2, m is 1 or 2, $Z^1$ and $Z^2$ are independently one of hydrogen or a hydroxyl group, $R^{21}$ to $R^{26}$ are independently one compound of the first set of compounds, $R^a$ and $R^b$ are independently one compound of the first set of compounds, and a and b are independently an integer that is inclusively between 0 to 4.

[Chemical Formula 1B-3]

In Chemical Formula 1B-3, m is 1 or 2, $Z^1$ and $Z^2$ are independently one of hydrogen or a hydroxyl group, $R^{21}$ to $R^{26}$ are independently one compound of the first set of compounds, $R^a$ and $R^b$ are independently one compound of the first set of compounds, Y is selected from ("one of") $NR^c$, O, S, Se, and Te (wherein $R^c$ is selected from hydrogen and a substituted or unsubstituted C1 to C6 alkyl group), and a and b are independently an integer that is inclusively between 0 to 4.

Chemical Formula 10 may be selected from functional groups represented by Chemical Formulae 10-1 and 10-2.

[Chemical Formula 1C-1]

[Chemical Formula 1C-2]

In Chemical Formula 1C-1 and Chemical Formula 1C-2, $R^a$, $R^b$, $R^c$, and $R^d$ are independently one compound of the first set of compounds, a and b are independently an integer that is inclusively between 0 to 6, c is an integer that is inclusively between 0 to 2, and e is an integer that is inclusively between 0 to 3.

Chemical Formula 1D may be one functional group of a plurality of functional groups represented by Chemical Formula 1 D-1, Chemical Formula 1D-2, and Chemical Formula 1D-3.

[Chemical Formula 1D-1]

In Chemical Formula 1D-1, k is 0 or 1, $Z^3$ and $Z^4$ are independently one of hydrogen or a hydroxyl group, $R^{41}$ and $R^{42}$ are independently one compound of the first set of compounds, $R^a$ and $R^b$ are independently one compound of the first set of compounds, and a and b are independently an integer that is inclusively between 0 to 5.

[Chemical Formula 1D-2]

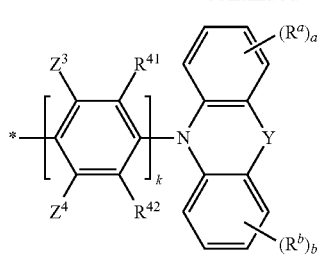

[Chemical Formula 1D-3]

In Chemical Formula 1D-2 and Chemical Formula 1D-3,
k is 0 or 1,
$Z^3$ and $Z^4$ are independently one of hydrogen or a hydroxyl group, $R^{41}$ and $R^{42}$ are independently one compound of the first set of compounds, $R^a$ and $R^b$ are independently one compound of the first set of compounds, Y is one of $NR^c$, O, S, Se, and Te (wherein $R^c$ is selected from hydrogen and a substituted or unsubstituted C1 to C6 alkyl group), and a and b are independently an integer that is inclusively between 0 to 4.

The squarylium compound may be a particular compound represented by one chemical formula of Chemical Formula 4-1, Chemical Formula 4-2, Chemical Formula 4-3, Chemical Formula 4-4, Chemical Formula 4-5, Chemical Formula 4-6, Chemical Formula 4-7, Chemical Formula 4-8, Chemical Formula 4-9, and Chemical Formula 4-10.

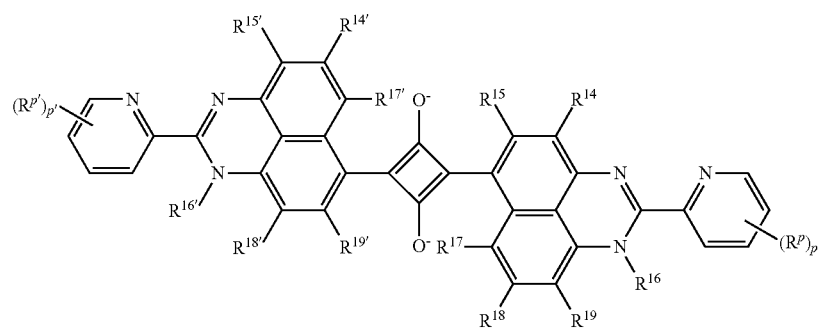

[Chemical Formula 4-1]

In Chemical Formula 4-1,
$R^{14}$, $R^{15}$, $R^{16}$, $R^{17}$, $R^{18}$, $R^{19}$, $R^{14'}$, $R^{15'}$, $R^{16'}$, $R^{17'}$, $R^{18'}$, $R^{19'}$, $R^p$, and $R^{p'}$ are independently one compound of the first set of compounds, and p and p' are independently an integer that is inclusively between 0 to 4.

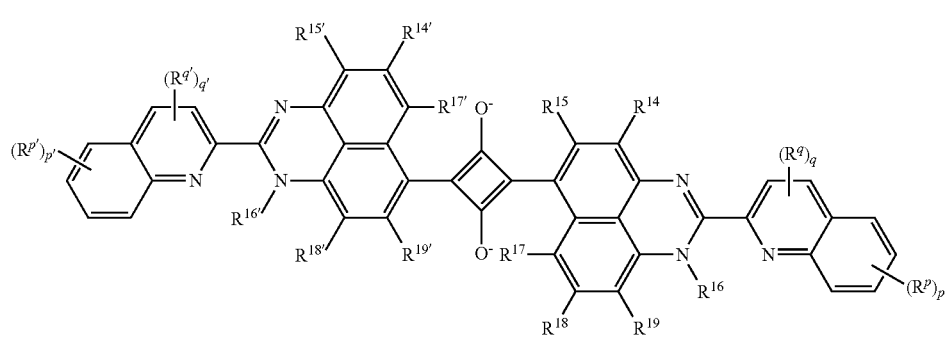

[Chemical Formula 4-2]

In Chemical Formula 4-2,
$R^{14}$, $R^{15}$, $R^{16}$, $R^{17}$, $R^{18}$, $R^{19}$, $R^{14'}$, $R^{15'}$, $R^{16'}$, $R^{17'}$, $R^{18'}$, $R^{19'}$, $R^p$, $R^{p'}$, $R^q$, and $R^{q'}$ are independently one compound of the first set of compounds, p and p' are independently an integer that is inclusively between 0 to 4, and q and q' are independently an integer that is inclusively between 0 to 2.

[Chemical Formula 4-3]

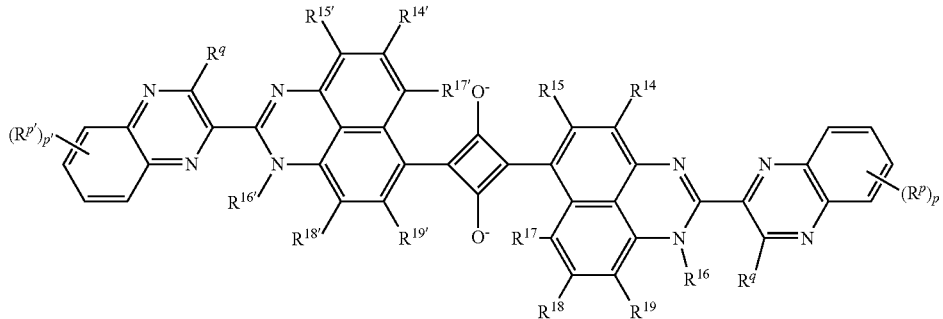

In Chemical Formula 4-3,
$R^{14}$, $R^{15}$, $R^{16}$, $R^{17}$, $R^{18}$, $R^{19}$, $R^{14'}$, $R^{15'}$, $R^{16'}$, $R^{17'}$, $R^{18'}$, $R^{19'}$, $R^p$, $R^{p'}$, $R^q$, and $R^{q'}$ are independently one compound of the first set of compounds, and p and p' are independently an integer that is inclusively between 0 to 4.

[Chemical Formula 4-4]

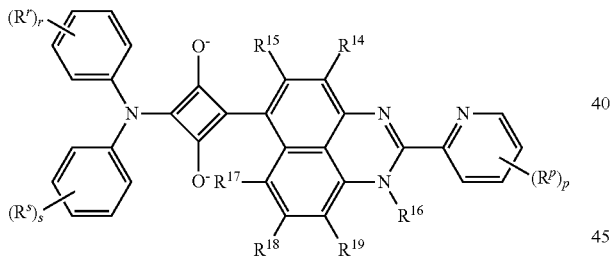

In Chemical Formula 4-4,
$R^{14}$, $R^{15}$, $R^{16}$, $R^{17}$, $R^{18}$, $R^{19}$, $R^p$, $R^r$, and $R^s$ are independently one compound of the first set of compounds, p is an integer that is inclusively between 0 to 4, and r and s are independently an integer that is inclusively between 0 to 5.

[Chemical Formula 4-5]

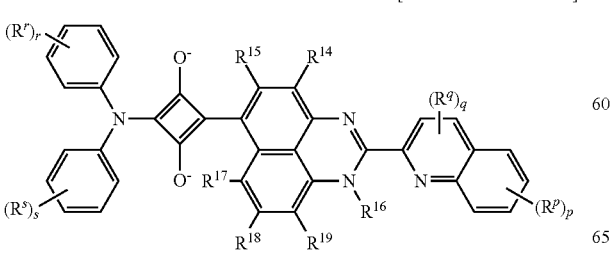

In Chemical Formula 4-5,
$R^{14}$, $R^{15}$, $R^{16}$, $R^{17}$, $R^{18}$, $R^{19}$, $R^p$, $R^q$, $R^r$, and $R^s$ are independently one compound of the first set of compounds, p is an integer that is inclusively between 0 to 4, q is an integer that is inclusively between 0 to 2, and r and s are independently an integer that is inclusively between 0 to 5.

[Chemical Formula 4-6]

In Chemical Formula 4-6,
$R^{14}$, $R^{15}$, $R^{16}$, $R^{17}$, $R^{18}$, $R^{19}$, $R^p$, $R^q$, $R^r$, and $R^s$ are independently one compound of the first set of compounds, p is an integer that is inclusively between 0 to 4, q is an integer that is inclusively between 0 to 2, and r and s are independently an integer that is inclusively between 0 to 5.

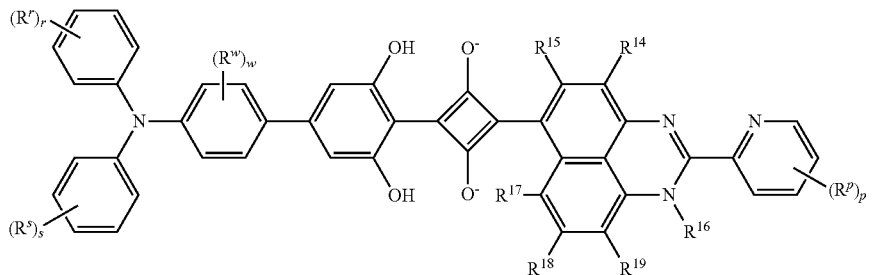

[Chemical Formula 4-7]

In Chemical Formula 4-7,
$R^{14}$, $R^{15}$, $R^{16}$, $R^{17}$, $R^{18}$, $R^{19}$, $R^p$, $R^q$, $R^r$, $R^s$, and $R^w$ are independently one compound of the first set of compounds, p and w are independently an integer that is inclusively between 0 to 4, and r and s are independently an integer that is inclusively between 0 to 5.

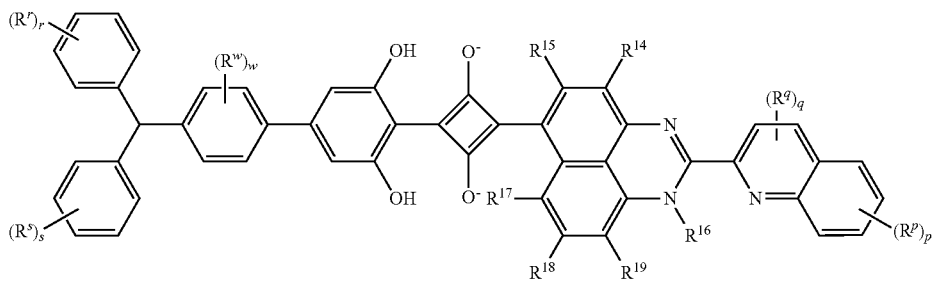

[Chemical Formula 4-8]

In Chemical Formula 4-8,
$R^{14}$, $R^{15}$, $R^{16}$, $R^{17}$, $R^{18}$, $R^{19}$, $R^p$, $R^q$, $R^r$, $R^s$, and $R^w$ are independently one compound of the first set of compounds, p and w are independently an integer that is inclusively between 0 to 4, q is an integer that is inclusively between 0 to 2, and r and s are independently an integer that is inclusively between 0 to 5.

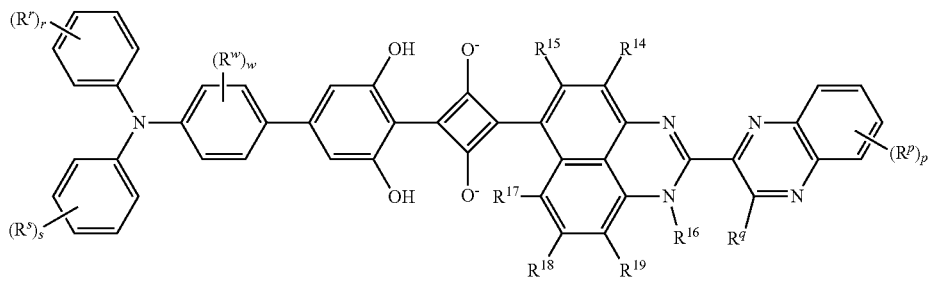

[Chemical Formula 4-9]

In Chemical Formula 4-9,
R$^{14}$, R$^{15}$, R$^{16}$, R$^{17}$, R$^{18}$, R$^{19}$, R$^p$, R$^q$, R$^r$, R$^s$, and R$^w$ are independently one compound of the first set of compounds, p and w are independently an integer that is inclusively between 0 to 4, and r and s are independently an integer that is inclusively between 0 to 5.

[Chemical Formula 4-10]

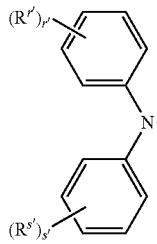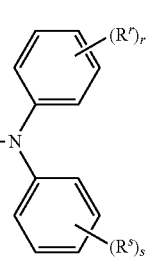

In Chemical Formula 4-10,
R$^r$, R$^s$, R$^w$, R$^{s'}$, and R$^{w'}$ are independently one compound of the first set of compounds, w and w' are independently an integer that is inclusively between 0 to 4, and r, s, r', and s' are independently an integer that is inclusively between 0 to 5.

The squarylium compound may be configured to have a maximum absorption wavelength ($\lambda_{max}$) in a range of greater than or equal to about 700 nm and less than or equal to about 1300 nm based on the squarylium compound being in a thin film state.

The squarylium compound may have a full width at half maximum (FWHM) of at least about 50 nm and less than or equal to about 150 nm based on the squarylium compound being in a thin film state.

The squarylium compound may be associated with a maximum absorption coefficient in an infrared ray (IR) wavelength spectrum of light ($A_{NIR}$) and a maximum absorption coefficient in a visible wavelength spectrum of light ($A_{VIS}$) that satisfy Relationship Equation 1

$$A_{NIR}/A_{VIS} \geq 8 \quad \text{[Relationship Equation 1]}$$

A ratio ($A_{NIR}/A_{VIS}$) of the absorption coefficients may be in a range of about 10 to about 550.

Some example embodiments provide an infrared cut film including the squarylium compound.

Some example embodiments provide the infrared cut film and an infrared light reflection layer on at least one surface of the infrared cut film.

The infrared light reflection layer may include an inorganic particulate, and may be a multi-layered thin film including a first deposition film of an inorganic particulate that is at least one particulate of titania (TiO$_2$), zirconia, and a combination thereof and a second deposition film of an inorganic particulate that is at least one particulate of silica (SiO$_2$), alumina, and a combination thereof.

A thickness of the infrared cut film may be in a range of about 50 μm to about 200 μm.

Some example embodiments provide an electronic device including the squarylium compound.

Some example embodiments provide an electronic device including the infrared cut film.

The electronic device may be an image sensor including a first photo-sensing device configured to sense light in a blue wavelength spectrum of light, a second photo-sensing device configured to sense light in a red wavelength spectrum of light, a third photo-sensing device configured to sense light in a green wavelength spectrum of light, and a fourth photo-sensing device configured to sense light in an infrared/near infrared wavelength spectrum of light, wherein the fourth photo-sensing device includes the squarylium compound.

The fourth photo-sensing device may be disposed on the first photo-sensing device, the second photo-sensing device, and the third photo-sensing device, wherein at least two of the first photo-sensing device, the second photo-sensing device, and the third photo-sensing device may be stacked.

The first photo-sensing device and the second photo-sensing device may extend in parallel to each other, the third photo-sensing device may be disposed on the first photo-sensing device and the second photo-sensing device, and the fourth photo-sensing device may be disposed on the third photo-sensing device.

The image sensor may include a blue filter configured to selectively absorb light in a blue wavelength spectrum of light on the first photo-sensing device, a red filter configured to selectively absorb light in a blue wavelength spectrum of light on the second photo-sensing device, a green filter configured to selectively absorb light in a blue wavelength spectrum of light on the third photo-sensing device, and an infrared cut filter configured to selectively absorb light in an infrared/near infrared wavelength spectrum of light on the fourth photo-sensing device.

The infrared cut filter may be on the blue filter, the red filter, and the green filter.

The squarylium compound may have (e.g., may be associated with) low absorbance in a visible wavelength spectrum of light and high absorbance in an infrared/near infrared wavelength spectrum of light, and thus may be configured to have improved spectral sensitivity at low illumination and may be applied to various electronic devices to thus improve spectral sensitivity thereof in low illumination environments.

DETAILED DESCRIPTION

Figure 1:
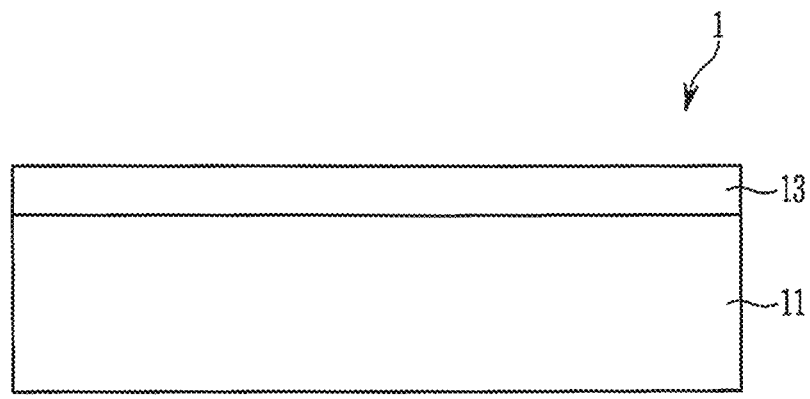
FIG. 1 is a schematic cross-sectional view of an infrared cut filter according to some example embodiments.

Hereinafter, example embodiments will be described in detail, and may be easily performed by a person having an ordinary skill in the related art. However, this disclosure may be embodied in many different forms and is not construed as limited to the example embodiments set forth herein.

It should be understood that, although the terms first, second, third, etc. may be used herein to describe various elements, components, regions, layers and/or sections, these elements, components, regions, layers, and/or sections should not be limited by these terms. These terms are only used to distinguish one element, component, region, layer, or section from another region, layer, or section. Thus, a first element, component, region, layer, or section discussed below could be termed a second element, component, region, layer, or section without departing from the teachings of example embodiments.

Spatially relative terms (e.g., "beneath," "below," "lower," "above," "upper," and the like) may be used herein for ease of description to describe one element or feature's relationship to another element(s) or feature(s) as illustrated in the figures. It should be understood that the spatially relative terms are intended to encompass different orientations of the device in use or operation in addition to the orientation depicted in the figures. For example, if the device in the figures is turned over, elements described as "below" or "beneath" other elements or features would then be oriented "above" the other elements or features. Thus, the term "below" may encompass both an orientation of above and below. The device may be otherwise oriented (rotated 90 degrees or at other orientations) and the spatially relative descriptors used herein interpreted accordingly.

The terminology used herein is for the purpose of describing various embodiments only and is not intended to be limiting of example embodiments. As used herein, the singular forms "a," "an," and "the" are intended to include the plural forms as well, unless the context clearly indicates otherwise. It will be further understood that the terms "includes," "including," "comprises," and/or "comprising," when used in this specification, specify the presence of stated features, integers, steps, operations, elements, and/or components, but do not preclude the presence or addition of one or more other features, integers, steps, operations, elements, components, and/or groups thereof.

Example embodiments are described herein with reference to cross-sectional illustrations that are schematic illustrations of idealized embodiments (and intermediate structures) of example embodiments. As such, variations from the shapes of the illustrations as a result, for example, of manufacturing techniques and/or tolerances, are to be expected. Thus, example embodiments should not be construed as limited to the shapes of regions illustrated herein but are to include deviations in shapes that result, for example, from manufacturing.

Unless otherwise defined, all terms (including technical and scientific terms) used herein have the same meaning as commonly understood by one of ordinary skill in the art to which example embodiments belong. It will be further understood that terms, including those defined in commonly used dictionaries, should be interpreted as having a meaning that is consistent with their meaning in the context of the relevant art and will not be interpreted in an idealized or overly formal sense unless expressly so defined herein.

As used herein, when a definition is not otherwise provided, "infrared light" refers to "near infrared light (NIR)" in a region of about 700 nm to about 1400 nm.

When the terms "about" or "substantially" are used in this specification in connection with a numerical value, it is intended that the associated numerical value include a tolerance of ±10% around the stated numerical value. When ranges are specified, the range includes all values therebetween such as increments of 0.1%.

As used herein, when a definition is not otherwise provided, "substituted" refers to replacement of hydrogen of a compound or a functional group by a substituent selected from a halogen (F, Br, Cl, or I), a hydroxy group, a nitro group, a cyano group, an amino group, an azido group, an amidino group, a hydrazino group, a hydrazono group, a carbonyl group, a carbamyl group, a thiol group, an ester group, a carboxyl group or a salt thereof, a sulfonic acid group or a salt thereof, a phosphoric acid or a salt thereof, a C1 to C20 alkyl group, for example a C1 to C10 alkyl group, a C1 to C20 alkoxy group, for example a C1 to C10 alkoxy group, a C2 to C20 alkenyl group, a C2 to C20 alkynyl group, a C6 to C30 aryl group, a C7 to C30 arylalkyl group, a C3 to C20 heteroaryl group, a C3 to C20 heteroarylalkyl group, a C3 to C30 cycloalkyl group, a C3 to C15 cycloalkenyl group, a C6 to C15 cycloalkynyl group, a C2 to C20 heterocycloalkyl group, and a combination thereof.

In addition, "substituted" in an aromatic ring group refers to replacement of —$CH_2$— in the ring by —NR— (wherein R is selected from hydrogen, a halogen, a C1 to C10 alkyl group, a C1 to C10 alkoxy group, a C6 to C30 aryl group, and a C3 to C20 heteroaryl group), —O—, —S—, or —Se— or replacement of —CH= in the ring by —N=.

As used herein, when a definition is not otherwise provided, "hetero" refers to inclusion of one to three heteroatoms selected from N, O, S, P, and Si.

As used herein, when a definition is not otherwise provided, "halogen" refers to F, Br, Cl, or I.

Singular terms in the present disclosure may include a plurality of objects unless one object is precisely indicated.

All numerical ranges of the present disclosure include all numbers and ranges within set forth numerical ranges. In addition, numerical ranges and parameters indicating a broad scope of this disclosure are approximate values but the numerical values set forth in the Examples section are reported as precisely as possible. However, it should be understood that such numerical values inherently contain certain errors resulting from measuring equipment and/or a measuring technique.

According to some example embodiments, a squarylium compound represented by Chemical Formula 1 is provided.

[Chemical Formula 1]

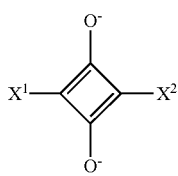

In Chemical Formula 1, $X^1$ and $X^2$ are the same or different and are independently selected from a functional group represented by Chemical Formula 1A, a functional group represented by Chemical Formula 1B, a functional group represented by Chemical Formula 1C, and a functional group represented by Chemical Formula 1D, provided that at least one of $X^1$ and $X^2$ is a functional group represented by Chemical Formula 1A or a functional group represented by Chemical Formula 1B,

[Chemical Formula 1A]

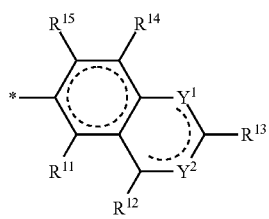

wherein, in Chemical Formula 1A, $Y^1$ and $Y^2$ are independently N or $NR^{16}$, $R^{11}$ and $R^{12}$ are independently one compound of a first set of compounds, where the first set of compounds includes hydrogen, a halogen, a cyano group, a nitro group, a hydroxyl group, a carboxyl group, an ester group, a substituted or unsubstituted C1 to C20 alkyl group, a substituted or unsubstituted C1 to C20 alkoxy group, a substituted or unsubstituted C6 to C30 aryl group, a substituted or unsubstituted C3 to C20 cycloalkyl group, a substituted or unsubstituted C3 to C20 heteroaryl group, and a substituted or unsubstituted C2 to C20 heterocycloalkyl group, or $R^{11}$ and $R^{12}$ are linked with each other to collectively comprise a fused ring with a quinazoline ring, $R^{13}$ is one compound of a second set of compounds, the second set of compounds including a substituted or unsubstituted C6 to C30 aryl group, a substituted or unsubstituted C3 to C20 heteroaryl group, a substituted or unsubstituted C6 to C20 arylamine group, and a substituted or unsubstituted C3 to C30 heteroarylamine group, and $R^{14}$, $R^{15}$, and $R^{16}$ are independently selected from ("independently one of") hydrogen, a halogen, a cyano group, a nitro group, a hydroxyl group, a carboxyl group, an ester group, a substituted or unsubstituted C1 to C20 alkyl group, a substituted or unsubstituted C1 to C20 alkoxy group, a substituted or unsubstituted C6 to C30 aryl group, a substituted or unsubstituted C3 to C20 cycloalkyl group, a substituted or unsubstituted C3 to C20 heteroaryl group, and a substituted or unsubstituted C2 to C20 heterocycloalkyl group or $R^{14}$ and $R^{15}$ are linked with each other to provide a fused ring with a quinazoline ring,

[Chemical Formula 1B]

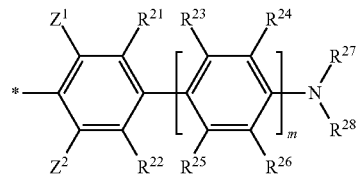

wherein, in Chemical Formula 1B, m is 1 or 2, $Z^1$ and $Z^2$ are independently hydrogen or a hydroxyl group, $R^{21}$ to $R^{26}$ are independently selected from hydrogen, a halogen, a cyano group, a nitro group, a hydroxyl group, a carboxyl group, an ester group, a substituted or unsubstituted C1 to C20 alkyl group, a substituted or unsubstituted C1 to C20 alkoxy group, a substituted or unsubstituted C6 to C30 aryl group, a substituted or unsubstituted C3 to C20 cycloalkyl group, a substituted or unsubstituted C3 to C20 heteroaryl group, and a substituted or unsubstituted C2 to C20 heterocycloalkyl group, and $R^{27}$ and $R^{28}$ are independently selected from a substituted or unsubstituted C1 to C20 alkyl group, a substituted or unsubstituted C1 to C20 alkoxy group, a substituted or unsubstituted C6 to C30 aryl group, a substituted or unsubstituted C3 to C20 cycloalkyl group, a substituted or unsubstituted C3 to C20 heteroaryl group, and a substituted or unsubstituted C2 to C20 heterocycloalkyl group or $R^{27}$ and $R^{28}$ are optionally linked with each other to provide ("collectively comprise") an N-containing aromatic ring group or an N-containing alicyclic cyclic group,

[Chemical Formula 1C]

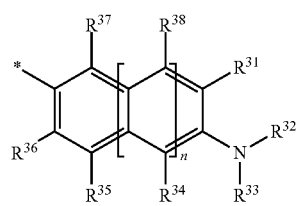

wherein, in Chemical Formula 1C, n is 1 or 2, $R^{31}$ and $R^{32}$ are linked with each other to provide an aromatic ring group or an alicyclic cyclic group, $R^{33}$ and $R^{34}$ are linked with each other to provide an aromatic ring group or an alicyclic cyclic group, and $R^{35}$ to $R^{38}$ are independently selected from hydrogen, a halogen, a cyano group, a nitro group, a hydroxyl group, a carboxyl group, an ester group, a substituted or unsubstituted C1 to C20 alkyl group, a substituted or unsubstituted C1 to C20 alkoxy group, a substituted or unsubstituted C6 to C30 aryl group, a substituted or unsubstituted C3 to C20 cycloalkyl group, a substituted or unsubstituted C3 to C20 heteroaryl group, and a substituted or unsubstituted C2 to C20 heterocycloalkyl group,

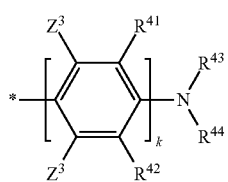
[Chemical Formula 1D]

wherein, in Chemical Formula 1 D, k is 0 or 1, $Z^3$ and $Z^4$ are independently hydrogen or a hydroxyl group, $R^{41}$ and $R^{42}$ are independently selected from hydrogen, a halogen, a cyano group, a nitro group, a hydroxyl group, a carboxyl group, an ester group, a substituted or unsubstituted C1 to C20 alkyl group, a substituted or unsubstituted C1 to C20 alkoxy group, a substituted or unsubstituted C6 to C30 aryl group, a substituted or unsubstituted C3 to C20 cycloalkyl group, a substituted or unsubstituted C3 to C20 heteroaryl group, and a substituted or unsubstituted C2 to C20 heterocycloalkyl group, and $R^{43}$ and $R^{44}$ are independently selected from a substituted or unsubstituted C1 to C20 alkyl group, a substituted or unsubstituted C1 to C20 alkoxy group, a substituted or unsubstituted C6 to C30 aryl group, a substituted or unsubstituted C3 to C20 cycloalkyl group, a substituted or unsubstituted C3 to C20 heteroaryl group, and a substituted or unsubstituted C2 to C20 heterocycloalkyl group or $R^{43}$ and $R^{44}$ are optionally linked with each other to provide an N-containing aromatic ring group or an N-containing alicyclic cyclic group.

The squarylium compound represented by Chemical Formula 1 may be a compound represented by Chemical Formula 1'.

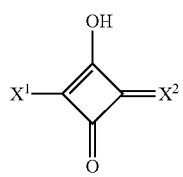
[Chemical Formula 1']

The squarylium compound represented by Chemical Formula 1 includes an electron donating group selected from the functional group represented by Chemical Formula 1A, the functional group represented by Chemical Formula 1B, the functional group represented by Chemical Formula 10, and the functional group represented by Chemical Formula 1D in the center of the squarylium nucleus and at least one of $X^1$ and $X^2$ includes the functional group represented by Chemical Formula 1A or the functional group represented by Chemical Formula 1B, and thereby the squarylium compound has excellent absorbance in an infrared/near infrared wavelength spectrum of light.

The squarylium compound may have ("be configured to have") a maximum absorption wavelength ($\lambda_{max}$) in a range of greater than or equal to about 700 nm and less than or equal to about 1300 nm, for example greater than or equal to about 710 nm and less than or equal to about 1200 nm and a full width at half maximum (FWHM) of greater than or equal to about 50 nm and less than or equal to about 150 nm, for example greater than or equal to about 50 nm and less than or equal to about 130 nm, based on the squarylium compound being in a thin film state (e.g., being included in a thin film).

The squarylium compound represented by Chemical Formula 1 has high absorbance in an infrared/near infrared wavelength spectrum of light and high transmittance in a visible ray region and thereby high selective absorbance in an infrared/near infrared wavelength spectrum of light. That is, the squarylium compound may be associated with a maximum absorption coefficient in an infrared ray (IR) wavelength spectrum of light ($A_{NIR}$) and a maximum absorption coefficient in a visible wavelength spectrum of light ($A_{VIS}$) that satisfy Relationship Equation 1.

$$A_{NIR}/A_{VIS} \geq 8$$ [Relationship Equation 1]

In Relationship Equation 1, $A_{NIR}$ is a maximum absorption coefficient in an infrared ray (IR) region and $A_{VIS}$ is a maximum absorption coefficient in a visible wavelength spectrum of light.

A ratio ($A_{NIR}/A_{VIS}$) of the maximum absorption coefficient in the infrared ray (IR) and the maximum absorption coefficient in the visible wavelength spectrum of light may be greater than or equal to about 9, for example about 10 to about 550 or about 15 to about 550. When the ratio ($A_{NIR}/A_{VIS}$) of the absorption coefficients is within the ranges, selective absorbance for light in an infrared/near infrared wavelength spectrum of light is improved.

Transmittance in a visible wavelength spectrum of light of the squarylium compound represented by Chemical Formula 1 may be greater than or equal to about 80%, for example greater than or equal to about 90%, and particularly transmittance in a blue wavelength spectrum of light of about 300 nm to about 450 nm may be greater than or equal to about 80%, for example greater than or equal to about 90%. In addition, a molar extinction coefficient in an infrared/near infrared wavelength spectrum of light may be greater than or equal to about $7 \times 10^4$ $M^{-1}$ $cm^{-1}$, for example greater than or equal to about $7.5 \times 10^4$ $M^{-1}$ $cm^{-1}$, or greater than or equal to about $8 \times 10^4$ $M^{-1}$ $cm^{-1}$. If absorbance in a blue wavelength spectrum of light of about 300 nm to about 450 nm is high despite high absorbance in an infrared ray (IR) region, efficiency may be deteriorated. From this view, the squarylium compound represented by Chemical Formula 1 has low absorbance (i.e., high transmittance) in a blue wavelength spectrum of light of about 300 nm to about 450 nm and high absorbance in an infrared ray (IR) region, and thus efficiency (e.g., external quantum efficiency) of an electronic device may be improved based on including the squarylium compound represented by Chemical Formula 1.

$R^{11}$ and $R^{12}$ represented by Chemical Formula 1A are linked with each other to provide a C6 or C7 aromatic ring that is fused with a fused ring (e.g., a quinazoline ring) of a 6-membered aromatic ring including $Y^1$ and $Y^2$ and a benzene ring and the aromatic ring may not include a heteroatom. In this case, a structure where three aromatic rings are fused structure is provided.

Chemical Formula 1A may be represented by Chemical Formula 1A-1.

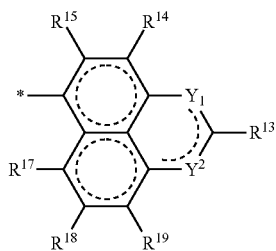

[Chemical Formula 1A-1]

In Chemical Formula 1A-1, $Y^1$ and $Y^2$ are independently N or $NR^{16}$, $R^{16}$, $R^{17}$, $R^{18}$, and $R^{19}$ are independently selected from hydrogen, a halogen, a cyano group, a nitro group, a hydroxyl group, a carboxyl group, an ester group, a substituted or unsubstituted C1 to C20 alkyl group, a substituted or unsubstituted C1 to C20 alkoxy group, a substituted or unsubstituted C6 to C30 aryl group, a substituted or unsubstituted C3 to C20 cycloalkyl group, a substituted or unsubstituted C3 to C20 heteroaryl group, and a substituted or unsubstituted C2 to C20 heterocycloalkyl group, $R^{13}$ is a substituted or unsubstituted C6 to C30 aryl group, a substituted or unsubstituted C3 to C20 heteroaryl group, a substituted or unsubstituted C6 to C20 arylamine group, and a substituted or unsubstituted C3 to C30 heteroarylamine group, and $R^{14}$ and $R^{15}$ are independently selected from hydrogen, a halogen, a cyano group, a nitro group, a hydroxyl group, a carboxyl group, an ester group, a substituted or unsubstituted C1 to C20 alkyl group, a substituted or unsubstituted C1 to C20 alkoxy group, a substituted or unsubstituted C6 to C30 aryl group, a substituted or unsubstituted C3 to C20 cycloalkyl group, a substituted or unsubstituted C3 to C20 heteroaryl group, and a substituted or unsubstituted C2 to C20 heterocycloalkyl group or $R^{14}$ and $R^{15}$ are linked with each other to provide a ring fused with a quinazoline ring.

$R^{13}$ represented by Chemical Formula 1A or Chemical Formula 1A-1 may be selected from a substituted or unsubstituted phenyl group, a substituted or unsubstituted naphthyl group, a substituted or unsubstituted anthracenyl group, a substituted or unsubstituted phenanthrenyl group, a substituted or unsubstituted pyrenyl group, a substituted or unsubstituted chrysenyl group, a substituted or unsubstituted fluorenyl group, and a substituted or unsubstituted perylenyl group.

$R^{13}$ represented by Chemical Formula 1A or Chemical Formula 1A-1 may be selected from a substituted or unsubstituted pyridyl group, a substituted or unsubstituted pyrazinyl group, a substituted or unsubstituted pyrimidinyl group, a substituted or unsubstituted pyridazinyl group, a substituted or unsubstituted quinolyl group, a substituted or unsubstituted isoquinolyl group, a substituted or unsubstituted phthalazinyl group, a substituted or unsubstituted quinazolinyl group, a substituted or unsubstituted quinoxalinyl group, a substituted or unsubstituted naphthyridinyl group, a substituted or unsubstituted cinnolinyl group, a substituted or unsubstituted pyrrolyl group, a substituted or unsubstituted pyrazolyl group, a substituted or unsubstituted imidazolyl group, a substituted or unsubstituted triazolyl group, a substituted or unsubstituted tetrazolyl group, a substituted or unsubstituted thienyl group, a substituted or unsubstituted thiazolyl group, a substituted or unsubstituted oxazolyl group, a substituted or unsubstituted indolyl group, a substituted or unsubstituted isoindolyl group, a substituted or unsubstituted indazolyl group, a substituted or unsubstituted benzoimidazolyl group, a substituted or unsubstituted benzotriazolyl group, a substituted or unsubstituted benzothiazolyl group, a substituted or unsubstituted benzooxazolyl group, a substituted or unsubstituted carbazole group, a substituted or unsubstituted phenazinyl group, and a substituted or unsubstituted acridinyl group.

$R^{13}$ represented by Chemical Formula 1A or Chemical Formula 1A-1 may be one functional group of a plurality of functional groups represented by Chemical Formula 2.

[Chemical Formula 2]

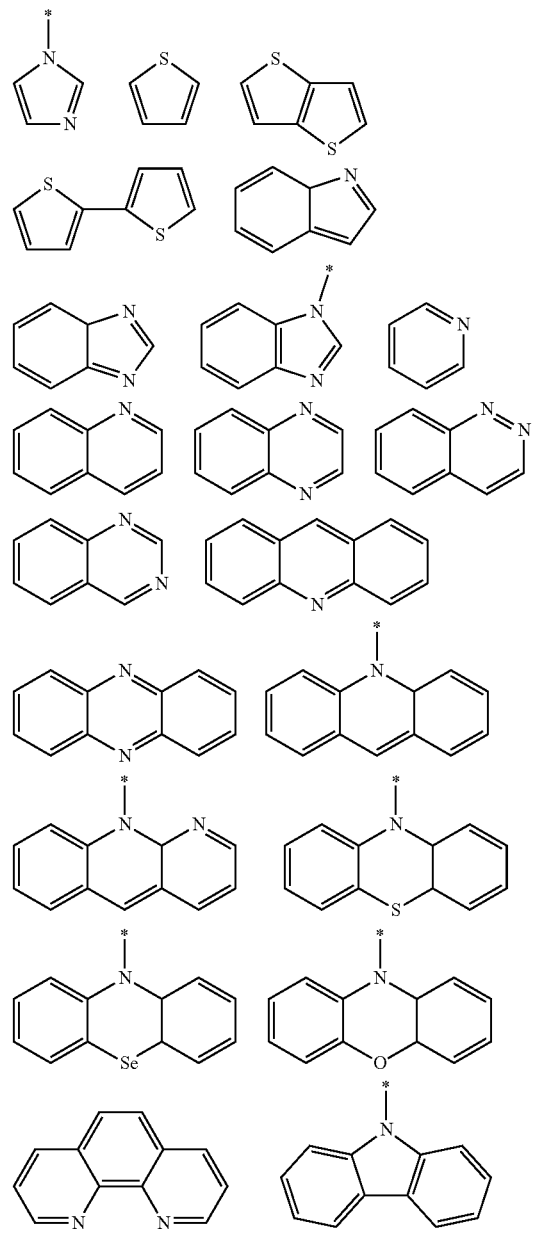

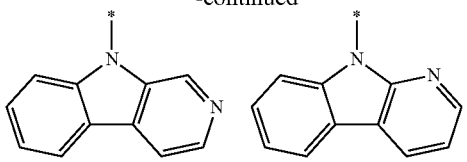

In Chemical Formula 2, hydrogen of each aromatic ring may be replaced by a substituent selected from a halogen, a cyano group, a nitro group, a hydroxyl group, a carboxyl group, an ester group, a substituted or unsubstituted C1 to C20 alkyl group, a substituted or unsubstituted C1 to C20 alkoxy group, a substituted or unsubstituted C6 to C30 aryl group, a substituted or unsubstituted C3 to C20 cycloalkyl group, a substituted or unsubstituted C3 to C20 heteroaryl group, and a substituted or unsubstituted C2 to C20 heterocycloalkyl group, and each position of a plurality of aromatic rings of the plurality of functional groups that is not indicated by an asterisk (*) may be a binding position at $R^{13}$ of Chemical Formula 1A.

$R^{13}$ represented by Chemical Formula 1A or Chemical Formula 1A-1 may be a substituted or unsubstituted pyrrolidinyl group, a substituted or unsubstituted piperidinyl group, a substituted or unsubstituted piperazinyl group, a substituted or unsubstituted morpholinyl group, a substituted or unsubstituted thiomorpholinyl group, a substituted or unsubstituted tetrahydropyridyl group, a substituted or unsubstituted tetrahydroquinolinyl group, a substituted or unsubstituted tetrahydroisoquinolinyl group, a substituted or unsubstituted tetrahydrofuryl group, a substituted or unsubstituted tetrahydropyranyl group, a substituted or unsubstituted dihydrobenzofuranyl group, a substituted or unsubstituted indolinyl group, a substituted or unsubstituted isoindolinyl group, and a substituted or unsubstituted tetrahydrocarbazolyl group which are represented by Chemical Formula 3.

[Chemical Formula 3]

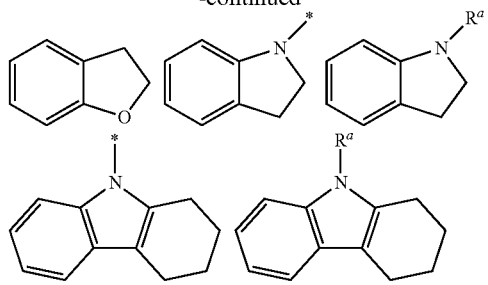

In Chemical Formula 3, $R^a$ and $R^b$ are independently selected from a halogen, a cyano group, a nitro group, a hydroxyl group, a carboxyl group, an ester group, a substituted or unsubstituted C1 to C20 alkyl group, a substituted or unsubstituted C1 to C20 alkoxy group, a substituted or unsubstituted C6 to C30 aryl group, a substituted or unsubstituted C3 to C20 cycloalkyl group, a substituted or unsubstituted C3 to C20 heteroaryl group, and a substituted or unsubstituted C2 to C20 heterocycloalkyl group, hydrogen of each aromatic ring or alicyclic ring may be replaced by a substituent selected from a halogen, a cyano group, a nitro group, a hydroxyl group, a carboxyl group, an ester group, a substituted or unsubstituted C1 to C20 alkyl group, a substituted or unsubstituted C1 to C20 alkoxy group, a substituted or unsubstituted C6 to C30 aryl group, a substituted or unsubstituted C3 to C20 cycloalkyl group, a substituted or unsubstituted C3 to C20 heteroaryl group, and a substituted or unsubstituted C2 to C20 heterocycloalkyl group, and any position of aromatic rings or alicyclic rings of functional groups that are not indicated by asterisk (*) may be a binding position at $R^{13}$ represented by Chemical Formula 1A or 1A-1.

In $R^{13}$ represented by Chemical Formula 1A or Chemical Formula 1A-1, the substituted or unsubstituted C6 to C20 arylamine group and the substituted or unsubstituted C3 to C30 heteroarylamine group may be represented by —$NR^xR^y$ wherein $R^x$ and $R^y$ are independently selected from a substituted or unsubstituted C6 to C30 aryl group and a substituted or unsubstituted C3 to C20 heteroaryl group.

In addition, the functional group represented by Chemical Formula 1B may improve selective absorbance in an infrared/near infrared wavelength spectrum of light by further including a phenylene ring in front of an amine group.

The functional group represented by Chemical Formula 1B may be one functional group of a plurality of functional groups represented by Chemical Formula 1B-1, Chemical Formula 1B-2, and Chemical Formula 1B-3.

[Chemical Formula 1B-1]

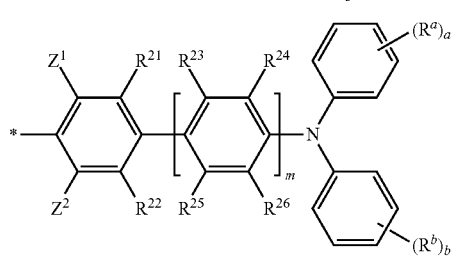

In Chemical Formula 1B-1, m is 1 or 2, $Z^1$ and $Z^2$ are independently hydrogen or a hydroxyl group, $R^{21}$ to $R^{26}$ are independently selected from hydrogen, a halogen, a cyano group, a nitro group, a hydroxyl group, a carboxyl group, an ester group, a substituted or unsubstituted C1 to C20 alkyl group, a substituted or unsubstituted C1 to C20 alkoxy group, a substituted or unsubstituted C6 to C30 aryl group, a substituted or unsubstituted C3 to C20 cycloalkyl group, a substituted or unsubstituted C3 to C20 heteroaryl group, and a substituted or unsubstituted C2 to C20 heterocycloalkyl group, $R^a$ and $R^b$ are independently selected from hydrogen, a halogen, a cyano group, a nitro group, a hydroxyl group, a carboxyl group, an ester group, a substituted or unsubstituted C1 to C20 alkyl group, a substituted or unsubstituted C1 to C20 alkoxy group, a substituted or unsubstituted C6 to C30 aryl group, a substituted or unsubstituted C3 to C20 cycloalkyl group, a substituted or unsubstituted C3 to C20 heteroaryl group, and a substituted or unsubstituted C2 to C20 heterocycloalkyl group, and a and b are independently an integer that is inclusively between 0 to 5.

[Chemical Formula 1B-2]

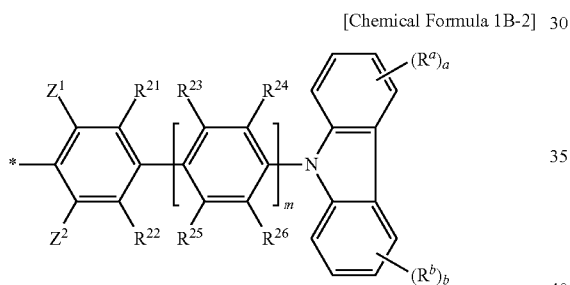

In Chemical Formula 1B-2, m is 1 or 2, $Z^1$ and $Z^2$ are independently hydrogen or a hydroxyl group, $R^{21}$ to $R^{26}$ are independently selected from hydrogen, a halogen, a cyano group, a nitro group, a hydroxyl group, a carboxyl group, an ester group, a substituted or unsubstituted C1 to C20 alkyl group, a substituted or unsubstituted C1 to C20 alkoxy group, a substituted or unsubstituted C6 to C30 aryl group, a substituted or unsubstituted C3 to C20 cycloalkyl group, a substituted or unsubstituted C3 to C20 heteroaryl group, and a substituted or unsubstituted C2 to C20 heterocycloalkyl group, $R^a$ and $R^b$ are independently selected from hydrogen, a halogen, a cyano group, a nitro group, a hydroxyl group, a carboxyl group, an ester group, a substituted or unsubstituted C1 to C20 alkyl group, a substituted or unsubstituted C1 to C20 alkoxy group, a substituted or unsubstituted C6 to C30 aryl group, a substituted or unsubstituted C3 to C20 cycloalkyl group, a substituted or unsubstituted C3 to C20 heteroaryl group, and a substituted or unsubstituted C2 to C20 heterocycloalkyl group, and a and b are independently an integer that is inclusively between 0 to 4.

[Chemical Formula 1B-3]

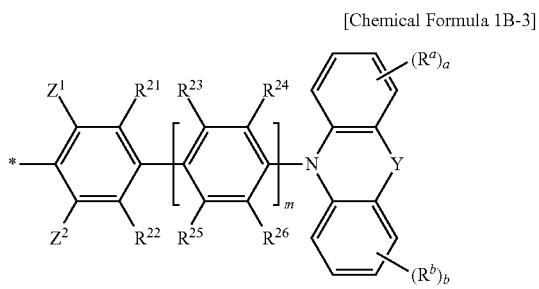

In Chemical Formula 1B-3, m is 1 or 2, $Z^1$ and $Z^2$ are independently hydrogen or a hydroxyl group, $R^{21}$ to $R^{26}$ are independently selected from hydrogen, a halogen, a cyano group, a nitro group, a hydroxyl group, a carboxyl group, an ester group, a substituted or unsubstituted C1 to C20 alkyl group, a substituted or unsubstituted C1 to C20 alkoxy group, a substituted or unsubstituted C6 to C30 aryl group, a substituted or unsubstituted C3 to C20 cycloalkyl group, a substituted or unsubstituted C3 to C20 heteroaryl group, and a substituted or unsubstituted C2 to C20 heterocycloalkyl group, $R^a$ and $R^b$ are independently selected from hydrogen, a halogen, a cyano group, a nitro group, a hydroxyl group, a carboxyl group, an ester group, a substituted or unsubstituted C1 to C20 alkyl group, a substituted or unsubstituted C1 to C20 alkoxy group, a substituted or unsubstituted C6 to C30 aryl group, a substituted or unsubstituted C3 to C20 cycloalkyl group, a substituted or unsubstituted C3 to C20 heteroaryl group, and a substituted or unsubstituted C2 to C20 heterocycloalkyl group, Y is selected from $NR^c$, O, S, Se, and Te (wherein $R^c$ is selected from hydrogen and a substituted or unsubstituted C1 to C6 alkyl group), and a and b are independently an integer that is inclusively between 0 to 4.

Chemical Formula 10 may be selected from functional groups ("one functional group of a plurality of functional groups") represented by Chemical Formulae 1C-1 and 1C-2.

[Chemical Formula 1C-1]

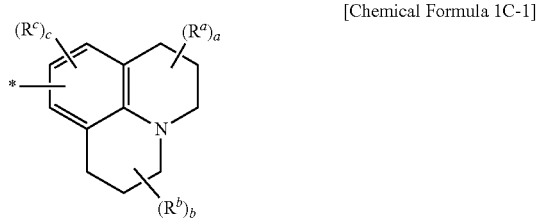

[Chemical Formula 1C-2]

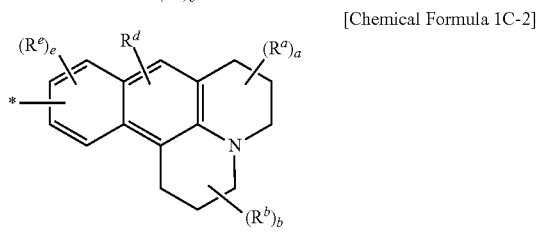

In Chemical Formula 1C-1 and Chemical Formula 1C-2, $R^a$, $R^b$, $R^e$, and $R^d$ are independently selected from hydrogen, a halogen, a cyano group, a nitro group, a hydroxyl group, a carboxyl group, an ester group, a substituted or unsubstituted C1 to C20 alkyl group, a substituted or unsubstituted C1 to C20 alkoxy group, a substituted or unsubstituted C6 to C30 aryl group, a substituted or unsubstituted C3 to C20 cycloalkyl group, a substituted or unsubstituted C3 to C20 heteroaryl group, and a substituted or unsubstituted C2 to C20 heterocycloalkyl group, a and b are independently an integer that is inclusively between 0 to 6, c is an integer that is inclusively between 0 to 2, and e is an integer that is inclusively between 0 to 3.

Chemical Formula 1D may be selected from functional groups represented by Chemical Formula 1D-1, Chemical Formula 1D-2, and Chemical Formula 1D-3.

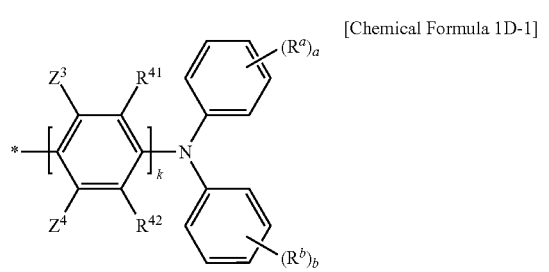

[Chemical Formula 1D-1]

In Chemical Formula 1D-1, k is 0 or 1, $Z^3$ and $Z^4$ are independently hydrogen or a hydroxyl group, $R^{41}$ and $R^{42}$ are independently selected from hydrogen, a halogen, a cyano group, a nitro group, a hydroxyl group, a carboxyl group, an ester group, a substituted or unsubstituted C1 to C20 alkyl group, a substituted or unsubstituted C1 to C20 alkoxy group, a substituted or unsubstituted C6 to C30 aryl group, a substituted or unsubstituted C3 to C20 cycloalkyl group, a substituted or unsubstituted C3 to C20 heteroaryl group, and a substituted or unsubstituted C2 to C20 heterocycloalkyl group, $R^a$ and $R^b$ are independently selected from hydrogen, a halogen, a cyano group, a nitro group, a hydroxyl group, a carboxyl group, an ester group, a substituted or unsubstituted C1 to C20 alkyl group, a substituted or unsubstituted C1 to C20 alkoxy group, a substituted or unsubstituted C6 to C30 aryl group, a substituted or unsubstituted C3 to C20 cycloalkyl group, a substituted or unsubstituted C3 to C20 heteroaryl group, and a substituted or unsubstituted C2 to C20 heterocycloalkyl group, and a and b are independently an integer that is inclusively between 0 to 5.

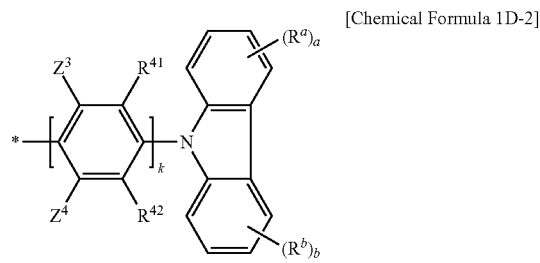

[Chemical Formula 1D-2]

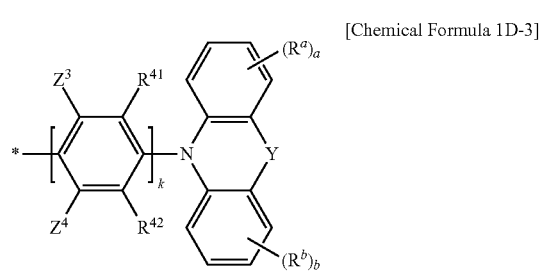

[Chemical Formula 1D-3]

In Chemical Formula 1D-2 and Chemical Formula 1D-3, k is 0 or 1, $Z^3$ and $Z^4$ are independently hydrogen or a hydroxyl group, $R^{41}$ and $R^{42}$ are independently selected from hydrogen, a halogen, a cyano group, a nitro group, a hydroxyl group, a carboxyl group, an ester group, a substituted or unsubstituted C1 to C20 alkyl group, a substituted or unsubstituted C1 to C20 alkoxy group, a substituted or unsubstituted C6 to C30 aryl group, a substituted or unsubstituted C3 to C20 cycloalkyl group, a substituted or unsubstituted C3 to C20 heteroaryl group, and a substituted or unsubstituted C2 to C20 heterocycloalkyl group, $R^a$ and $R^b$ are independently selected from hydrogen, a halogen, a cyano group, a nitro group, a hydroxyl group, a carboxyl group, an ester group, a substituted or unsubstituted C1 to C20 alkyl group, a substituted or unsubstituted C1 to C20 alkoxy group, a substituted or unsubstituted C6 to C30 aryl group, a substituted or unsubstituted C3 to C20 cycloalkyl group, a substituted or unsubstituted C3 to C20 heteroaryl group, and a substituted or unsubstituted C2 to C20 heterocycloalkyl group, Y is selected from $NR^c$, O, S, Se, and Te (wherein $R^c$ is selected from hydrogen and a substituted or unsubstituted C1 to C6 alkyl group), and a and b are independently an integer that is inclusively between 0 to 4.

The squarylium compound may be a particular compound represented by one chemical formula represented by Chemical Formula 4-1, Chemical Formula 4-2, Chemical Formula 4-3, Chemical Formula 4-4, Chemical Formula 4-5, Chemical Formula 4-6, Chemical Formula 4-7, Chemical Formula 4-8, Chemical Formula 4-9, and Chemical Formula 4-10.

[Chemical Formula 4-1]

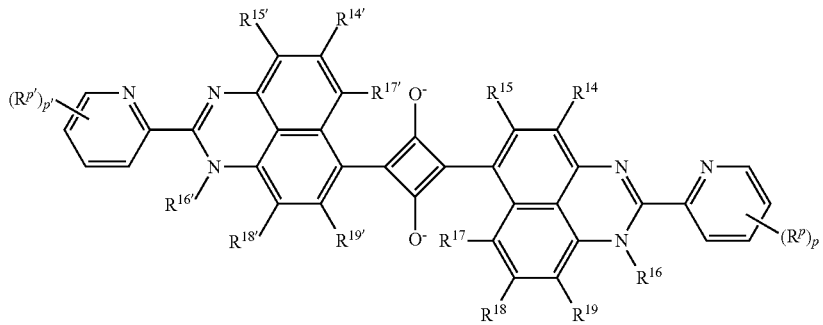

In Chemical Formula 4-1, $R^{14}$, $R^{15}$, $R^{16}$, $R^{17}$, $R^{18}$, $R^{19}$, $R^{14'}$, $R^{15'}$, $R^{16'}$, $R^{17'}$, $R^{18'}$, $R^{19'}$, $R^p$, and $R^{p'}$ are independently selected from hydrogen, a halogen, a cyano group, a nitro group, a hydroxyl group, a carboxyl group, an ester group, a substituted or unsubstituted C1 to C20 alkyl group, a substituted or unsubstituted C1 to C20 alkoxy group, a substituted or unsubstituted C6 to C30 aryl group, a substituted or unsubstituted C3 to C20 cycloalkyl group, a substituted or unsubstituted C3 to C20 heteroaryl group, and a substituted or unsubstituted C2 to C20 heterocycloalkyl group, and p and p' are independently an integer that is inclusively between 0 to 4.

[Chemical Formula 4-2]

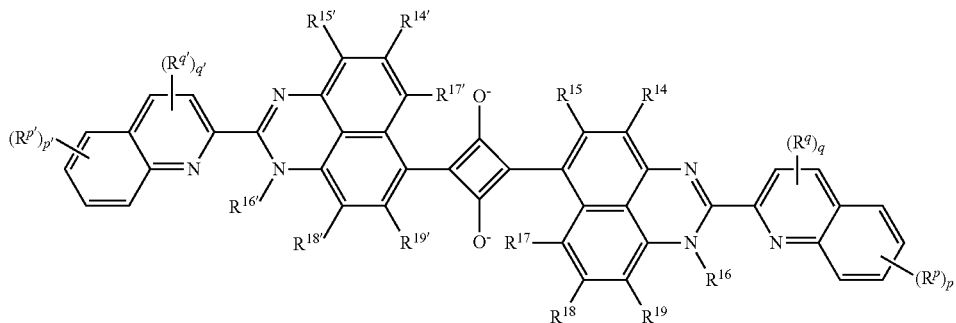

In Chemical Formula 4-2, $R^{14}$, $R^{15}$, $R^{16}$, $R^{17}$, $R^{18}$, $R^{19}$, $R^{14'}$, $R^{15'}$, $R^{16'}$, $R^{17'}$, $R^{18'}$, $R^{19'}$, $R^p$, $R^{p'}$, $R^q$, and $R^{q'}$ are independently selected from hydrogen, a halogen, a cyano group, a nitro group, a hydroxyl group, a carboxyl group, an ester group, a substituted or unsubstituted C1 to C20 alkyl group, a substituted or unsubstituted C1 to C20 alkoxy group, a substituted or unsubstituted C6 to C30 aryl group, a substituted or unsubstituted C3 to C20 cycloalkyl group, a substituted or unsubstituted C3 to C20 heteroaryl group, and a substituted or unsubstituted C2 to C20 heterocycloalkyl group, p and p' are independently an integer that is inclusively between 0 to 4, and q and q' are independently an integer that is inclusively between 0 to 2.

[Chemical Formula 4-3]

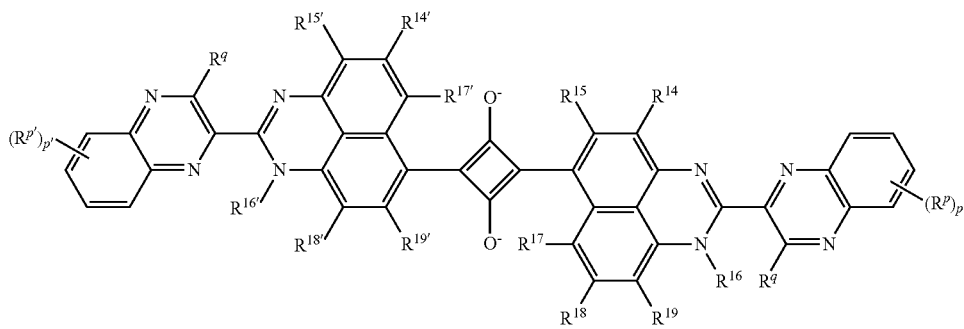

In Chemical Formula 4-3, $R^{14}$, $R^{15}$, $R^{16}$, $R^{17}$, $R^{18}$, $R^{19}$, $R^{14'}$, $R^{15'}$, $R^{16'}$, $R^{17'}$, $R^{18'}$, $R^{19'}$, $R^p$, $R^{p'}$, $R^q$, and $R^{q'}$ are independently selected from hydrogen, a halogen, a cyano group, a nitro group, a hydroxyl group, a carboxyl group, an ester group, a substituted or unsubstituted C1 to C20 alkyl group, a substituted or unsubstituted C1 to C20 alkoxy group, a substituted or unsubstituted C6 to C30 aryl group, a substituted or unsubstituted C3 to C20 cycloalkyl group, a substituted or unsubstituted C3 to C20 heteroaryl group, and a substituted or unsubstituted C2 to C20 heterocycloalkyl group, and p and p' are independently an integer that is inclusively between 0 to 4.

[Chemical Formula 4-4]

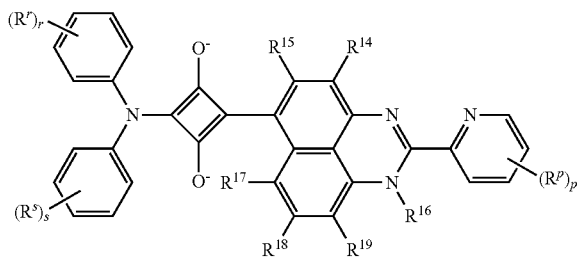

In Chemical Formula 4-4, $R^{14}$, $R^{15}$, $R^{16}$, $R^{17}$, $R^{18}$, $R^{19}$, $R^p$, $R^r$, and $R^s$ are independently selected from hydrogen, a halogen, a cyano group, a nitro group, a hydroxyl group, a carboxyl group, an ester group, a substituted or unsubstituted C1 to C20 alkyl group, a substituted or unsubstituted C1 to C20 alkoxy group, a substituted or unsubstituted C6 to C30 aryl group, a substituted or unsubstituted C3 to C20 cycloalkyl group, a substituted or unsubstituted C3 to C20 heteroaryl group, and a substituted or unsubstituted C2 to C20 heterocycloalkyl group, p is an integer that is inclusively between 0 to 4, and r and s are independently an integer that is inclusively between 0 to 5.

[Chemical Formula 4-5]

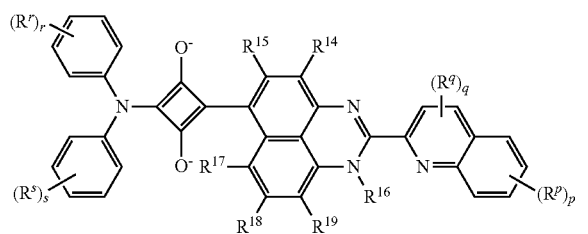

In Chemical Formula 4-5, $R^{14}$, $R^{15}$, $R^{16}$, $R^{17}$, $R^{18}$, $R^{19}$, $R^p$, $R^q$, $R^r$, and $R^s$ are independently selected from hydrogen, a halogen, a cyano group, a nitro group, a hydroxyl group, a carboxyl group, an ester group, a substituted or unsubstituted C1 to C20 alkyl group, a substituted or unsubstituted C1 to C20 alkoxy group, a substituted or unsubstituted C6 to C30 aryl group, a substituted or unsubstituted C3 to C20 cycloalkyl group, a substituted or unsubstituted C3 to C20 heteroaryl group, and a substituted or unsubstituted C2 to C20 heterocycloalkyl group, p is an integer that is inclusively between 0 to 4, q is an integer that is inclusively between 0 to 2, and r and s are independently an integer that is inclusively between 0 to 5.

[Chemical Formula 4-6]

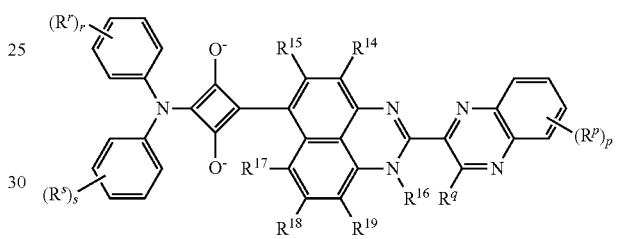

In Chemical Formula 4-6, $R^{14}$, $R^{15}$, $R^{16}$, $R^{17}$, $R^{18}$, $R^{19}$, $R^p$, $R^q$, $R^r$, and $R^s$ are independently selected from hydrogen, a halogen, a cyano group, a nitro group, a hydroxyl group, a carboxyl group, an ester group, a substituted or unsubstituted C1 to C20 alkyl group, a substituted or unsubstituted C1 to C20 alkoxy group, a substituted or unsubstituted C6 to C30 aryl group, a substituted or unsubstituted C3 to C20 cycloalkyl group, a substituted or unsubstituted C3 to C20 heteroaryl group, and a substituted or unsubstituted C2 to C20 heterocycloalkyl group, p is an integer that is inclusively between 0 to 4, q is an integer that is inclusively between 0 to 2, and r and s are independently an integer that is inclusively between 0 to 5.

[Chemical Formula 4-7]

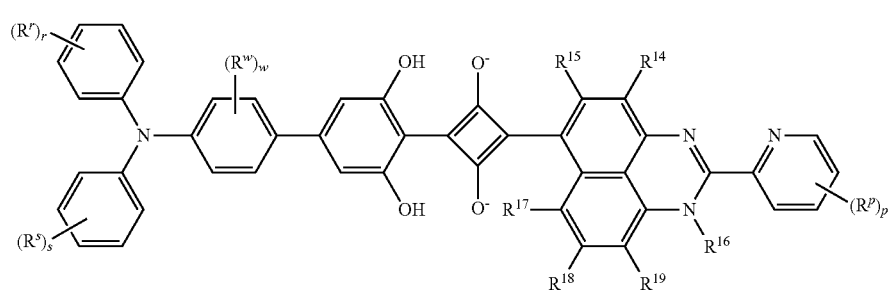

In Chemical Formula 4-7,
R$^{14}$, R$^{15}$, R$^{16}$, R$^{17}$, R$^{18}$, R$^{19}$, R$^p$, R$^q$, R$^r$, R$^s$, and R$^w$ are independently selected from hydrogen, a halogen, a cyano group, a nitro group, a hydroxyl group, a carboxyl group, an ester group, a substituted or unsubstituted C1 to C20 alkyl group, a substituted or unsubstituted C1 to C20 alkoxy group, a substituted or unsubstituted C6 to C30 aryl group, a substituted or unsubstituted C3 to C20 cycloalkyl group, a substituted or unsubstituted C3 to C20 heteroaryl group, and a substituted or unsubstituted C2 to C20 heterocycloalkyl group, p and w are independently an integer that is inclusively between 0 to 4, and r and s are independently an integer that is inclusively between 0 to 5.

[Chemical Formula 4-8]

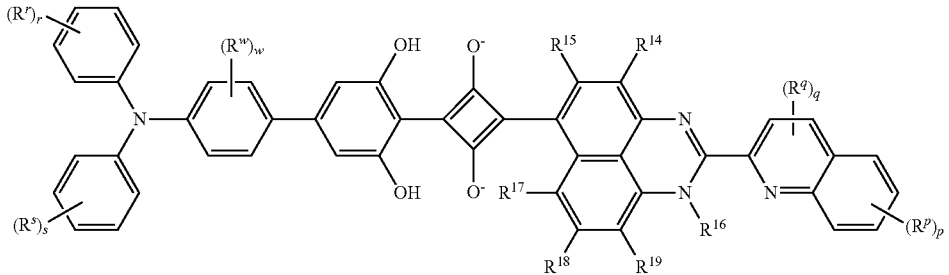

In Chemical Formula 4-8,
R$^{14}$, R$^{15}$, R$^{16}$, R$^{17}$, R$^{18}$, R$^{19}$, R$^p$, R$^q$, R$^r$, R$^s$, and R$^w$ are independently selected from hydrogen, a halogen, a cyano group, a nitro group, a hydroxyl group, a carboxyl group, an ester group, a substituted or unsubstituted C1 to C20 alkyl group, a substituted or unsubstituted C1 to C20 alkoxy group, a substituted or unsubstituted C6 to C30 aryl group, a substituted or unsubstituted C3 to C20 cycloalkyl group, a substituted or unsubstituted C3 to C20 heteroaryl group, and a substituted or unsubstituted C2 to C20 heterocycloalkyl group, p and w are independently an integer that is inclusively between 0 to 4, q is an integer that is inclusively between 0 to 2, and r and s are independently an integer that is inclusively between 0 to 5.

[Chemical Formula 4-9]

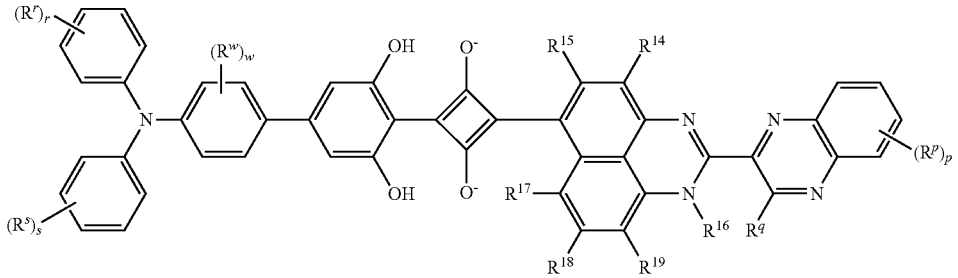

In Chemical Formula 4-9,
R$^{14}$, R$^{15}$, R$^{16}$, R$^{17}$, R$^{18}$, R$^{19}$, R$^p$, R$^q$, R$^r$, R$^s$, and R$^w$ are independently selected from hydrogen, a halogen, a cyano group, a nitro group, a hydroxyl group, a carboxyl group, an ester group, a substituted or unsubstituted C1 to C20 alkyl group, a substituted or unsubstituted C1 to C20 alkoxy group, a substituted or unsubstituted C6 to C30 aryl group, a substituted or unsubstituted C3 to C20 cycloalkyl group, a substituted or unsubstituted C3 to C20 heteroaryl group, and a substituted or unsubstituted C2 to C20 heterocycloalkyl group, p and w are independently an integer that is inclusively between 0 to 4, and r and s are independently an integer that is inclusively between 0 to 5.

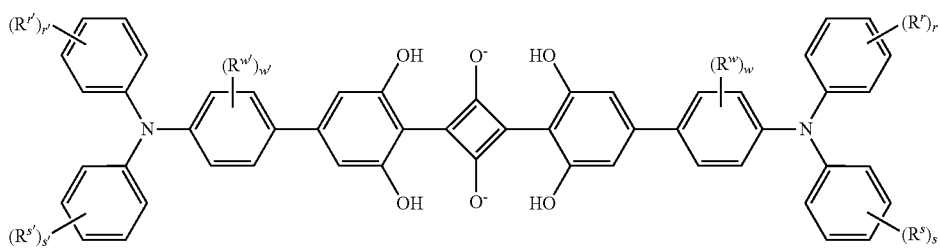

[Chemical Formula 4-10]

In Chemical Formula 4-10, $R^r$, $R^s$, $R^w$, $R^{r'}$, $R^{s'}$, and $R^{w'}$ are independently selected from hydrogen, a halogen, a cyano group, a nitro group, a hydroxyl group, a carboxyl group, an ester group, a substituted or unsubstituted C1 to C20 alkyl group, a substituted or unsubstituted C1 to C20 alkoxy group, a substituted or unsubstituted C6 to C30 aryl group, a substituted or unsubstituted C3 to C20 cycloalkyl group, a substituted or unsubstituted C3 to C20 heteroaryl group, and a substituted or unsubstituted C2 to C20 heterocycloalkyl group, w and w' are independently an integer that is inclusively between 0 to 4, and r, s, r', and s' are independently an integer that is inclusively between 0 to 5.

As described above, the squarylium compound has improved selective light absorbance in an infrared/near infrared wavelength spectrum of light and thus may be applied to an infrared cut film.

Hereinafter, an infrared cut film including the squarylium compound represented by Chemical Formula 1 is described.

The infrared cut film may be manufactured by coating a composition including the squarylium compound represented by Chemical Formula 1 and an organic solvent on a transparent substrate and removing the organic solvent to manufacture a film.

The organic solvent may include for example ethers such as dimethoxyethane, methoxyethoxyethane, tetrahydrofuran, dioxane, and the like, ketones such as acetone, methylethylketone, methylisobutylketone, cyclohexanone, and the like, aromatic hydrocarbons such as benzene, toluene, xylene, monochlorobenzene, and the like, which may be used in an amount of about 10 parts by weight to about 3000 parts by weight based on 1 part by weight of the squarylium compound represented by Chemical Formula 1.

The composition may further include a binder, and the binder may be for example a polyester-based resin, a polycarbonate-based resin, a polyacrylic acid-based resin, a polystyrene-based resin, a polyvinyl chloride-based resin, a polyvinyl acetate-based resin, and the like. The binder may be used in an amount of about 10 parts by weight to about 500 parts by weight based on 1 part by weight of the squarylium compound represented by Chemical Formula 1.

The composition including the squarylium compound represented by Chemical Formula 1 may be coated on the transparent substrate using a known method such as a bar coat method, a spray method, a roll coating method, a dipping method, and the like.

In addition, the infrared cut film may be manufactured by dispersing the squarylium compound represented by Chemical Formula 1 in a resin, molding the resultant, and making it into a film. The resin may be selected from a polyester-based resin, a polycarbonate-based resin, a polyacrylic acid-based resin, a polystyrene-based resin, a polyvinyl chloride-based resin, and a polyvinyl acetate-based resin.

The infrared cut film may be manufactured by further adhering a transparent substrate to a surface of a base film that is manufactured as above, as needed. The transparent substrate is not particularly as long as it is transparent resin or glass having low absorption and scattering properties. The resin may be for example a polyester-based resin, a polycarbonate-based resin, a polyacrylic acid-based resin, a polystyrene-based resin, a polyvinyl chloride-based resin, a polyvinyl acetate-based resin, and the like.

The infrared cut film may be used as an infrared cut filter due to infrared ray/near infrared ray cutting performance.

The infrared cut filter may include an infrared cut film including the squarylium compound represented by Chemical Formula 1 and an infrared light reflection layer disposed on the infrared cut film as needed. An infrared cut filter having such a structure is described referring to FIGS. 1 and 2.

In the drawings, the thickness of layers, films, panels, regions, etc., are exaggerated for clarity. Like reference numerals designate like elements throughout the disclosure. It will be understood that when an element such as a layer, film, region, or substrate is referred to as being "on" another element, it can be directly on the other element or intervening elements may also be present. In contrast, when an element is referred to as being "directly on" another element, there are no intervening elements present.

FIG. 1 is a schematic cross-sectional view of an infrared cut filter according to some example embodiments.

Referring to FIG. 1, an infrared cut filter 1 according to some example embodiments includes an infrared cut film 11 including the squarylium compound represented by Chemical Formula 1 and an infrared light reflection layer 13 disposed on the infrared cut film 11.

The infrared cut film 11 may be manufactured by dispersing the squarylium compound represented by Chemical Formula 1 in a resin, molding the resultant, and making it into a film as described above. The infrared cut film 11 may be a glass substrate including the squarylium compound represented by Chemical Formula 1. The glass substrate may further include copper oxide.

The infrared light reflection layer 13 may be a thin film including an inorganic particulate and may be a deposition film of an inorganic particulate or a metal deposition film. The inorganic particulate may be at least one particulate of silica ($SiO_2$), titania ($TiO_2$) alumina ($Al_2O_3$), zirconia, tantalum pentoxide, niobium pentoxide, lanthanum oxide, yttrium oxide, zinc oxide, zinc sulfide, indium oxide, tin oxide, lanthanum fluoride, magnesium fluoride, sodium hexafluoroaluminate, and the like. Examples of the metal deposition film may be an aluminum deposition film. The deposition film may be for example formed by depositing an inorganic particulate or a metal using a CVD method, a sputtering method, a vacuum deposition method, an ion-assist deposition method, an ion plating method, and the like on the infrared cut film 11, but is not limited thereto.

The infrared light reflection layer 13 may be a thin film that may be formed based on codepositing different kinds of inorganic particulates or a multi-layered thin film including deposited different kinds of inorganic particulates. For example, a first deposition film of an inorganic particulate that is at least one particulate of titania ($TiO_2$), zirconia, and a combination thereof is formed on the infrared cut film 11 and a second deposition film of an inorganic particulate selected from silica ($SiO_2$), alumina, and a combination thereof may be formed thereon. Such inorganic particulate deposition films of the infrared light reflection layer 13 may include 5 to 30 repeated layers.

A thickness of the infrared cut film 11 may be about 50 μm to about 200 μm, for example about 55 μm to about 190 μm or about 60 μm to about 180 μm and a thickness of the infrared light reflection layer 13 may be about 0.1 μm to about 20 μm, for example about 0.5 μm to about 10 μm, or about 0.7 μm to about 5 μm. Within the ranges, infrared light cutting performance may be improved and mechanical strength may be ensured.

Figure 2:
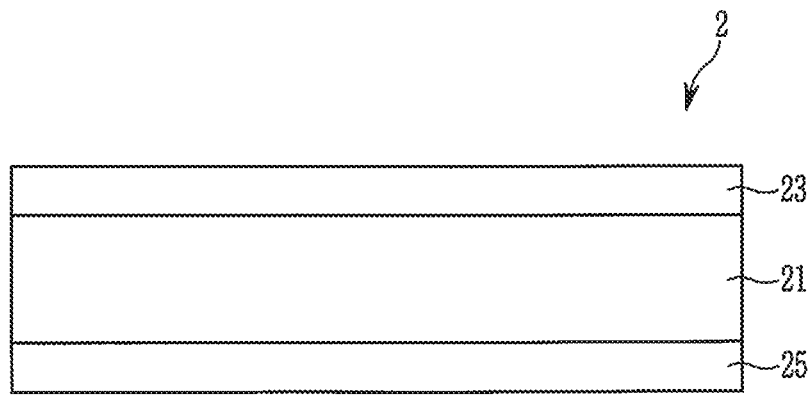
FIG. 2 is a schematic cross-sectional view of an infrared cut filter according to some example embodiments.

FIG. 2 is a schematic cross-sectional view of an infrared cut filter according to some example embodiments.

Referring to FIG. 2, an infrared cut filter 2 according to some example embodiments includes an infrared cut film 21 including the squarylium compound represented by Chemical Formula 1 and a first infrared light reflection layer 23 and a second infrared light reflection layer 25 disposed on both surfaces of the infrared cut film 21.

The infrared cut film 21 may be manufactured by dispersing the squarylium compound represented by Chemical Formula 1 in a resin, molding the resultant, and making it into a film as described above. The infrared cut film 21 may be a glass substrate including the squarylium compound represented by Chemical Formula 1. The glass substrate may further include copper oxide.

The first infrared light reflection layer 23 and the second infrared light reflection layer 25 may be a thin film including an inorganic particulate and may be a deposition film of an inorganic particulate or a metal deposition film. The inorganic particulate may be silica ($SiO_2$), titania ($TiO_2$) alumina ($Al_2O_3$), zirconia, tantalum pentoxide, niobium pentoxide, lanthanum oxide, yttrium oxide, zinc oxide, zinc sulfide, indium oxide, tin oxide, lanthanum fluoride, magnesium fluoride, sodium hexafluoroaluminate, and the like. Examples of the metal deposition film may be an aluminum deposition film. The deposition film may be for example formed by depositing an inorganic particulate or a metal using a CVD method, a sputtering method, a vacuum deposition method, an ion-assist deposition method, an ion plating method, and the like on the infrared cut film 21, but is not limited thereto.

The first infrared light reflection layer 23 and the second infrared light reflection layer 25 reflect light in an infrared ray wavelength spectrum of light effectively, and thereby optical distortion by light in an infrared ray wavelength spectrum of light may be effectively reduced or prevented. The first infrared light reflection layer 23 and the second infrared light reflection layer 25 may reflect light in a part of a near infrared wavelength spectrum of light, a mid-infrared wavelength spectrum of light, and a far-infrared wavelength spectrum of light, for example light in a wavelength spectrum of light of about 700 nm to 3 μm.

The first infrared light reflection layer 23 and the second infrared light reflection layer 25 is not particularly limited as long as it reflects light in an infrared ray wavelength spectrum of light, and may be for example a high refractive reflective layer, a reflective layer including a nano particle having a high refractive index or a multilayer including a plurality of layers having different refractive indexes, but is not limited thereto.

The first infrared light reflection layer 23 and the second infrared light reflection layer 25 may be a thin film obtained by codepositing different kinds of inorganic particulates or a multi-layered thin film obtained by depositing different kinds of inorganic particulates.

For example, the first infrared light reflection layer 23 and the second infrared light reflection layer 25 may include a first layer and a second layer consisting of each material having a different refractive index and may include a multilayer including the first layer and the second layer that are alternately and repeatedly stacked.

Each of the first layer and the second layer may be for example a dielectric layer including oxide layer, a nitride layer, an oxynitride layer, a sulfide layer, or a combination thereof, and for example the first layer may have a refractive index of less than about 1.7 and the second layer may have a refractive index of greater than or equal to about 1.7. Within the ranges, for example the first layer may have a refractive index of greater than or equal to about 1.1 and less than 1.7 and the second layer may have a refractive index of about 1.7 to about 2.7, or within the ranges, for example the first layer may have a refractive index of about 1.2 to about 1.6 and the second layer may have a refractive index of about 1.8 to about 2.5.

The first layer and the second layer may include a material having the refractive indexes without a particular limit, and the first layer may include for example silicon oxide, aluminum oxide, or a combination thereof and the second layer may include titanium oxide, zinc oxide, indium oxide, zirconium oxide, or a combination thereof. The first layer and the second layer may have for example five layers to eighty layers, for example five layers to fifty layers.

Each thickness of the first layer and the second layer may be determined according to a refractive index and a reflection wavelength of each layer and for example each first layer may have a thickness of about 10 nm to about 700 nm and each second layer may have a thickness of about 30 nm to about 600 nm. Thicknesses of the first layer and the second layer may be the same or different.

A thickness of the infrared cut film 21 may be about 50 μm to about 200 μm, for example about 55 μm to about 190 μm or about 60 μm to about 180 μm and each thickness of the first infrared light reflection layer 23 and the second infrared light reflection layer 25 may be about 0.1 μm to about 20 μm, for example about 0.5 μm to about 10 μm, or about 0.7 μm to about 5 μm. Within the ranges, infrared light cutting performance may be improved and mechanical strength may also be ensured.

As described above, the squarylium compound may be applied to various electronic devices due to improved selective light absorbance in an infrared/near infrared wavelength spectrum of light. The electronic devices may be for example an image sensor, a liquid crystal display, a plasma display, an organic electroluminescence display, a laser display, a solar cell, a bio sensor, an illumination, and the like. Particularly, a compound having improved absorbance in an infrared/near infrared wavelength spectrum of light such as the squarylium compound may improve spectral sensitivity at a low illumination, and may be usefully used in an iris identification sensor, a night vision device, and the like.

Hereinafter, an image sensor as an example of an electronic device id described with reference to the drawings.

An image sensor according to some example embodiments includes a first photo-sensing device configured to sense light in a blue wavelength spectrum of light,
a second photo-sensing device configured to sense light in a red wavelength spectrum of light,
a third photo-sensing device configured to sense light in a green wavelength spectrum of light, and
a fourth photo-sensing device configured to sense light in an infrared/near infrared wavelength spectrum of light,
wherein the fourth photo-sensing device may include the squarylium compound.

The first photo-sensing device to the fourth photo-sensing device may be arranged (may extend) adjacently and parallel or perpendicular, to each other collectively in the form of a single group.

The first photo-sensing device to the fourth photo-sensing device may each be an inorganic photodiode or an organic photodiode and at least one of the first photo-sensing device to the fourth photo-sensing device may be an organic photodiode.

The inorganic photodiode may be for example a silicon photodiode, but is not limited thereto.

The organic photodiode may be an organic photoelectric device including a pair of light-transmitting electrodes facing each other and a photoactive layer disposed between them and including an organic light-absorbing material.

One of the pair of light-transmitting electrodes may be an anode and the other may be a cathode. The light-transmitting electrodes may be made of, for example, a transparent conductor such as indium tin oxide (ITO), indium zinc oxide (IZO), zinc oxide (ZnO), tin oxide (SnO), aluminum tin oxide (AITO), and fluorine-doped tin oxide (FTO), or may be a metal thin layer having a thin thickness of several nanometers or several tens of nanometers or a metal thin layer having a thin thickness of several nanometers to several tens of nanometers doped with a metal oxide.

The photoactive layer is a layer including a p-type semiconductor material and an n-type semiconductor material to provide a pn junction, which is a layer producing excitons by receiving light from outside and then separating holes and electrons from the produced excitons.

The photoactive layer may include an intrinsic layer including both the p-type semiconductor and the n-type semiconductor and may be formed according to a method of, for example, co-deposition and the like. In addition, the photoactive layer may further include at least one selected from a p-type layer and an n-type layer besides the intrinsic layer, wherein the p-type layer may include a p-type semiconductor material, and the n-type layer may include an n-type semiconductor material. The kind of the p-type semiconductor material and the n-type semiconductor material may be determined according to the absorption wavelength.

At least one of charge auxiliary layers may be further included between the light-transmitting electrode and the photoactive layer. The charge auxiliary layer may further facilitate the movement of holes and electrons separated from the photoactive layer to enhance efficiency, and may be at least one selected from, for example, a hole injection layer (HIL) facilitating hole injection, a hole transport layer (HTL) facilitating hole transportation, an electron blocking layer (EBL) blocking electron transportation, an electron injection layer (EIL) facilitating electron injection, an electron transport layer (ETL) facilitating electron transportation, and a hole blocking layer (HBL) blocking hole transportation.

The hole transport layer (HTL) may include, for example one selected from poly(3,4-ethylenedioxythiophene):poly (styrenesulfonate) (PEDOT:PSS), polyarylamine, poly(N-vinylcarbazole), polyaniline, polypyrrole, N,N,N',N'-tetrakis(4-methoxyphenyl)-benzidine (TPD), 4-bis[N-(1-naphthyl)-N-phenyl-amino]biphenyl (α-NPD), m-MTDATA, 4,4',4''-tris(N-carbazolyl)-triphenylamine (TCTA), tungsten oxide (WOx, $0<x\leq3$), molybdenum oxide ($MO_x$, $1<x\leq3$), vanadium oxide ($V_2O_5$), rhenium oxide, nickel oxide ($NiO_x$, $1<x\leq4$), copper oxide, titanium oxide, molybdenum sulfide, and a combination thereof, but is not limited thereto.

The electron blocking layer (EBL) may include one selected from, for example, poly(3,4-ethylenedioxythiophene):poly(styrenesulfonate) (PEDOT:PSS), polyarylamine, poly(N-vinylcarbazole), polyaniline, polypyrrole, N,N,N',N'-tetrakis(4-methoxyphenyl)-benzidine (TPD), 4-bis[N-(1-naphthyl)-N-phenyl-amino]biphenyl (α-NPD), m-MTDATA, 4,4',4''-tris(N-carbazolyl)-triphenylamine (TCTA), and a combination thereof, but is not limited thereto.

The electron transport layer (ETL) may include one selected from, for example, 1,4,5,8-naphthalene-tetracarboxylic dianhydride (NTCDA), bathocuproine (BCP), LiF, Alq3, Gaq3, Inq3, Znq2, Zn(BTZ)2, BeBq2, aluminum (Al), magnesium (Mg), molybdenum (Mo), aluminum oxide, magnesium oxide, molybdenum oxide, and a combination thereof, but is not limited thereto.

The hole blocking layer (HBL) may include one selected from, for example 1,4,5,8-naphthalene-tetracarboxylic dianhydride (NTCDA), dicyanovinyl-terthiophene (DCV3T), bathocuproine (BCP), LiF, Alq3, Gaq3, Inq3, Znq2, Zn(BTZ)2, BeBq2, and a combination thereof, but is not limited thereto.

The organic photoelectric device may produce excitons at the inside thereof when light in a predetermined region is adsorbed in the photoactive layer by entering light from one light-transmitting electrode side. The excitons are separated into holes and electrons in the photoactive layer, and the separated holes may be transported into an anode side and the separated electrons may be transported into a cathode side to flow current through the organic photoelectric device.

In an image sensor according to some example embodiments, the first photo-sensing device, the second photo-sensing device, the third photo-sensing device, and the fourth photo-sensing device may be an inorganic photodiode.

Figure 3:
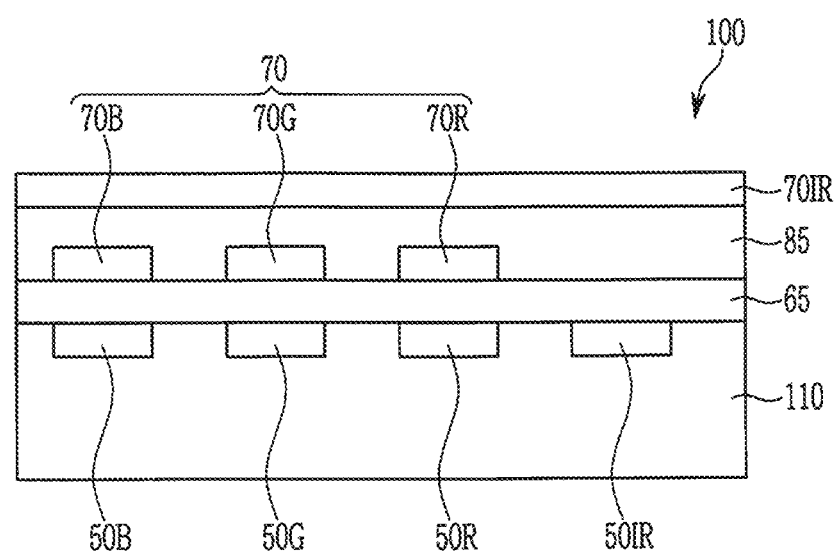
FIGS. 3 to 18 are schematic cross-sectional views of image sensors according to some example embodiments.

FIG. 3 is a schematic cross-sectional view of an image sensor according to some example embodiments.

Referring to FIG. 3, an image sensor 100 includes a semiconductor substrate 110 integrated with a blue photodiode 50B, a green photodiode 50G, a red photodiode 50R, an infrared light/near infrared light diode (infrared photodiode) 501R, and a transmission transistor (not shown), a lower insulation layer 65, a color filter layer 70, an upper insulation layer 85, and an infrared cut filter 701R.

The semiconductor substrate 110 may be a silicon substrate and may be integrated with the blue photodiode 50B, the green photodiode 50G, the red photodiode 50R, the infrared light/near infrared light diode 501R, and the transmission transistor (not shown). The blue photodiode 50B, the green photodiode 50G, the red photodiode 50R may be respectively integrated in each of a blue pixel, a green pixel, and a red pixel. The blue photodiode 50B, the green photodiode 50G, the red photodiode 50R, and the infrared light/near infrared light diode 501R may sense light, and the sensed information may be transferred by a transport transistor. The transmission transistor may transfer photocharges generated by the photodiode to a driving transistor (not shown).

Metal wires (not shown) and pads (not shown) are formed on the semiconductor substrate 110. In order to decrease signal delay, the metal wires and pads may be made of a metal having low resistivity, for example, aluminum (Al), copper (Cu), silver (Ag), and alloys thereof, but are not limited thereto.

The lower insulation layer 65 may be formed on the metal wires and pads. The lower insulation layer 65 may be made of an inorganic insulation material such as a silicon oxide and/or a silicon nitride, or a low dielectric constant (low K) material such as SiC, SiCOH, SiCO, and SiOF.

The color filter layer 70 formed on the lower insulation layer 65 includes a blue filter 70B formed in a blue pixel, a green filter 70G formed in a green pixel, and a red filter 70R formed in a red pixel.

The upper insulation layer 85 is formed on the color filter layer 70. The upper insulation layer 85 removes steps caused by the color filter layer 70, and planarize it. The upper insulation layer 85 and the lower insulation layer 65 may include a contact hole (not shown) to expose pads.

The infrared cut filter 701R is formed on the upper insulation layer 85. The infrared cut filter 701R includes the squarylium compound represented by Chemical Formula 1. The infrared cut film (IR) may selectively absorb light in an infrared ray (particularly, near infrared ray) region of greater than or equal to about 700 nm and less than or equal to about 1300 nm without absorption in a visible wavelength spectrum of light.

As described above, the color filter layer 70 including the color filters 70B, 70G, and 70R absorbing light in a visible ray region and the infrared cut filter 701R are vertically stacked and thereby an area absorbing infrared light may be enlarged and absorption efficiency may be increased.

A focusing lens (not shown) may be further formed on the infrared cut filter 701R. The focusing lens may control a direction of incident light and gather the light in one region. The focusing lens may have a shape of, for example, a cylinder or a hemisphere, but is not limited thereto.

Figure 4:
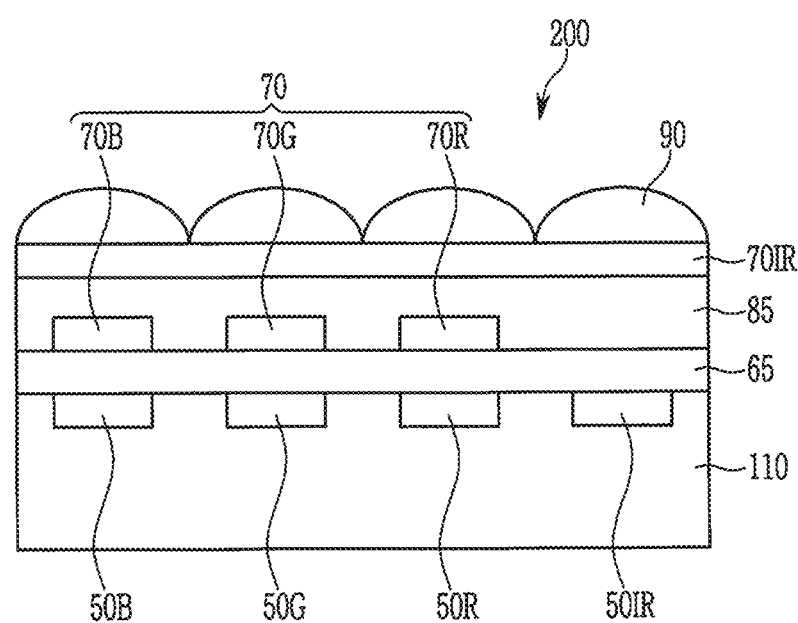

As shown in FIG. 4, an image sensor 200 includes a focusing lens 90 formed on the upper insulation layer 85 and the infrared cut filter 701R formed on the focusing lens 90.

Figure 5:
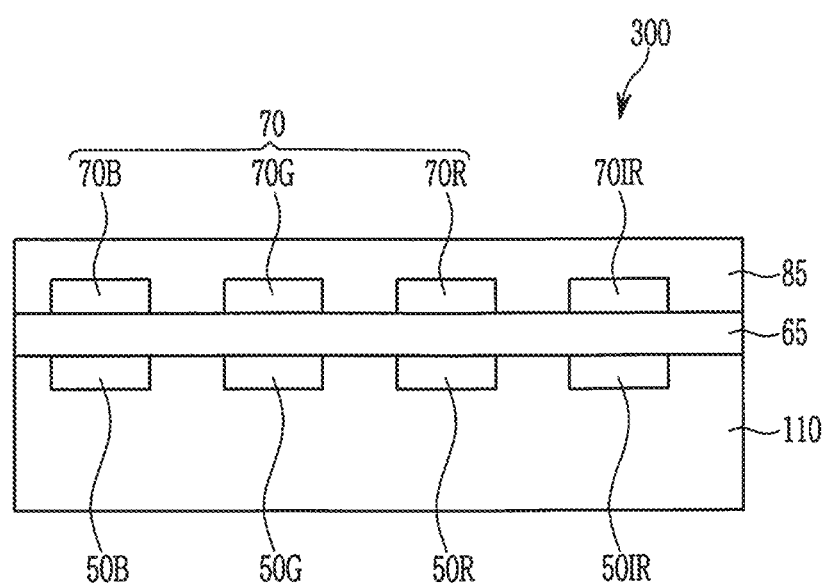

In an image sensor according to some example embodiments, the infrared cut filter 701R may be disposed only on an infrared light/near infrared light diode. FIG. 5 is a schematic cross-sectional view showing such an image sensor 30.

In an image sensor according to some example embodiments, the first photo-sensing device ("photodiode"), the second photo-sensing device, and the third photo-sensing device may be an organic photodiode and the fourth photo-sensing device may be an inorganic photodiode.

Figure 6:
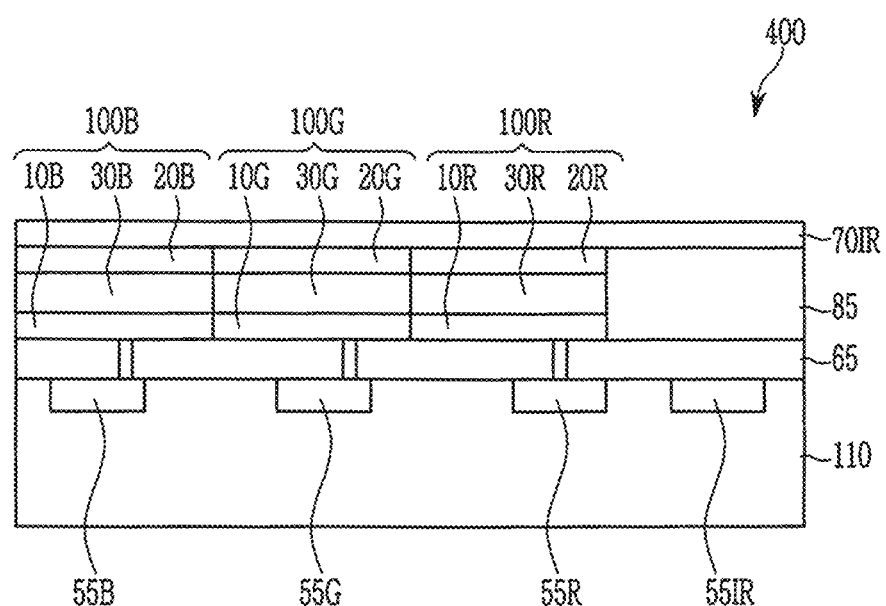

FIG. 6 is a schematic cross-sectional view showing an image sensor according to some example embodiments.

Referring to FIG. 6, an image sensor 400 according to some example embodiments includes a semiconductor substrate 110 integrated with an infrared photodiode 501R, a blue charge storage 55B, a green charge storage 55G, a red charge storage 55R, and a transmission transistor (not shown), a lower insulation layer 65, an upper insulation layer 85, a blue photo-sensing device 100B, a green photo-sensing device 100G, and a red photo-sensing device 100R.

The semiconductor substrate 110 may be a silicon substrate, and may be integrated with the infrared photodiode 501R, the blue charge storage 55B, the green charge storage 55G, the red charge storage 55R, and the transmission transistor (not shown). The blue charge storage 55B, the green charge storage 55G, and the red charge storage 55R may be respectively integrated in each of a blue pixel, a green pixel, and a red pixel. The infrared photodiode 501R may absorb light in an infrared ray (particularly, a near infrared ray) region and the sensed information may be transferred by a transport transistor.

Charges absorbed in the blue photo-sensing device 100B, the green photo-sensing device 100G, and the red photo-sensing device 100R are collected in the blue charge storage 55B, the green charge storage 55G, and the red charge storage 55R which are electrically connected to each of the blue photo-sensing device 100B, the green photo-sensing device 100G, and the red photo-sensing device 100R.

Metal wires (not shown) and pads (not shown) are formed on the semiconductor substrate 110. In order to decrease signal delay, the metal wires and pads may be made of a metal having low resistivity, for example, aluminum (Al), copper (Cu), silver (Ag), and alloys thereof, but are not limited thereto.

The lower insulation layer 65 may be formed on the metal wires and pads. The lower insulation layer 65 may be made of an inorganic insulation material such as a silicon oxide and/or a silicon nitride, or a low dielectric constant (low K) material such as SiC, SiCOH, SiCO, and SiOF.

The blue photo-sensing device 100B, the green photo-sensing device 100G, and the red photo-sensing device 100R are formed on the lower insulation layer 65. The blue photo-sensing device 100B includes a lower electrode 10B, an upper electrode 20B, and a photoactive layer 30B selectively absorbing light in a blue wavelength spectrum of light, the green photo-sensing device 100G includes a lower electrode 10G, an upper electrode 20G and a photoactive layer 30G selectively absorbing light in a green wavelength spectrum of light, and the red photo-sensing device 100R includes a lower electrode 10R, an upper electrode 20R, and a photoactive layer 30R selectively absorbing light in a red wavelength spectrum of light.

The lower electrodes 10B, 10G, and 10R and the upper electrodes 20B, 20G, and 20R may be light-transmitting electrodes and may be made of, for example, a transparent conductor such as indium tin oxide (ITO), indium zinc oxide (IZO), zinc oxide (ZnO), tin oxide (SnO), aluminum tin oxide (AITO), and fluorine-doped tin oxide (FTO), or may be a metal thin layer having a thin thickness of several nanometers or several tens of nanometers or a metal thin layer having a thin thickness of several nanometers to several tens of nanometers doped with a metal oxide.

The photoactive layers 30B, 30G, and 30R may include a p-type semiconductor material and an n-type semiconductor material. The photoactive layer 30B of the blue photo-sensing device 100B may include a p-type semiconductor material selectively absorbing light in a blue wavelength spectrum of light and an n-type semiconductor material selectively absorbing light in a blue wavelength spectrum of light, the photoactive layer 30G of the green photo-sensing device 100G may include a p-type semiconductor material selectively absorbing light in a green wavelength spectrum of light and an n-type semiconductor material selectively absorbing light in a green wavelength spectrum of light, and the photoactive layer 30R of the red photo-sensing device 100R may include a p-type semiconductor material selectively absorbing light in a red wavelength spectrum of light and an n-type semiconductor material selectively absorbing light in a red wavelength spectrum of light.

The upper insulation layer 85 is formed on the lower insulation layer 65. The upper insulation layer 85 is disposed on the infrared photodiode 501R and may reduce steps with the blue photo-sensing device 100B, the green photo-sensing device 100G, and the red photo-sensing device 100R.

The infrared cut filter 70IR is disposed on the blue photo-sensing device 100B, the green photo-sensing device 100G, the red photo-sensing device 100R, and the upper insulation layer 85. The infrared cut filter 701R includes the squarylium compound represented by Chemical Formula 1. The infrared cut film (IR) may selectively absorb light in an infrared ray (particularly, near infrared ray) region of greater than or equal to about 700 nm and less than or equal to about 1300 nm without absorption in a visible wavelength spectrum of light.

As shown in FIG. 6, the infrared cut filter 701R is formed on an entire surface of a blue pixel, a green pixel, and a red pixel, and thereby an area absorbing infrared light may be enlarged and absorption efficiency may be increased.

The blue photo-sensing device 100B, the green photo-sensing device 100G, and the red photo-sensing device 100R may be vertically stacked. In this way, the area of the image sensor may be decreased and down-sizing of the image sensor may be implemented by stacking the photo-sensing devices 100B, 100G, and 100R vertically. A stacking order of the photo-sensing devices 100B, 100G, and 100R are not particularly limited.

A focusing lens (not shown) may be further formed on the infrared ray filter 701R. The focusing lens may control a direction of incident light and gather the light in one region. The focusing lens may have a shape of, for example, a cylinder or a hemisphere, but is not limited thereto.

In addition, the image sensor 400 may include a focusing lens formed on the blue photo-sensing device 100B, the green photo-sensing device 100G, the red photo-sensing device 100R, and the upper insulation layer 85, and the infrared ray filter 70IR formed on the focusing lens.

The infrared ray filter 701R of FIG. 6 may be formed at a position corresponding to the infrared light/near infrared light diode 501R as shown in FIG. 5.

In an image sensor according to some example embodiments, the third photo-sensing device may be an organic photodiode and the first photo-sensing device, the second photo-sensing device, and the fourth photo-sensing device may be an inorganic photodiode.

Figure 7:
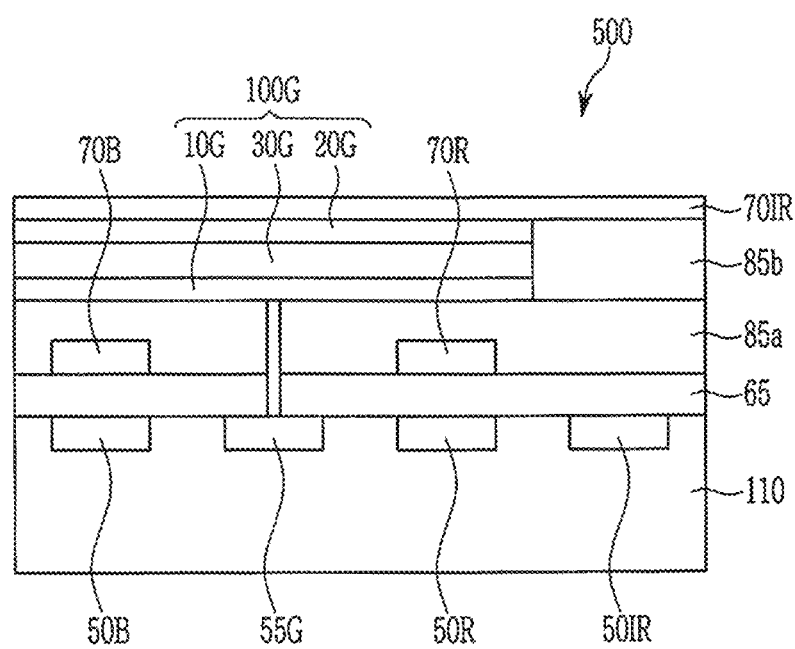

FIG. 7 is a schematic cross-sectional view showing an image sensor according to some example embodiments.

Referring to FIG. 7, an image sensor 50 according to some example embodiments includes a semiconductor substrate 110 integrated with a blue photodiode 50B, a red photodiode 50R, a green charge storage 55G, an infrared light/near infrared light diode 50IR, and a transmission transistor (not shown), a lower insulation layer 65, color filter layers ("color filters") 70B and 70R, a first upper insulation layer 85a, a green photo-sensing device 100G, a second upper insulation layer 85b, and an infrared ray filter 70IR.

The semiconductor substrate 110 may be a silicon substrate and may be integrated with the blue photodiode 50B, the red photodiode 50R, the green charge storage 55G, the infrared light/near infrared light diode 50IR, and the transmission transistor (not shown). The blue photodiode 50B and the transmission transistor may be integrated in each of a blue pixel, the red photodiode 50R and the transmission transistor integrated in each of a red pixel, and the green charge storage 55G and the transmission transistor integrated in each of a green pixel.

Metal wires (not shown) and pads (not shown) are formed on the semiconductor substrate 110. In order to decrease signal delay, the metal wires and pads may be made of a metal having low resistivity, for example, aluminum (Al), copper (Cu), silver (Ag), and alloys thereof, but are not limited thereto. However, the image sensor is not limited to the structure and the metal wires and pads may be disposed under the blue photodiode 50B, the red photodiode 50R, the green charge storage 55G, and the infrared light/near infrared light diode 501R.

The lower insulation layer 65 may be formed on the metal wires and pads. The lower insulation layer 65 may be made of an inorganic insulation material such as a silicon oxide and/or a silicon nitride, or a low dielectric constant (low K) material such as SiC, SiCOH, SiCO, and SiOF.

Color filters 70B and 70R may be formed on the lower insulation layer 65. The color filter 70B of the blue pixel adsorbs light in the blue wavelength spectrum of light and transfers it to the blue photo-sensing device 50B, and the color filter 70R of the red pixel adsorbs light in the red wavelength spectrum of light and transfers it to the red photo-sensing device 50R. The green pixel does not include a color filter.

The first upper insulation layer 85a is formed on the color filters 70B and 70R. The first upper insulation layer 85a removes steps caused by the color filter 70B and 70R, and planarizes it.

The green photo-sensing device 100G and the second upper insulation layer 85b are formed on the first upper insulation layer 85a. The green photo-sensing device 100G includes light-transmitting electrodes 10G and 20G and a photoactive layer 30G.

One of the light-transmitting electrodes 10G and 20G may be an anode and the other may be a cathode. The light-transmitting electrodes 10G and 20G may be made of, for example, a transparent conductor such as indium tin oxide (ITO), indium zinc oxide (IZO), zinc oxide (ZnO), tin oxide (SnO), aluminum tin oxide (AITO), and fluorine-doped tin oxide (FTO), or may be a metal thin layer having a thin thickness of several nanometers or several tens of nanometers or a metal thin layer having a thin thickness of several nanometers to several tens of nanometers doped with a metal oxide.

The photoactive layer 30G selectively absorbs light in a green wavelength spectrum of light and passes light in other wavelength spectrum of lights except the green wavelength spectrum of light, which are the blue wavelength spectrum of light and the red wavelength spectrum of light.

The photoactive layer 30G may include a p-type semiconductor compound selectively adsorbing light in the green wavelength spectrum of light and an n-type semiconductor compound selectively adsorbing light in the green wavelength spectrum of light, and the p-type semiconductor compound and the n-type semiconductor compound may provide a pn junction. The photoactive layer 30G selectively adsorbs light in the green wavelength spectrum of light and produces excitons, and then the produced excitons are separated into holes and electrons to impart the photoelectric effects. The photoactive layer 30G may be substituted for a color filter of the green pixel.

Each of the p-type semiconductor material and the n-type semiconductor material may have an energy bandgap of, for example, about 2.0 to about 2.5 eV, and the p-type semiconductor material and the n-type semiconductor material may have a LUMO difference of, for example, about 0.2 to about 0.7 eV.

The p-type semiconductor material may be, for example, quinacridone or a derivative thereof, and the n-type semiconductor material may be, for example, a cyanovinyl group-containing a thiophene derivative, but they are not limited thereto.

The green photo-sensing device 100G may produce excitons at the inside when light enters from the upper electrode 20G, and the photoactive layer 30G absorbs light in the green wavelength spectrum of light. Excitons are separated into holes and electrons in the photoactive layer 30G, and the separated holes are moved to the anode side, which is one of the lower electrode 10G and the upper electrode 20G, and the separated electrons are moved to a cathode which is the other of the lower electrode 10G and the upper electrode 20G, so as to flow a current. The separated electrons or holes may be collected in the charge storage 55G. Light in other wavelength spectrum of lights except the green wavelength spectrum of light may pass through the green photo-sensing device 100G and the color filters 70B and 70R, and may be sensed by the blue photo-sensing device 50B or the red photo-sensing device 50R.

The photoactive layer 30G may be formed on an entire surface of the blue pixel (B), the red pixel (R), and the green pixel (G), such that the light absorption area is increased to accomplish the high light-absorptive efficiency.

The second upper insulation layer 85b may be disposed on the infrared photodiode 501R and may reduce steps with the green photo-sensing device 100G.

The infrared cut filter 701R is formed on the green photo-sensing device 100G and the upper insulation layer 80b. The infrared cut filter 701R includes the squarylium compound represented by Chemical Formula 1. The infrared cut film (IR) may selectively absorb light in an infrared ray (particularly, near infrared ray) region of greater than or equal to about 700 nm and less than or equal to about 1300 nm without absorption in a visible wavelength spectrum of light.

A focusing lens (not shown) may be further formed on the infrared ray filter 701R. The focusing lens may control a direction of incident light and gather the light in one region. The focusing lens may have a shape of, for example, a cylinder or a hemisphere, but is not limited thereto.

In addition, the image sensor 50 may include a focusing lens formed on the green photo-sensing device 1000 and the second upper insulation layer 85b and the infrared cut filter 701R formed on the focusing lens.

In some example embodiments, for better understanding and ease of description, the structure in which the green photo-sensing device 100G is stacked is exemplified, but it is not limited thereto. The structure may be stacked with the red photo-sensing device 100R or the blue photo-sensing device 100B instead of the green photo-sensing device 100G.

As described above, an area of the image sensor may be decreased and down-sizing of the image sensor may be implemented by vertically stacking a color filter layer including color filters absorbing light in a blue wavelength spectrum of light and light in a red wavelength spectrum of light of a visible ray region, a green photo-sensing device absorbing light in a green wavelength spectrum of light, and an infrared cut filter absorbing light in an infrared light. In addition, a photo-sensing device selectively absorbing light in a green wavelength spectrum of light and an infrared cut filter are formed on an entire surface of an image sensor and an area absorbing light may be enlarged and absorption efficiency may be increased.

In an image sensor according to some example embodiments, the first photo-sensing device, the second photo-sensing device, the third photo-sensing device, and the fourth photo-sensing device may be an organic photodiode.

Figure 8:
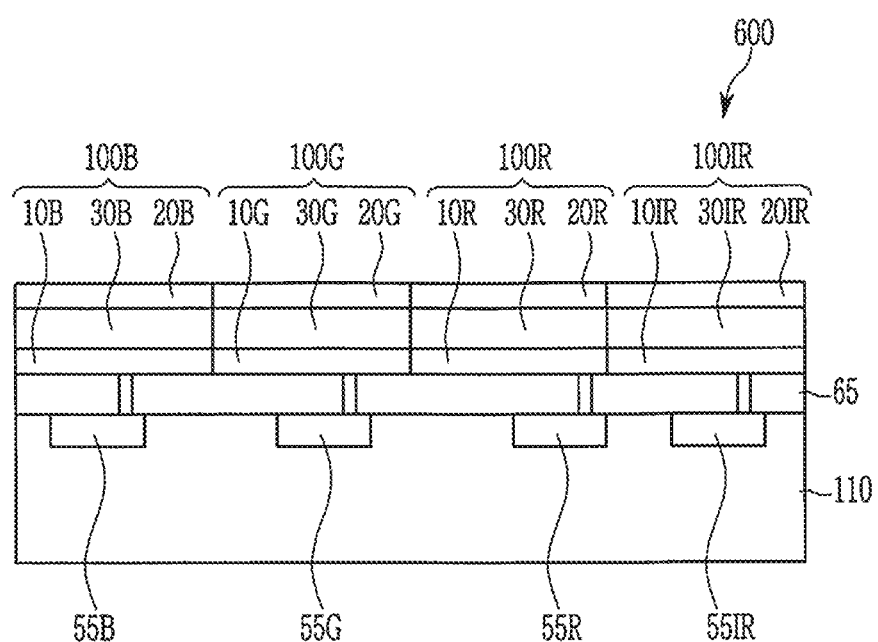

FIG. 8 is a schematic cross-sectional view showing an image sensor according to some example embodiments.

Referring to FIG. 8, an image sensor 600 according to some example embodiments includes a semiconductor substrate 110 integrated with an infrared light/near infrared light charge storage 551R, a blue charge storage 55B, a green charge storage 55G, a red charge storage 55R, and a transmission transistor (not shown), a lower insulation layer 65, a blue photo-sensing device 100B, a green photo-sensing device 1000, a red photo-sensing device 100R and an infrared/near infrared photo-sensing device 100IR.

The semiconductor substrate 110 may be a silicon substrate and may be integrated with the infrared light/near infrared light charge storage 551R, the blue charge storage 55B, the green charge storage 55G, the red charge storage 55R, and the transmission transistor (not shown). The blue charge storage 55B, the green charge storage 55G, and the red charge storage 55R may be respectively integrated in each of a blue pixel, a green pixel, and a red pixel.

Charges absorbed in the infrared/near infrared photo-sensing device 100IR, the blue photo-sensing device 100B, the green photo-sensing device 1000, and the red photo-sensing device 100R are collected in in the infrared light/near infrared light charge storage 551R, the blue charge storage 55B, the green charge storage 55G, and the red charge storage 55R which are electrically connected to each of the infrared/near infrared photo-sensing device 100IR, the blue photo-sensing device 100B, the green photo-sensing device 1000, and the red photo-sensing device 100R.

Metal wires (not shown) and pads (not shown) are formed on the semiconductor substrate 110. In order to decrease signal delay, the metal wires and pads may be made of a metal having low resistivity, for example, aluminum (Al), copper (Cu), silver (Ag), and alloys thereof, but are not limited thereto.

The lower insulation layer 65 may be formed on the metal wires and pads. The lower insulation layer 65 may be made of an inorganic insulation material such as a silicon oxide and/or a silicon nitride, or a low dielectric constant (low K) material such as SiC, SiCOH, SiCO, and SiOF.

The blue photo-sensing device 100B, the green photo-sensing device 1000, the red photo-sensing device 100R, and the infrared/near infrared photo-sensing device 100IR are formed on the lower insulation layer 65. The blue photo-sensing device 100B includes a lower electrode 10B, an upper electrode 20B, and a photoactive layer 30B selectively absorbing light in a blue wavelength spectrum of light, the green photo-sensing device 100G includes a lower electrode 10G, an upper electrode 20G and a photoactive layer 30G selectively absorbing light in a green wavelength spectrum of light, the red photo-sensing device 100R includes a lower electrode 10R, an upper electrode 20R, and a photoactive layer 30R selectively absorbing light in a red wavelength spectrum of light, and the infrared/near infrared photo-sensing device 100IR includes a lower electrode 10IR, an upper electrode 201R, and a photoactive layer 301R selectively absorbing light in an infrared/near infrared wavelength spectrum of light.

The lower electrodes 10B, 10G, 10R, and 10IR and the upper electrodes 20B, 20G, 20R, and 201R may be light-transmitting electrodes and may be made of, for example, a transparent conductor such as indium tin oxide (ITO), indium zinc oxide (IZO), zinc oxide (ZnO), tin oxide (SnO), aluminum tin oxide (AITO), and fluorine-doped tin oxide (FTO), or may be a metal thin layer having a thin thickness of several nanometers or several tens of nanometers or a metal thin layer having a thin thickness of several nanometers to several tens of nanometers doped with a metal oxide.

The photoactive layers 30B, 30G, 30R, and 301R may include a p-type semiconductor material and an n-type semiconductor material. The photoactive layer 30B of the blue photo-sensing device 100B may include a p-type semiconductor material selectively absorbing light in a blue wavelength spectrum of light and an n-type semiconductor material selectively absorbing light in a blue wavelength spectrum of light, the photoactive layer 30G of the green photo-sensing device 100G may include a p-type semiconductor material selectively absorbing light in a green wavelength spectrum of light and an n-type semiconductor material selectively absorbing light in a green wavelength spectrum of light, the photoactive layer 30R of the red photo-sensing device 100R may include a p-type semiconductor material selectively absorbing light in a red wavelength spectrum of light and an n-type semiconductor material selectively absorbing light in a red wavelength spectrum of light, and the photoactive layer 301R of the infrared/near infrared photo-sensing device 100IR may include a p-type semiconductor material selectively absorbing light in an infrared wavelength spectrum of light and an n-type semiconductor material selectively absorbing light in an infrared wavelength spectrum of light.

The photoactive layer 301R of the infrared/near infrared photo-sensing device 100IR uses the squarylium compound represented by Chemical Formula 1 as a p-type semiconductor material and sub-phthalocyanine or a sub-phthalocyanine derivative, fullerene or a fullerene derivative, thiophene or a thiophene derivative, or a combination thereof as an n-type semiconductor material. The fullerene may include C60, C70, C76, C78, C80, C82, C84, C90, C96, C240, C540, a mixture thereof, a fullerene nanotube, and the like. The fullerene derivative may refer to compounds of these fullerenes having a substituent attached thereto. The fullerene derivative may include a substituent such as alkyl group, aryl group, or a heterocyclic group. Examples of the aryl groups and heterocyclic groups may be are a benzene ring, a naphthalene ring, an anthracene ring, a phenanthrene ring, a fluorene ring, a triphenylene ring, a naphthacene ring, a biphenyl ring, a pyrrole ring, a furan ring, a thiophene ring, an imidazole ring, an oxazole ring, a thiazole ring, a pyridine ring, a pyrazine ring, a pyrimidine ring, a pyridazine ring, an indolizine ring, an indole ring, a benzofuran ring, a benzothiophene ring, an isobenzofuran ring, a benzimidazole ring, an imidazopyridine ring, a quinolizidine ring, a quinoline ring, a phthalazine ring, a naphthyridine ring, a quinoxaline ring, a quinoxazoline ring, an isoquinoline ring, a carbazole ring, a phenanthridine ring, an acridine ring, a phenanthroline ring, a thianthrene ring, a chromene ring, an xanthene ring, a phenoxathin ring, a phenothiazine ring, or a phenazine ring.

The infrared/near infrared photo-sensing device 100IR may selectively absorb light in an infrared ray (particularly, near infrared ray) region of greater than or equal to about 700 nm and less than or equal to about 1300 nm without absorption in a visible wavelength spectrum of light.

Figure 9:
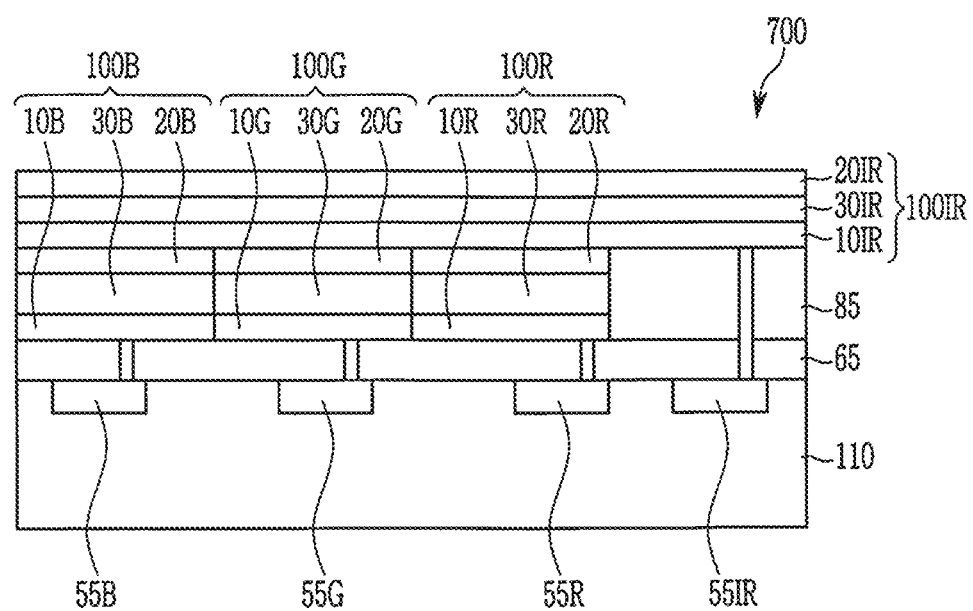
Figure 10:
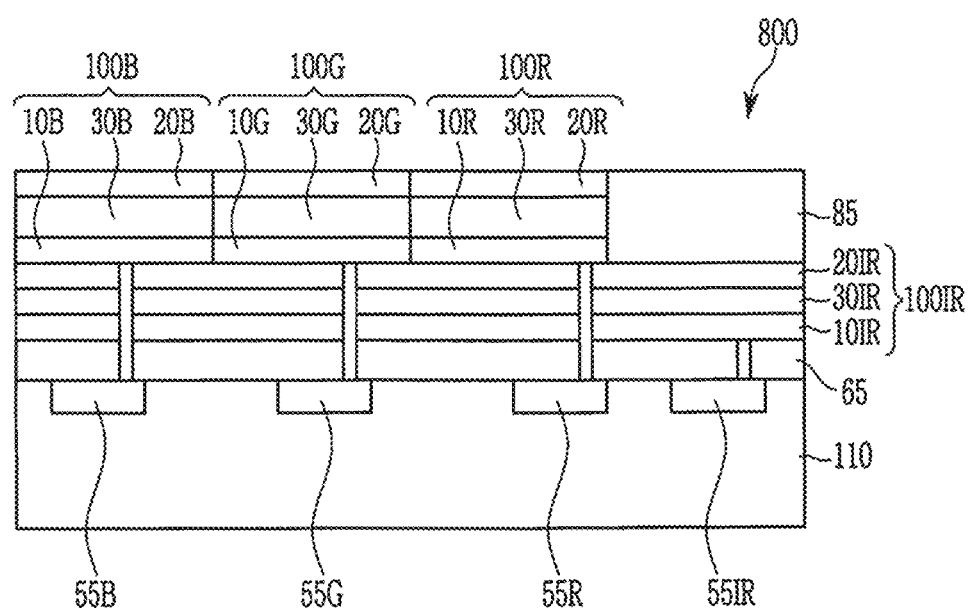

FIGS. 9 and 10 are schematic cross-sectional views of an image sensor according to some example embodiments.

Referring to FIG. 9, an image sensor 700 includes a semiconductor substrate 110 integrated with an infrared light/near infrared light charge storage 551R, a blue charge storage 55B, a green charge storage 55G, a red charge storage 55R, and a transmission transistor (not shown), a lower insulation layer 65, a blue photo-sensing device 100B, a green photo-sensing device 1000, a red photo-sensing device 100R, and an infrared/near infrared photo-sensing device 100IR. The infrared/near infrared photo-sensing device 100IR is formed on an entire surface of the blue photo-sensing device 100B, the green photo-sensing device 1000, and the red photo-sensing device 100R. Other structures are the same as the image sensor of FIG. 8.

In the structure of FIG. 9, the infrared/near infrared photo-sensing device 100IR may be disposed on the lower insulation layer 65 and the blue photo-sensing device 100B, the green photo-sensing device 1000, and the red photo-sensing device 100R may be disposed thereon. An image sensor having such a structure is shown in FIG. 10.

The infrared/near infrared photo-sensing device 100IR may selectively absorb light in an infrared ray (particularly, near infrared ray) region of greater than or equal to about 700 nm and less than or equal to about 1300 nm without absorption in a visible wavelength spectrum of light and may improve efficiency due to a large absorption area.

Figure 11:
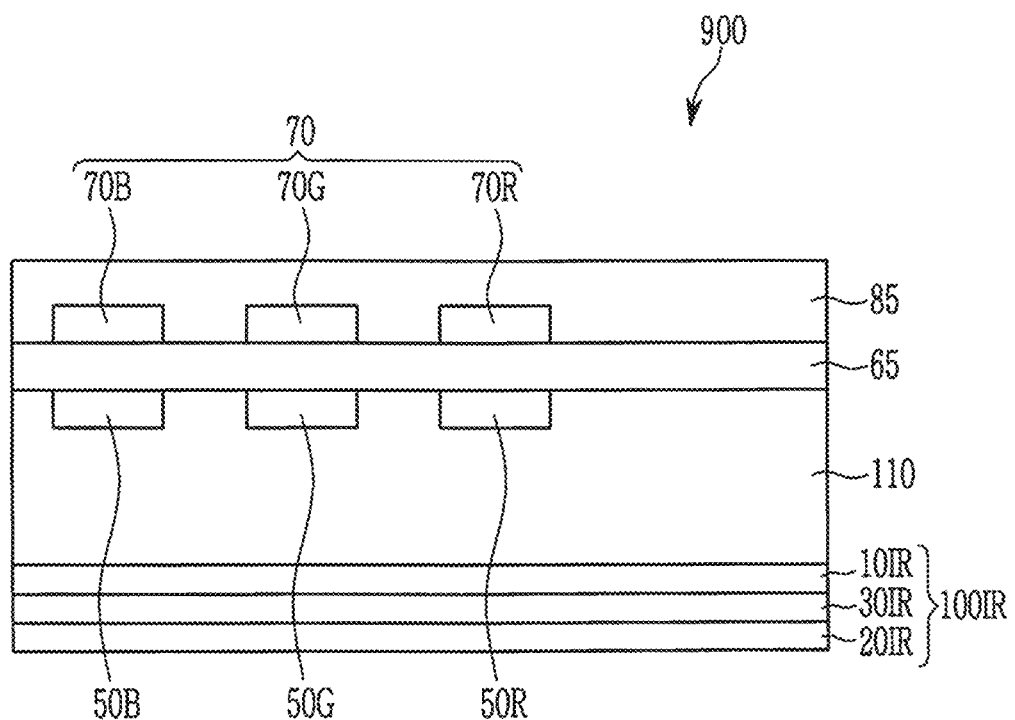

FIG. 11 is a schematic cross-sectional view of an image sensor according to some example embodiments.

Referring to FIG. 11, an image sensor 900 includes a semiconductor substrate 110 integrated with a blue charge storage 55B, a green charge storage 55G, a red charge storage 55R, and a transmission transistor (not shown); a lower insulation layer 65, a color filter layer (70) and a upper insulation layer 85 on the semiconductor substrate 110; and an infrared/near infrared photo-sensing device 100IR under the semiconductor substrate 110.

Figure 12:
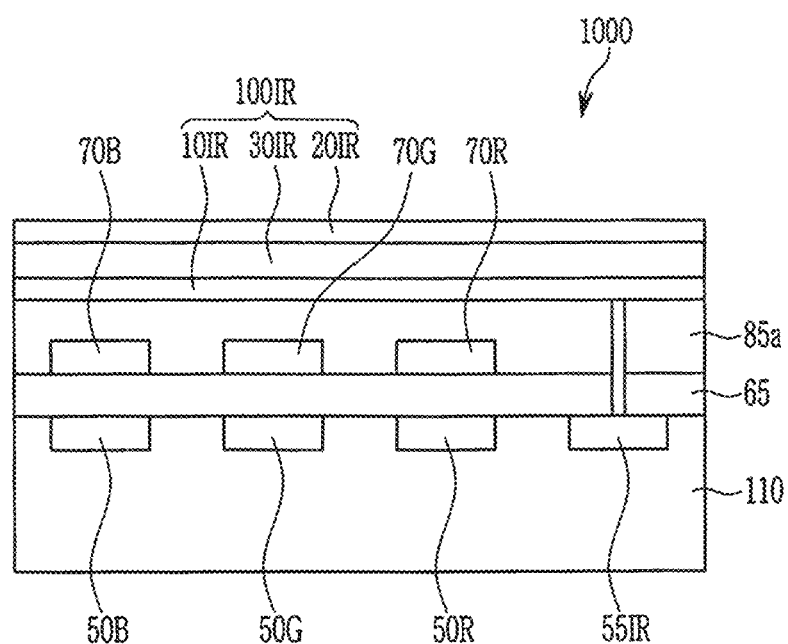

FIG. 12 is a schematic cross-sectional view of an image sensor according to some example embodiments.

Referring to FIG. 12, an image sensor 1000 includes a semiconductor substrate 110 integrated with a blue photodiode 50B, a red photodiode 50R, a green photodiode 50G, an infrared light/near infrared light charge storage 55IR, and a transmission transistor (not shown); a lower insulation layer 65; a blue filter 70B, a green filter 70G; a red filter 70R; a upper insulation layer 85a; and an infrared/near infrared photo-sensing device 100IR.

Figure 13:
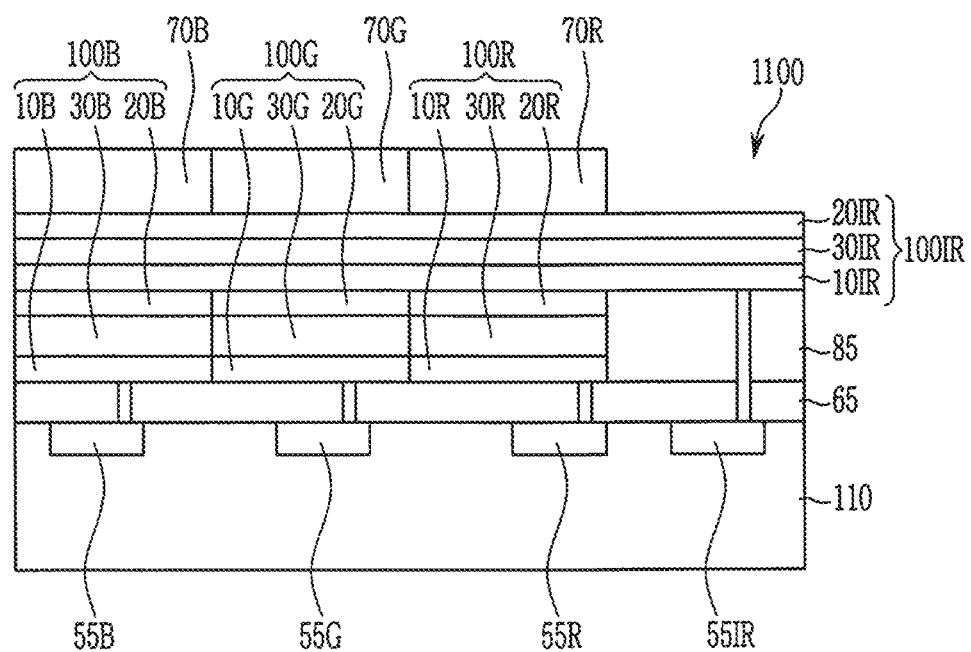

FIG. 13 is a schematic cross-sectional view of an image sensor according to some example embodiments.

Referring to FIG. 13, an image sensor 1100 includes a semiconductor substrate 110 integrated with an infrared light/near infrared light charge storage 551R, a blue storage 55B, a green storage 55G, a red storage 55R and a transmission transistor (not shown); a lower insulation layer 65; a blue photo-sensing device 100B, a green photo-sensing device 1000, a red photo-sensing device 100R, an infrared/near infrared photo-sensing device 100IR, a blue filter 70B, a green filter 70G, and a red filter 70R.

Figure 14:
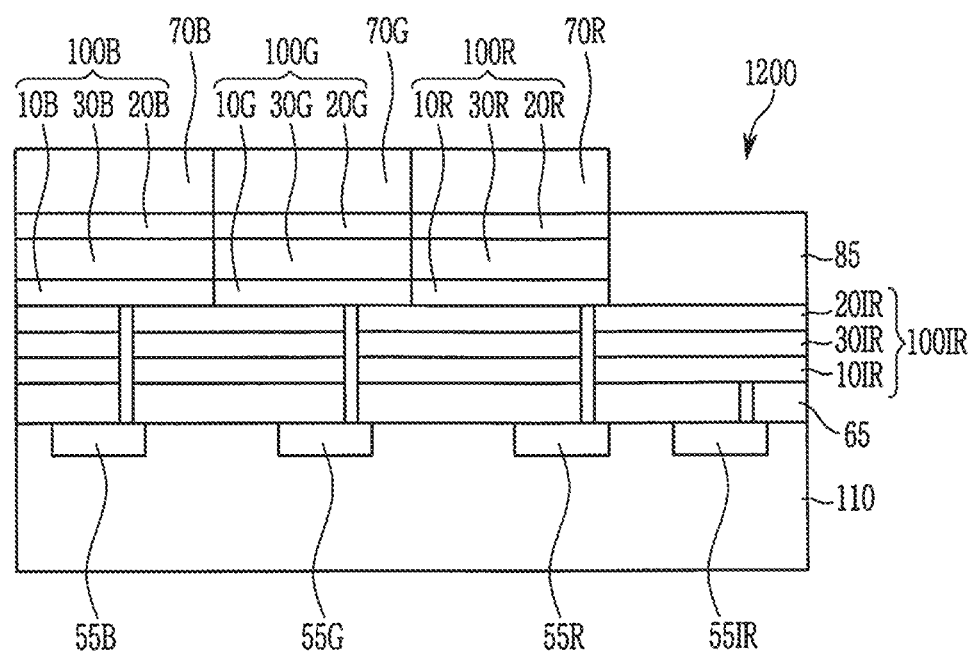

FIG. 14 is a schematic cross-sectional view of an image sensor according to some example embodiments.

Referring to FIG. 14, an image sensor 1200 includes a semiconductor substrate 110 integrated with an infrared light/near infrared light charge storage 551R, a blue storage 55B, a green storage 55G, a red storage 55R and a transmission transistor (not shown); a lower insulation layer 65; a blue photo-sensing device 100B, a green photo-sensing device 1000, a red photo-sensing device 100R, an infrared/near infrared photo-sensing device 100IR, a blue filter 70B, a green filter 70G, and a red filter 70R.

Figure 15:
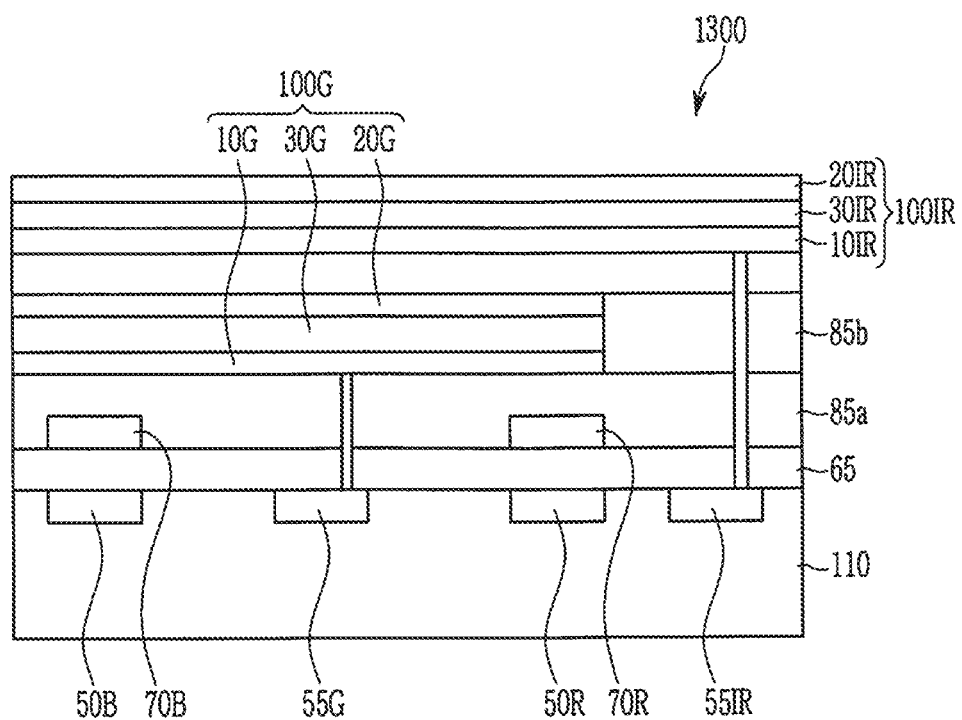

FIG. 15 is a schematic cross-sectional view of an image sensor according to some example embodiments.

Referring to FIG. 15, an image sensor 1300 includes a semiconductor substrate 110 integrated with an infrared light/near infrared light charge storage 551R, a blue storage 55B, a green storage 55G, a red storage 55R and a transmission transistor (not shown); a lower insulation layer 65; a blue filter 70B, a red filter 70R; a upper insulation layers 85a and 85b; a green photo-sensing device 1000; and an infrared/near infrared photo-sensing device 100IR.

Figure 16:
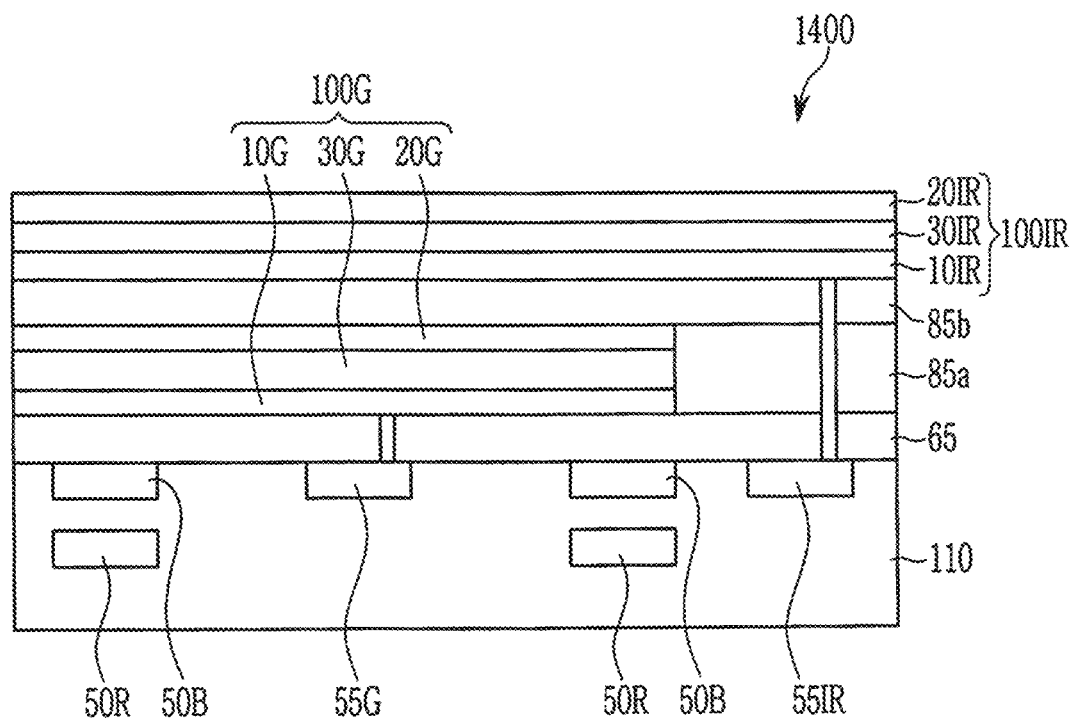

FIG. 16 is a schematic cross-sectional view of an image sensor according to some example embodiments.

In the image sensor 1400 of FIG. 16, the blue photodiode 50B and the red photodiode 50R are stacked perpendicularly, differing from the image sensor 1300 of FIG. 15.

Figure 17:
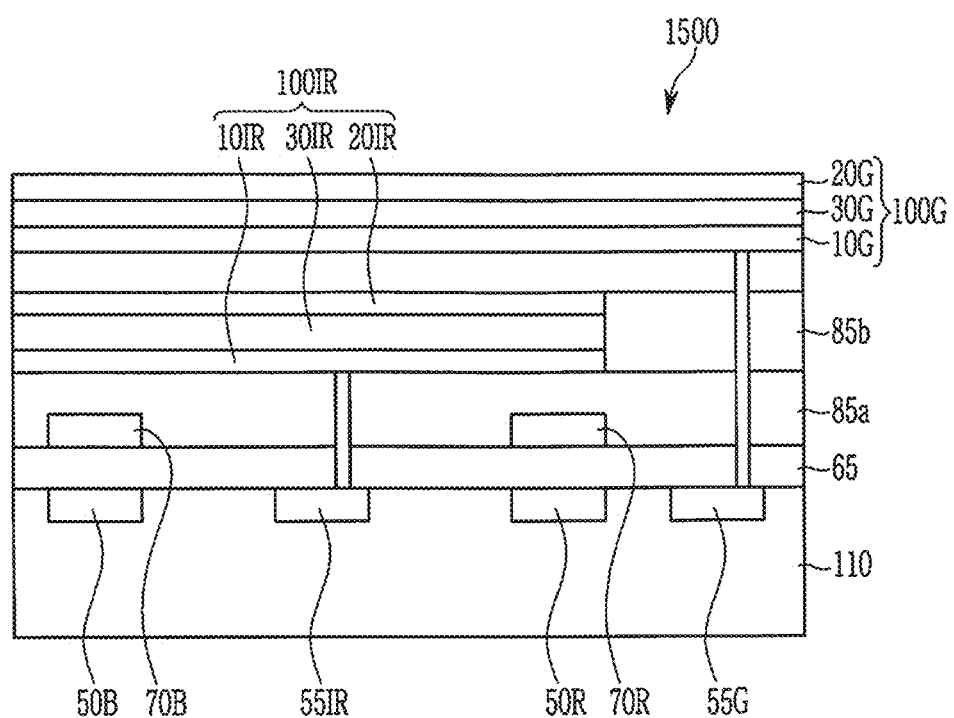

FIG. 17 is a schematic cross-sectional view of an image sensor according to some example embodiments.

Referring to FIG. 17, an image sensor 1500 includes a semiconductor substrate 110 integrated with an infrared light/near infrared light charge storage 551R, a blue storage 55B, a green storage 55G, a red storage 55R and a transmission transistor (not shown); a lower insulation layer 65; a blue filter 70B, a red filter 70R; a upper insulation layers 85a and 85b; an infrared/near infrared photo-sensing device 100IR; and a green photo-sensing device 100G.

Figure 18:
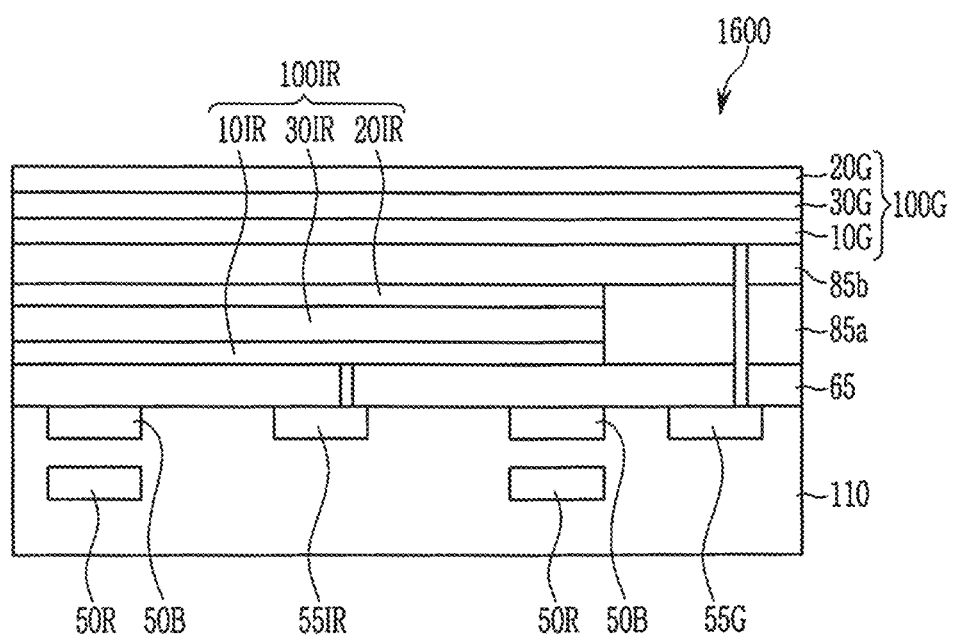

FIG. 18 is a schematic cross-sectional view of an image sensor according to some example embodiments.

In the image sensor 1600 of FIG. 18, the blue photodiode 50B and the red photodiode 50R are stacked perpendicularly, differing from the image sensor 1500 of FIG. 17.

The image sensor may be applied to various electronic devices, for example, a mobile phone, a digital camera, and the like but not limited thereto.

Figure 19:
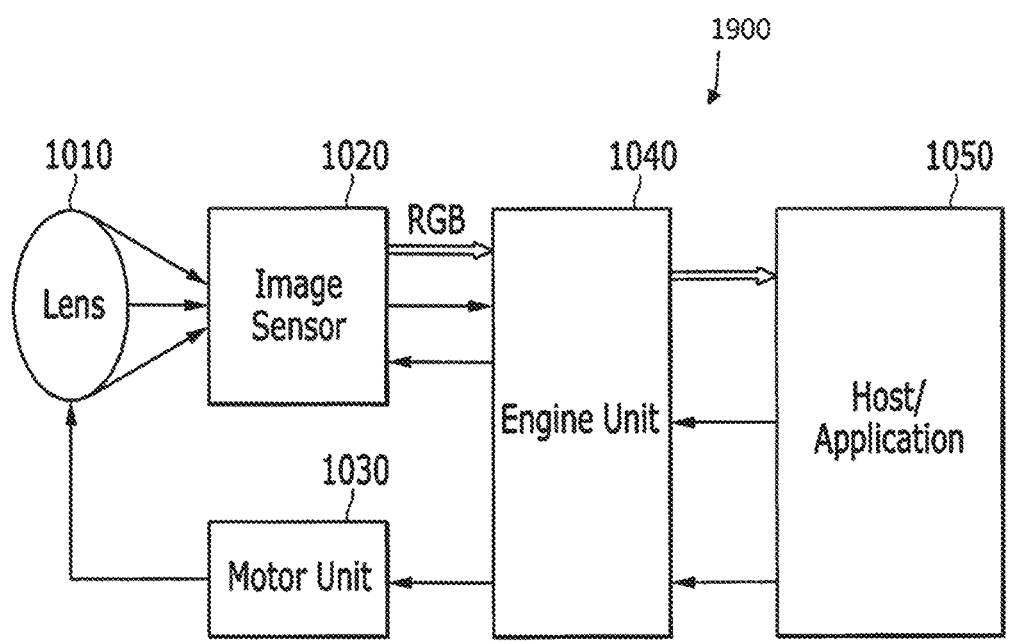
FIG. 19 is a block diagram of a digital camera including an image sensor according to some example embodiments.

FIG. 19 is a block diagram of a digital camera including an image sensor according to some example embodiments.

Referring to FIG. 19, a digital camera 1900 includes a lens 1010, an image sensor 1020, a motor unit 1030, and an engine unit 1040. The image sensor 1020 may be one of image sensors according to embodiments shown in FIGS. 2 to 18.

The lens 1010 concentrates incident light on the image sensor 1020. The image sensor 1020 generates RGB data for received light through the lens 1010.

In some embodiments, the image sensor 1020 may interface with the engine unit 1040.

The motor unit 1030 may adjust the focus of the lens 1010 or perform shuttering in response to a control signal received from the engine unit 1040. The engine unit 1040 may control the image sensor 1020 and the motor unit 1030.

The engine unit 1040 may be connected to a host/application 1050.

Hereinafter, some example embodiments are illustrated in more detail with reference to examples. However, it will be understood that these are examples, and the present disclosure is not limited thereto.

Synthesis Example I

Synthesis Example 1

[Reaction Scheme A]

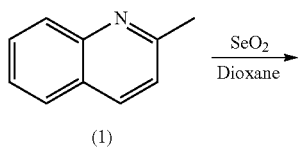

(1)

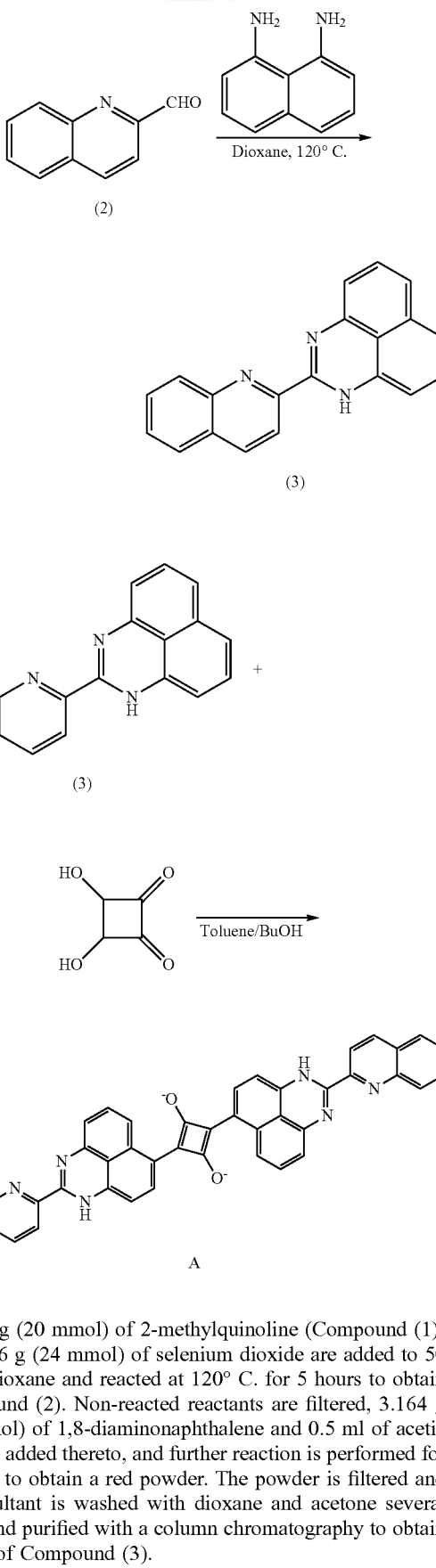

2.86 g (20 mmol) of 2-methylquinoline (Compound (1)) and 2.66 g (24 mmol) of selenium dioxide are added to 50 ml of dioxane and reacted at 120° C. for 5 hours to obtain Compound (2). Non-reacted reactants are filtered, 3.164 g (20 mmol) of 1,8-diaminonaphthalene and 0.5 ml of acetic acid are added thereto, and further reaction is performed for 3 hours to obtain a red powder. The powder is filtered and the resultant is washed with dioxane and acetone several times and purified with a column chromatography to obtain 99.5% of Compound (3).

1.16 g (5 mmol) of 3,4-dihydroxycyclobutane-1,2-dione (Compound (4)) and 2.95 g (10 mmol) of Compound (3) are reacted in 40 ml of a toluene/butanol (a volume ratio of 1:1) solution at 140° C. for 12 hours, and the obtained product is filtered and purified with a column chromatography to obtain final Compound A with a purity of 99.8%.

Figure 20:
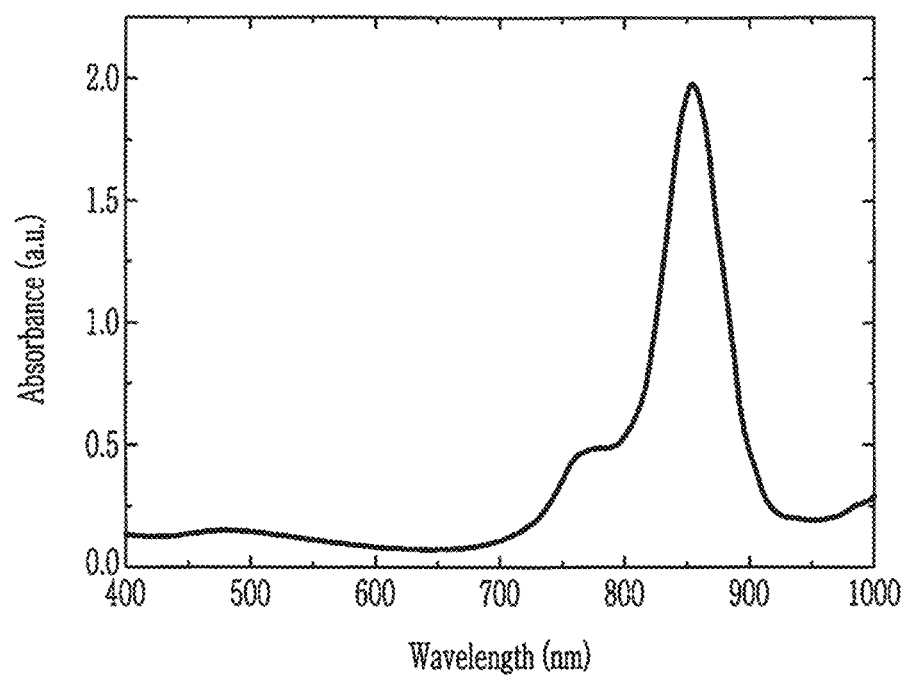
FIG. 20 is a graph showing absorbance depending on a wavelength of Compound A obtained in Synthesis Example 1.

Absorbance of Compound A of Synthesis Example 1 is measured and shown in FIG. 20.

FIG. 20 is a graph showing absorbance depending on a wavelength of Compound A obtained in Synthesis Example 1.

Referring to FIG. 20, Compound A has a maximum absorption wavelength at about 854 nm and high infrared light wavelength selectivity in about 850 nm to about 900 nm.

Synthesis Examples 2 to 15

Compounds B to O are synthesized by the same method as Synthesis Example 1 except for using each reactant of Table 1 instead of 2-methylquinoline.

TABLE 1

| Synthesis Example | Compound | Reactant | Final compounds |
|---|---|---|---|
| 1 | A | 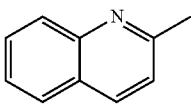 | 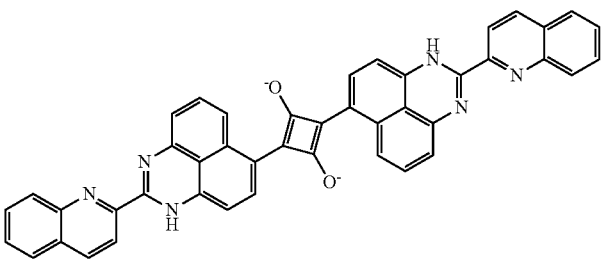 |
| 2 | B | 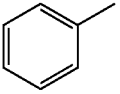 | 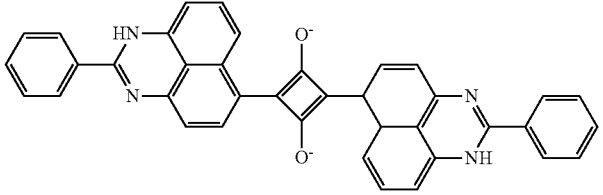 [SMILES: [O-]C1=C(c2ccc3c4c(cccc24)NC(c2ccccc2)=N3)C([O-])=C1C1C=CC2=C3C(=CC=CC31)NC(c1ccccc1)=N2] |
| 3 | C | 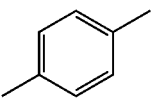 | 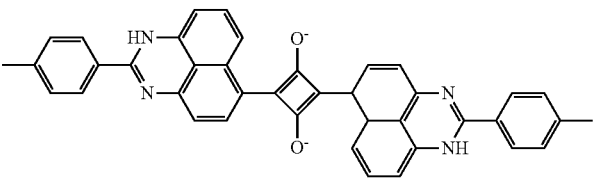 |
| 4 | D | 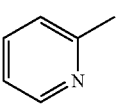 | 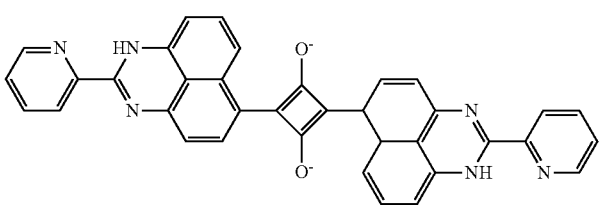 [SMILES: [O-]C1=C(c2ccc3c4c(cccc24)NC(c2ccccn2)=N3)C([O-])=C1C1C=CC2=C3C(=CC=CC31)NC(c1ccccn1)=N2] |
| 5 | E | 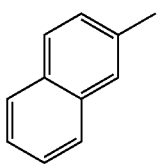 | 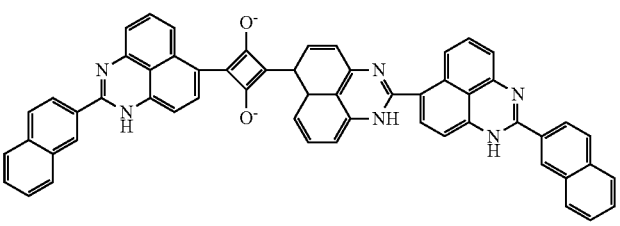 [SMILES: [O-]C1=C(c2ccc3c4c(cccc24)N=C(c2ccc4ccccc4c2)N3)C([O-])=C1C1C=CC2=C3C(=CC=CC31)NC(c1ccc3c4c(cccc14)N=C(c1ccc4ccccc4c1)N3)=N2] |

TABLE 1-continued
| Synthesis Example | Compound | Reactant | Final compounds |
|---|---|---|---|
| 6 | F | 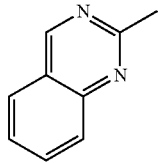 | 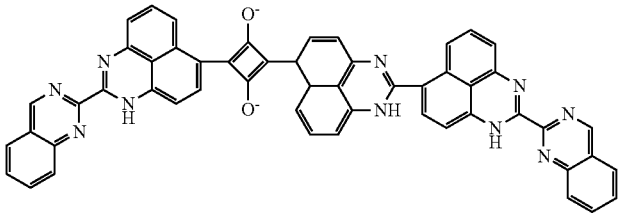 [SMILES: [O-]C1=C(c2ccc3c4c(cccc24)N=C(c2ncc4ccccc4n2)N3)C([O-])=C1C1C=CC2=C3C(=CC=CC31)NC(c1ccc3c4c(cccc14)N=C(c1ncc4ccccc4n1)N3)=N2] |
| 7 | G | 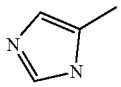 | 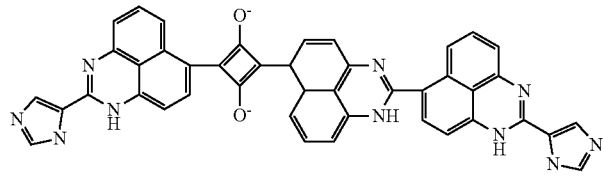 [SMILES: [O-]C1=C(c2ccc3c4c(cccc24)N=C(c2cnc[nH]2)N3)C([O-])=C1C1C=CC2=C3C(=CC=CC31)NC(c1ccc3c4c(cccc14)N=C(c1cnc[nH]1)N3)=N2] |
| 8 | H | 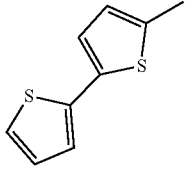 | 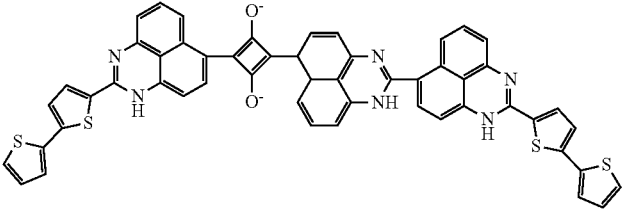 [SMILES: [O-]C1=C(c2ccc3c4c(cccc24)N=C(c2ccc(-c4cccs4)s2)N3)C([O-])=C1C1C=CC2=C3C(=CC=CC31)NC(c1ccc3c4c(cccc14)N=C(c1ccc(-c4cccs4)s1)N3)=N2] |
| 9 | I | 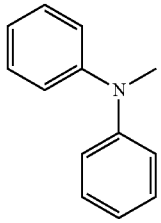 | 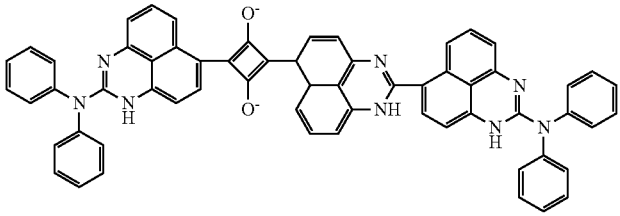 [SMILES: [O-]C1=C(c2ccc3c4c(cccc24)N=C(N(c2ccccc2)c2ccccc2)N3)C([O-])=C1C1C=CC2=C3C(=CC=CC31)NC(c1ccc3c4c(cccc14)N=C(N(c1ccccc1)c1ccccc1)N3)=N2] |
| 10 | J | 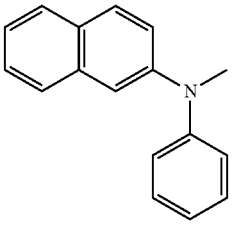 [SMILES: CN(c1ccccc1)c1ccc2ccccc2c1] | 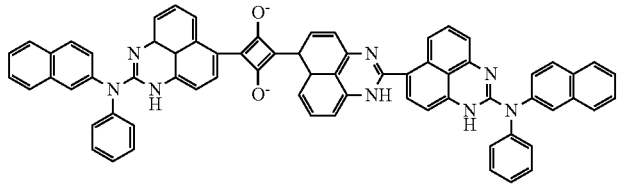 [SMILES: [O-]C1=C(C2=CC=C3NC(N(c4ccccc4)c4ccc5ccccc5c4)=NC4C=CC=C2C34)C([O-])=C1C1C=CC2=C3C(=CC=CC31)NC(c1ccc3c4c(cccc14)N=C(N(c1ccccc1)c1ccc4ccccc4c1)N3)=N2] |
| 11 | K | 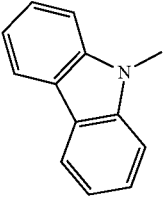 | 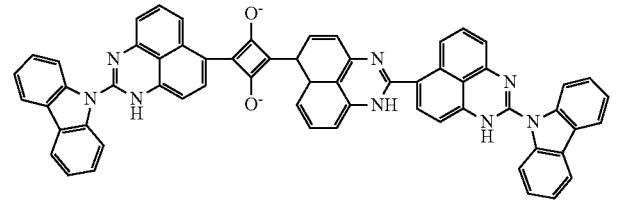 [SMILES: [O-]C1=C(c2ccc3c4c(cccc24)N=C(n2c4ccccc4c4ccccc42)N3)C([O-])=C1C1C=CC2=C3C(=CC=CC31)NC(c1ccc3c4c(cccc14)N=C(n1c4ccccc4c4ccccc41)N3)=N2] |
| 12 | L | 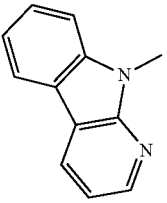 | 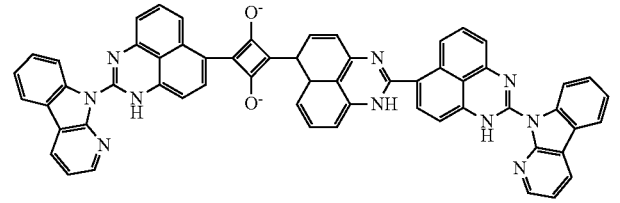 [SMILES: [O-]C1=C(c2ccc3c4c(cccc24)N=C(n2c4ccccc4c4cccnc42)N3)C([O-])=C1C1C=CC2=C3C(=CC=CC31)NC(c1ccc3c4c(cccc14)N=C(n1c4ccccc4c4cccnc41)N3)=N2] |

TABLE 1-continued

| Synthesis Example | Compound | Reactant | Final compounds |
|---|---|---|---|
| 13 | M | | |
| 14 | N | | |
| 15 | O | | |

Evaluation I

Maximum absorption wavelengths ($\lambda_{max}$) and extinction coefficients of Compounds A to O of Synthesis Examples 1 to 15 are measured. The maximum absorption wavelengths ($\lambda_{max}$) and absorbances are measured by dissolving each compound in dichloromethane to prepare a solution and measuring with a UV-Vis spectrometer.

The results are shown in Table 2.

TABLE 2

| Synthesis Examples | Compounds | $\lambda_{max}$ (nm) | $A_{NIR}/A_{VIS}$ |
|---|---|---|---|
| 1 | A | 854 | 22.22 |
| 2 | B | 757 | 16.03 |
| 3 | C | 768 | 38.46 |
| 4 | D | 757 | 17.86 |
| 5 | E | 758 | 526.31 |
| 6 | F | 781 | 28.57 |
| 7 | G | 914 | 21.74 |
| 8 | H | 778 | 11.36 |
| 9 | I | 807 | 12.35 |
| 10 | J | 715 | 43.48 |
| 11 | K | 720 | 17.54 |
| 12 | L | 726 | 9.09 |
| 13 | M | 715 | 41.67 |
| 14 | N | 763 | 73.72 |
| 15 | O | 712 | 62.5 |

* $A_{NIR}$: maximum absorption coefficient in an infrared ray (IR) region
* $A_{VIS}$: maximum absorption coefficient in a visible wavelength spectrum of light Referring to Table 2, compounds of Synthesis Examples 1 to 15 have a maximum absorption wavelength of greater than or equal to 700 nm and $A_{NIR}/A_{VIS}$ of greater than or equal to 8 which indicates high infrared light absorption selectivity.

Synthesis Example II

Synthesis Example 16

[Reaction Scheme B]

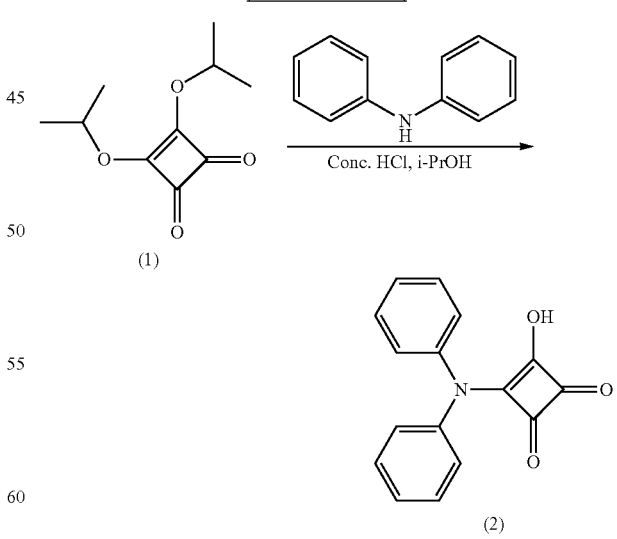

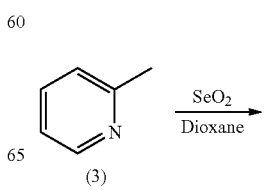

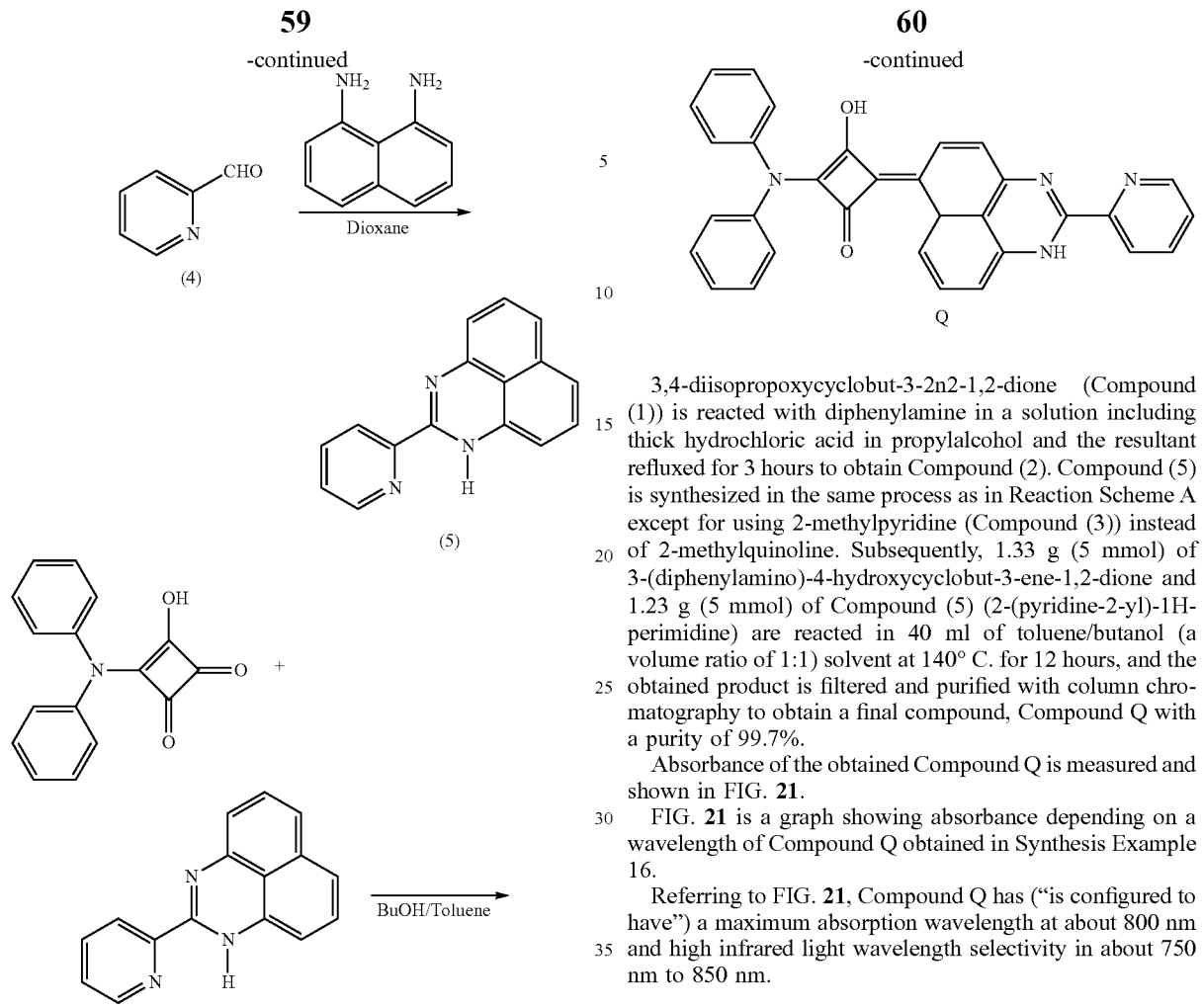

3,4-diisopropoxycyclobut-3-2n2-1,2-dione (Compound (1)) is reacted with diphenylamine in a solution including thick hydrochloric acid in propylalcohol and the resultant refluxed for 3 hours to obtain Compound (2). Compound (5) is synthesized in the same process as in Reaction Scheme A except for using 2-methylpyridine (Compound (3)) instead of 2-methylquinoline. Subsequently, 1.33 g (5 mmol) of 3-(diphenylamino)-4-hydroxycyclobut-3-ene-1,2-dione and 1.23 g (5 mmol) of Compound (5) (2-(pyridine-2-yl)-1H-perimidine) are reacted in 40 ml of toluene/butanol (a volume ratio of 1:1) solvent at 140° C. for 12 hours, and the obtained product is filtered and purified with column chromatography to obtain a final compound, Compound Q with a purity of 99.7%.

Figure 21:
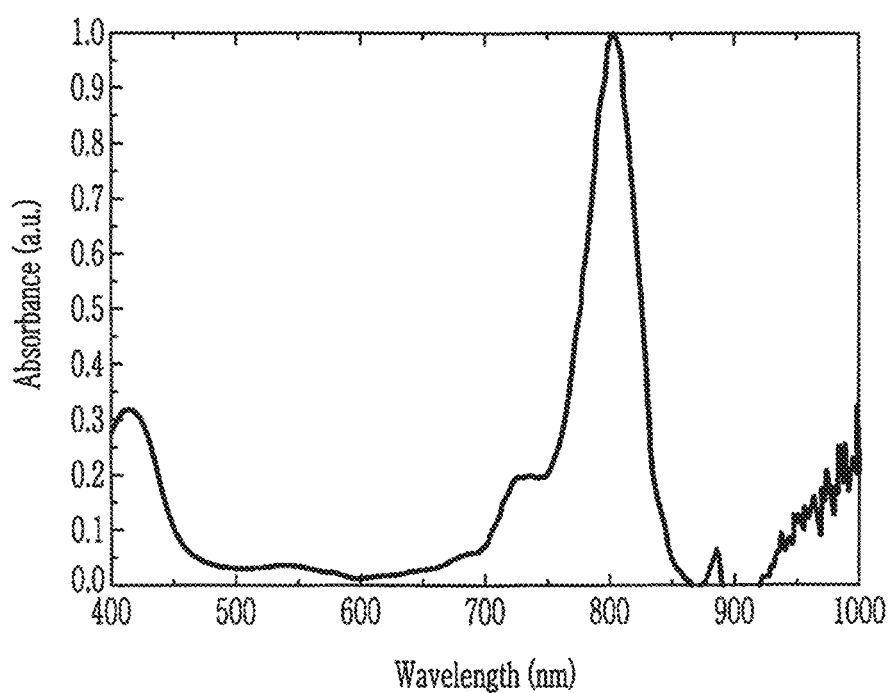
FIG. 21 is a graph showing absorbance depending on a wavelength of Compound Q obtained in Synthesis Example 16.

Absorbance of the obtained Compound Q is measured and shown in FIG. 21.

FIG. 21 is a graph showing absorbance depending on a wavelength of Compound Q obtained in Synthesis Example 16.

Referring to FIG. 21, Compound Q has ("is configured to have") a maximum absorption wavelength at about 800 nm and high infrared light wavelength selectivity in about 750 nm to 850 nm.

Synthesis Example 17

[Reaction Scheme C]

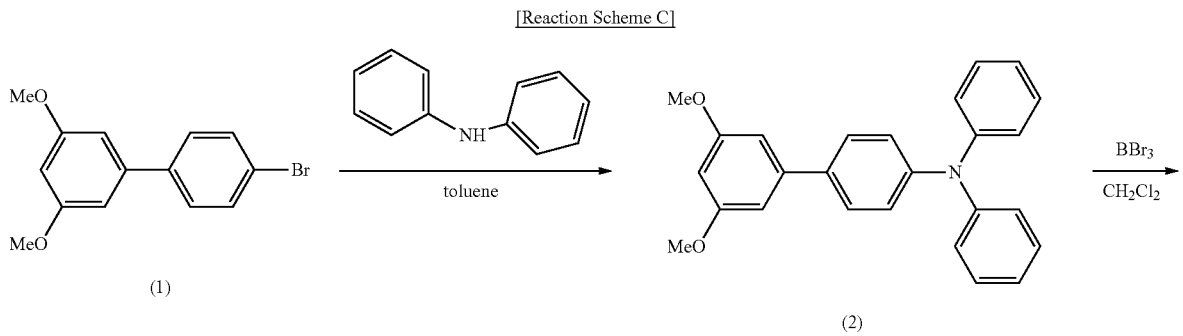

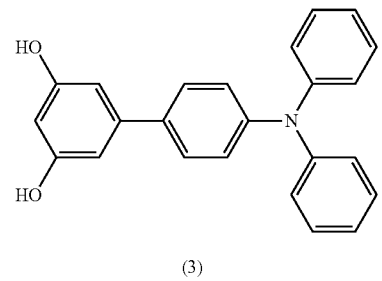

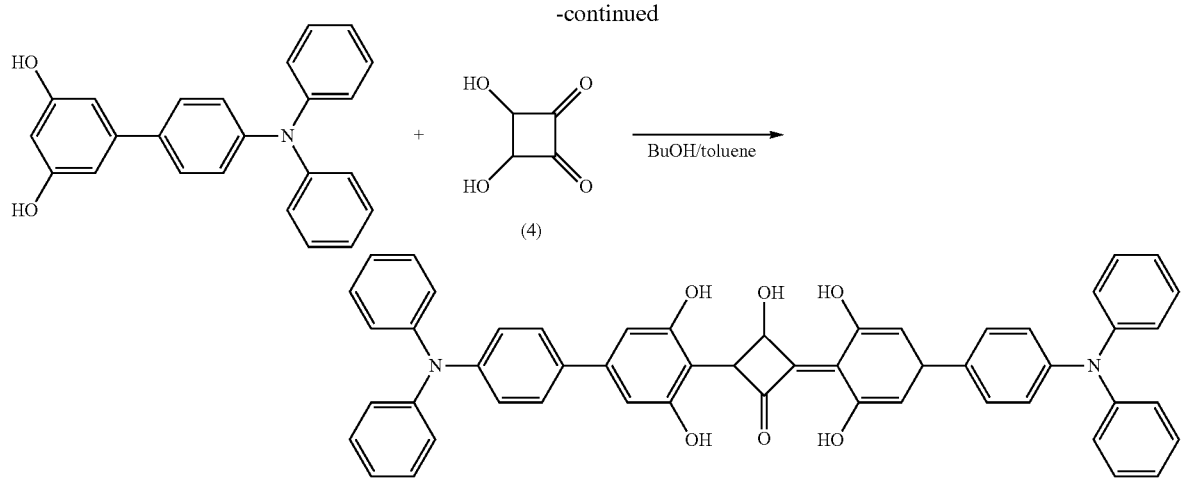

R

Compound (1) (4'-bromo-3,5-dimethoxy-1,1'-bipheny) and diphenylamine are reacted in 50 ml of toluene in the presence of a catalyst Pd$_2$(dba)$_3$ and t-BuONa at 120° C. for 8 hours to obtain Compound (2), and obtained Compound (2) is reacted with BBr$_3$ under CH$_2$Cl$_2$ to obtain Compound (3). Subsequently, 3.53 g (10 mmol) of Compound (3) and 580.35 mg (5 mmol) of Compound (4) are reacted in 40 ml of a toluene/butanol (a volume ratio of 1:1) solvent for 140° C. for 12 hours, and the obtained product is filtered and purified with a column chromatography to obtain a final compound, Compound R with a purity of 99.7%.

Figure 22:
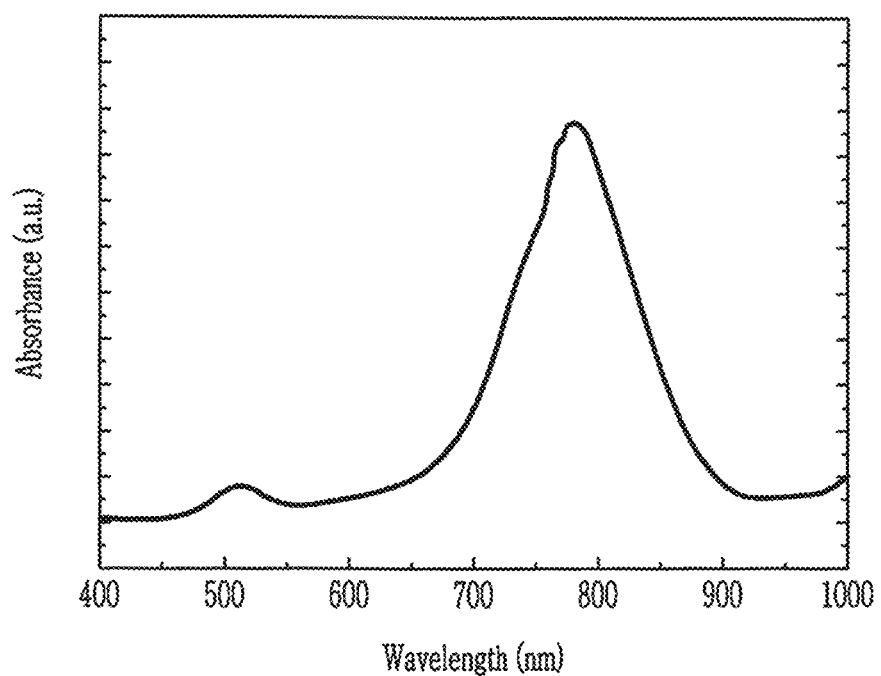
FIG. 22 is a graph showing absorbance depending on a wavelength of Compound R obtained in Synthesis Example 17.

Absorbance of Compound R is measured and shown in FIG. 22.

FIG. 22 is a graph showing absorbance depending on a wavelength of Compound R obtained in Synthesis Example 17.

Referring to FIG. 22, Compound R has a maximum absorption wavelength at about 800 nm and high infrared light wavelength selectivity in about 750 nm to 850 nm.

Comparative Synthesis Example 1

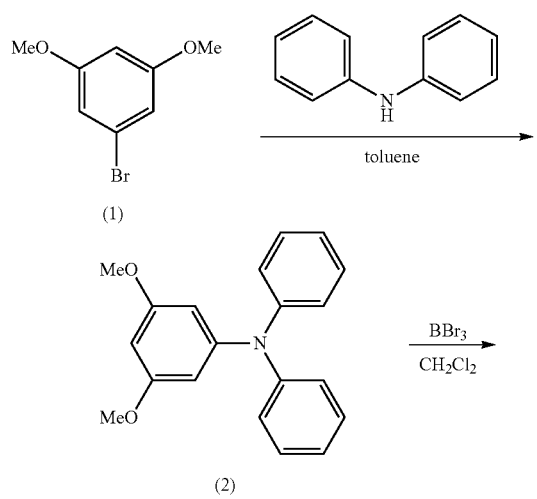

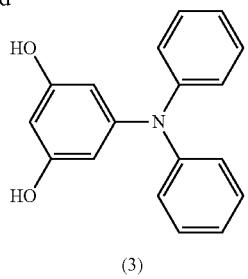

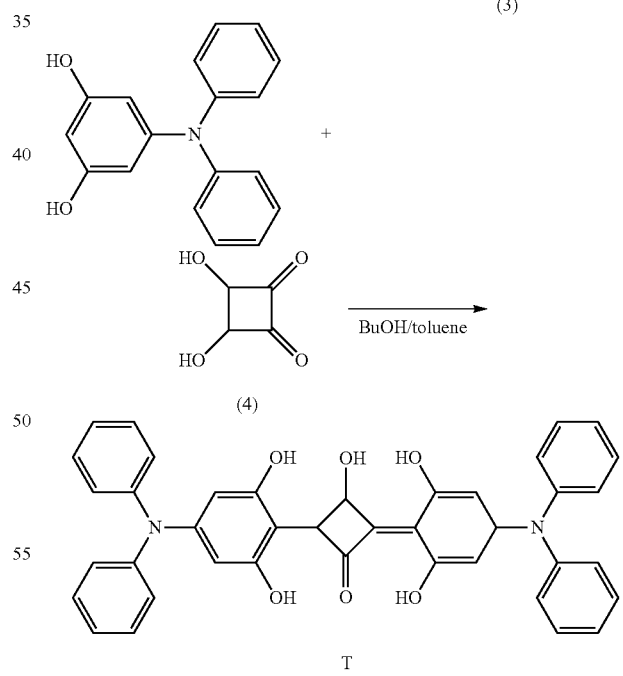

Compound (1) (1-bromo-3,5-dimethoxybenzene) and diphenylamine are reacted in 50 ml of toluene in the presence of a catalyst, Pd$_2$(dba)$_3$ and t-BuONa at 120° C. for 8 hours to obtain Compound (2), and obtained Compound (2) is reacted with BBr$_3$ under CH$_2$Cl$_2$ to obtain Compound (3). Subsequently, 2.77 g (10 mmol) of Compound (3) and 580.35 mg (5 mmol) of Compound (4) are reacted in 40 ml of toluene/butanol (a volume ratio of 1:1) solvent for 140° C. for 12 hours, and the obtained product is filtered and purified with a column chromatography to obtain a final compound, Compound T with a purity of 99.7%.

Figure 23:
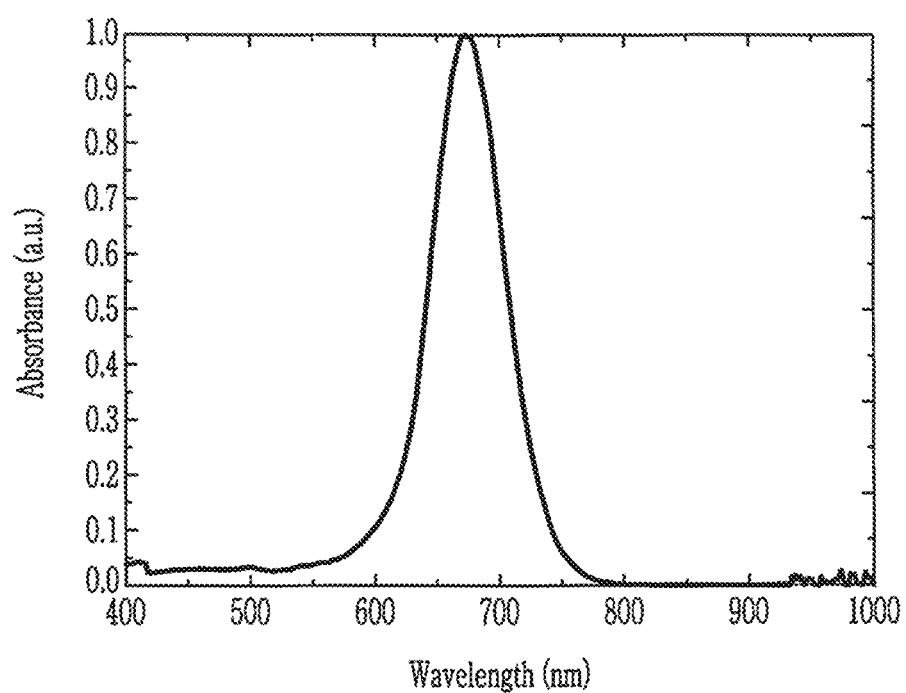
FIG. 23 is a graph showing absorbance depending on a wavelength of Compound T obtained in Comparative Synthesis Example 1.

Absorbance of the compound T obtained in Comparative Synthesis Example 1 is measured and shown in FIG. 23.

FIG. 23 is a graph showing absorbance depending on a wavelength of Compound T obtained in Comparative Synthesis Example 1.

Referring to FIG. 23, Compound T has a maximum absorption wavelength at about 650 nm and shows main absorption in a visible ray region.

Comparative Synthesis Example 2

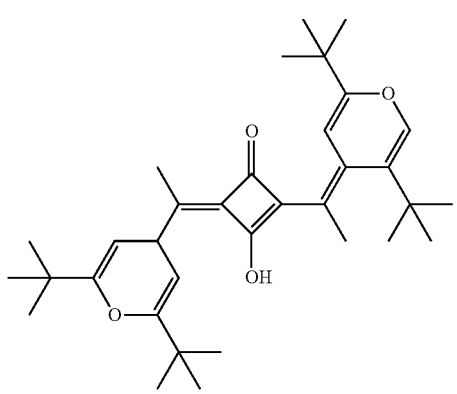

U

Figure 24:
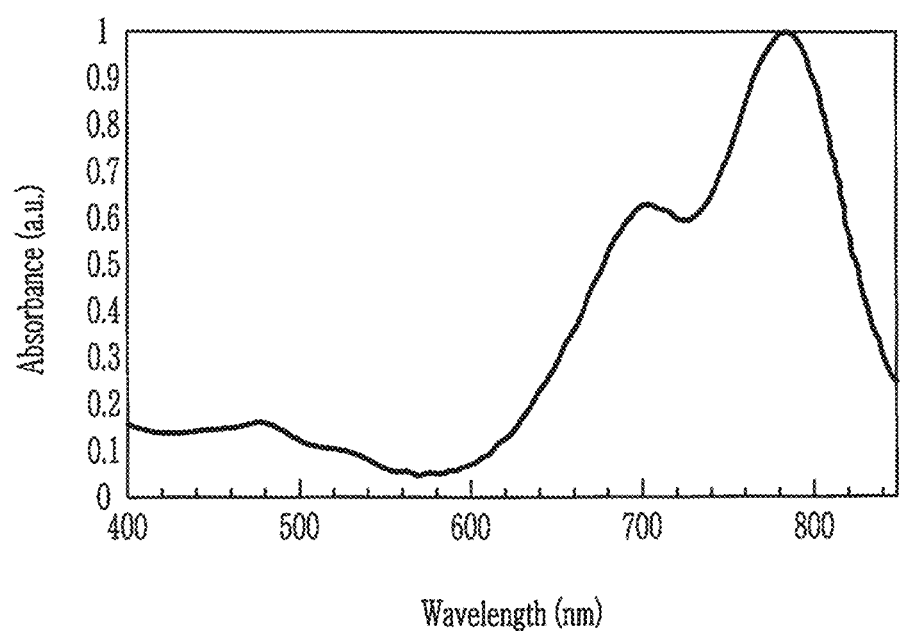
FIG. 24 is a graph showing absorbance depending on a wavelength of Compound U obtained in Comparative Synthesis Example 2.

Absorbance of Compound U is measured and shown in FIG. 24.

FIG. 24 is a graph showing absorbance depending on a wavelength of Compound U obtained in Comparative Synthesis Example 2.

Referring to FIG. 24, Compound U shows light absorption characteristics in a broad range of about 650 nm to 840 nm.

Comparative Synthesis Example 3

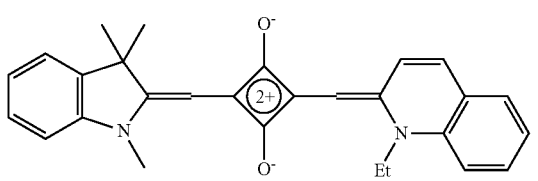

V

Figure 25:
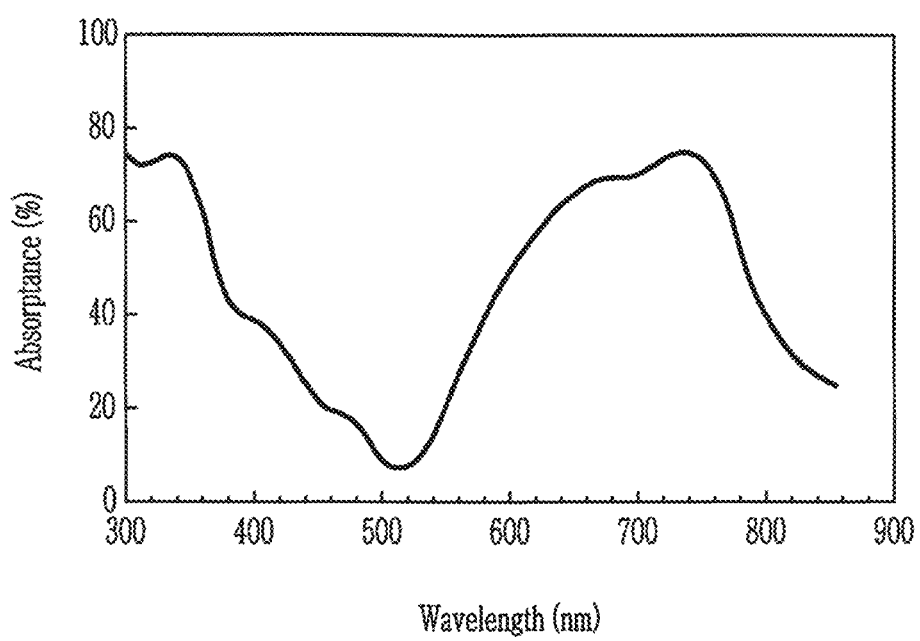
FIG. 25 is a graph showing absorbance depending on a wavelength of Compound V obtained in Comparative Synthesis Example 3.

Absorbance of Compound V disclosed in US 2008-0230123 A1 is shown in FIG. 25.

FIG. 25 is a graph showing absorbance depending on a wavelength of Compound V obtained in Comparative Synthesis Example 3.

Referring to FIG. 25, Compound V shows light absorption characteristics in broad ranges of about 300 nm to 450 nm and about 550 nm to 800 nm and low $A_{NIR}/A_{VIS}$ ratio of 0.65.

Comparative Synthesis Example 4

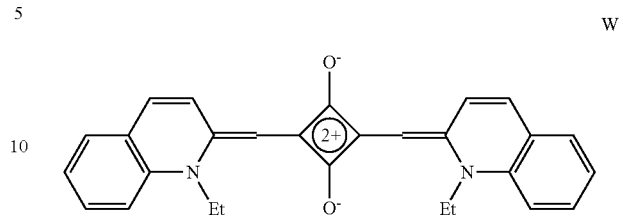

W

Figure 26:
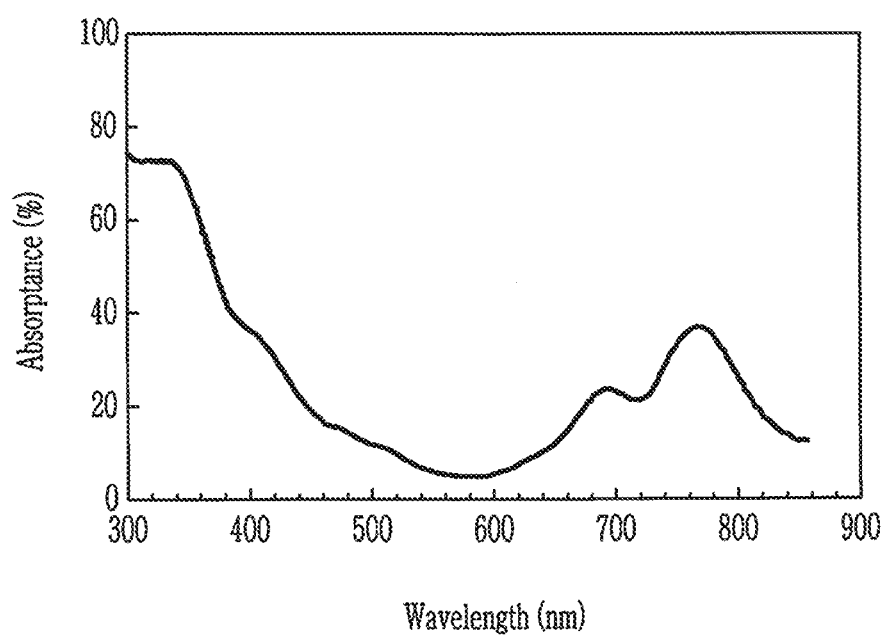
FIG. 26 is a graph showing absorbance depending on a wavelength of Compound W obtained in Comparative Synthesis Example 4.

Absorbance of Compound W disclosed in US 2008-0230123 A1 is shown in FIG. 26.

FIG. 26 is a graph showing absorbance depending on a wavelength of Compound W obtained in Comparative Synthesis Example 4.

Referring to FIG. 26, Compound W shows light absorption characteristics in broad ranges of about 300 nm to 450 nm and about 650 nm to 800 nm and low $A_{NIR}/A_{VIS}$ ratio.

While this disclosure has been described in connection with what is presently considered to be practical example embodiments, it is to be understood that the inventive concepts are not limited to the disclosed embodiments, but, on the contrary, is intended to cover various modifications and equivalent arrangements included within the spirit and scope of the appended claims.

What is claimed is:

1. An infrared cut filter comprising an infrared cut film, the infrared cut film comprising:

a squarylium compound represented by Chemical Formula 1:

[Chemical Formula 1]

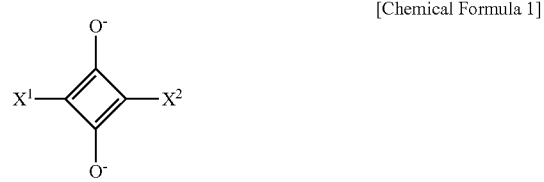

wherein, in Chemical Formula 1, $X^1$ and $X^2$ are each independently one of a functional group represented by Chemical Formula 1A, a functional group represented by Chemical Formula 1B, a functional group represented by Chemical Formula 1C, or a functional group represented by Chemical Formula 1D, at least one of $X^1$ and $X^2$ is the functional group represented by Chemical Formula 1A or the functional group represented by Chemical Formula 1B,

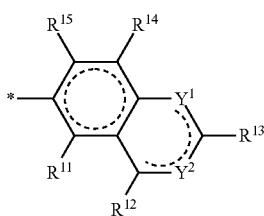

[Chemical Formula 1A]

wherein, in Chemical Formula 1A,
$Y^1$ and $Y^2$ are independently N or $NR^{16}$,
$R^{11}$ and $R^{12}$ are linked with each other to collectively comprise a fused ring with a quinazoline ring, or $R^{11}$ and $R^{12}$ are each independently one compound of a first set of compounds, the first set of compounds including
hydrogen,
a halogen,
a cyano group,
a nitro group,
a hydroxyl group,
a carboxyl group,
an ester group,
a substituted or unsubstituted C1 to C20 alkyl group,
a substituted or unsubstituted C1 to C20 alkoxy group,
a substituted or unsubstituted C6 to C30 aryl group,
a substituted or unsubstituted C3 to C20 cycloalkyl group,
a substituted or unsubstituted C3 to C20 heteroaryl group, and
a substituted or unsubstituted C2 to C20 heterocycloalkyl group,
$R^{13}$ is one compound of a second set of compounds, the second set of compounds including
a substituted or unsubstituted C6 to C30 aryl group,
a substituted or unsubstituted C3 to C20 heteroaryl group,
a substituted or unsubstituted C6 to C20 arylamine group, and
a substituted or unsubstituted C3 to C30 heteroarylamine group, and
$R^{14}$ and $R^{15}$ are linked with each other to collectively comprise a fused ring with a quinazoline ring, or $R^{14}$, $R^{15}$, and $R^{16}$ are independently one compound of the first set of compounds,

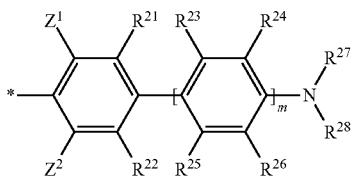

[Chemical Formula 1B]

wherein, in Chemical Formula 1B,
m is 1 or 2,
$Z^1$ and $Z^2$ are independently one of hydrogen or a hydroxyl group,
$R^{21}$ to $R^{26}$ are independently one compound of the first set of compounds, and
$R^{27}$ and $R^{28}$ are linked with each other to collectively comprise an N-containing aromatic ring group or an N-containing alicyclic cyclic group, or $R^{27}$ and $R^{28}$ are independently one compound of a third set of compounds, the third set of compounds including
a substituted or unsubstituted C1 to C20 alkyl group,
a substituted or unsubstituted C1 to C20 alkoxy group,
a substituted or unsubstituted C6 to C30 aryl group,
a substituted or unsubstituted C3 to C20 cycloalkyl group,
a substituted or unsubstituted C3 to C20 heteroaryl group, and
a substituted or unsubstituted C2 to C20 heterocycloalkyl group,

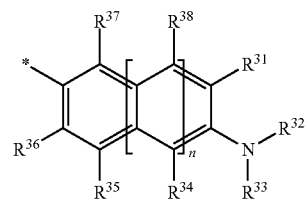

[Chemical Formula 1C]

wherein, in Chemical Formula 1C,
n is 1 or 2,
$R^{31}$ and $R^{32}$ are linked with each other to collectively comprise an aromatic ring group or an alicyclic cyclic group,
$R^{33}$ and $R^{34}$ are linked with each other to collectively comprise an aromatic ring group or an alicyclic cyclic group, and
$R^{35}$ to $R^{38}$ are independently one compound of the first set of compounds,

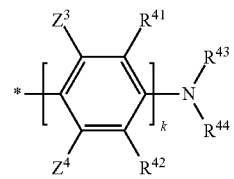

[Chemical Formula 1D]

wherein, in Chemical Formula 1D,
k is 0 or 1,
$Z^3$ and $Z^4$ are independently one of hydrogen or a hydroxyl group,
$R^{41}$ and $R^{42}$ are independently one compound of the first set of compounds, and
$R^{43}$ and $R^{44}$ are linked with each other to collectively comprise an N-containing aromatic ring group or an N-containing alicyclic cyclic group, or $R^{43}$ and $R^{44}$ are independently one of
a substituted or unsubstituted C1 to C20 alkyl group,
a substituted or unsubstituted C1 to C20 alkoxy group,
a substituted or unsubstituted C6 to C30 aryl group,
a substituted or unsubstituted C3 to C20 cycloalkyl group,
a substituted or unsubstituted C3 to C20 heteroaryl group, or a substituted or unsubstituted C2 to C20 heterocycloalkyl group,
wherein the substituted or unsubstituted C3 to C20 heteroaryl group in $R^{13}$ is one of
a substituted or unsubstituted pyridyl group,
a substituted or unsubstituted pyrazinyl group,
a substituted or unsubstituted pyrimidinyl group,
a substituted or unsubstituted pyridazinyl group,
a substituted or unsubstituted quinolyl group,
a substituted or unsubstituted isoquinolyl group,
a substituted or unsubstituted phthalazinyl group,
a substituted or unsubstituted quinazolinyl group,
a substituted or unsubstituted quinoxalinyl group,
a substituted or unsubstituted naphthyridinyl group,
a substituted or unsubstituted cinnolinyl group,
a substituted or unsubstituted pyrrolyl group,
a substituted or unsubstituted pyrazolyl group,
a substituted or unsubstituted imidazolyl group,
a substituted or unsubstituted triazolyl group,
a substituted or unsubstituted tetrazolyl group,
a substituted or unsubstituted thienyl group,
a substituted or unsubstituted thiazolyl group,
a substituted or unsubstituted oxazolyl group,
a substituted or unsubstituted indolyl group,
a substituted or unsubstituted isoindolyl group,
a substituted or unsubstituted indazolyl group,
a substituted or unsubstituted benzoimidazolyl group,
a substituted or unsubstituted benzotriazolyl group,
a substituted or unsubstituted benzothiazolyl group,
a substituted or unsubstituted benzooxazolyl group,
a substituted or unsubstituted carbazole group,
a substituted or unsubstituted phenazinyl group, or
a substituted or unsubstituted acridinyl group.

2. The infrared cut filter of claim 1, wherein $R^{11}$ and $R^{12}$ of Chemical Formula 1A are linked with each other, such that
$R^{11}$ and $R^{12}$ collectively comprise a C6 or C7 aromatic ring fused with a quinazoline ring and
the C6 or C7 aromatic ring does not include a heteroatom.

3. The infrared cut filter of claim 1, wherein the functional group represented by Chemical Formula 1A is a functional group represented by Chemical Formula 1A-1:

[Chemical Formula 1A-1]

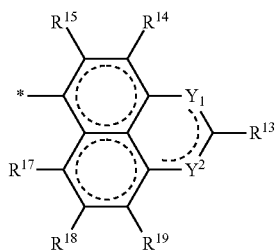

wherein, in Chemical Formula 1A-1,
$Y^1$ and $Y^2$ are independently one of N or $NR^{16}$, wherein $R^{16}$ is one of
hydrogen or
a substituted or unsubstituted C1 to C6 alkyl group,
$R^{17}$, $R^{18}$, and $R^{19}$ are independently one compound of the first set of compounds,
$R^{13}$ is one compound of the second set of compounds, and
$R^{14}$ and $R^{15}$ are linked with each other to collectively comprise a ring fused with a quinazoline ring, or $R^{14}$ and $R^{15}$ are independently one compound of the first set of compounds.

4. The infrared cut filter of claim 1, wherein $R^{13}$ of Chemical Formula 1A is one of
a substituted or unsubstituted phenyl group,
a substituted or unsubstituted naphthyl group,
a substituted or unsubstituted anthracenyl group,
a substituted or unsubstituted phenanthrenyl group,
a substituted or unsubstituted pyrenyl group,
a substituted or unsubstituted chrysenyl group,
a substituted or unsubstituted fluorenyl group, or
a substituted or unsubstituted perylenyl group.

5. The infrared cut filter of claim 1, wherein $R^{13}$ of Chemical Formula 1A is one functional group of a plurality of functional groups represented by Chemical Formula 2:

[Chemical Formula 2]

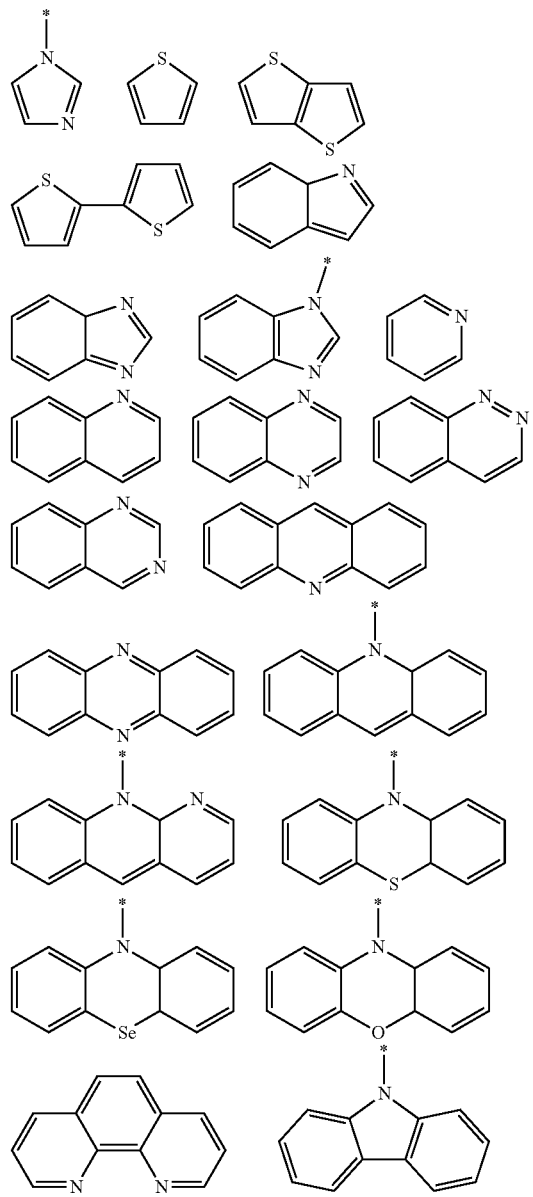

-continued

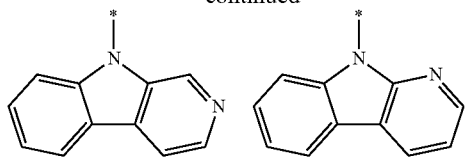

wherein, in Chemical Formula 2,
each position of a plurality of aromatic rings of the plurality of functional groups that is not indicated by an asterisk (*) is a binding position at $R^{13}$ of Chemical Formula 1A.

6. The infrared cut filter of claim 1, wherein $R^{13}$ of Chemical Formula 1A one of
a substituted or unsubstituted pyrrolidinyl group,
a substituted or unsubstituted piperidinyl group,
a substituted or unsubstituted piperazinyl group,
a substituted or unsubstituted morpholinyl group,
a substituted or unsubstituted thiomorpholinyl group,
a substituted or unsubstituted tetrahydropyridyl group,
a substituted or unsubstituted tetrahydroquinolinyl group,
a substituted or unsubstituted tetrahydroisoquinolinyl group,
a substituted or unsubstituted tetrahydrofuryl group,
a substituted or unsubstituted tetrahydropyranyl group,
a substituted or unsubstituted dihydrobenzofuranyl group,
a substituted or unsubstituted indolinyl group,
a substituted or unsubstituted isoindolinyl group, or
a substituted or unsubstituted tetrahydrocarbazolyl group.

7. The infrared cut filter of claim 1, wherein, in Chemical Formula 1A,
$R^{13}$ is one of the substituted or unsubstituted C6 to C20 arylamine group or the substituted or unsubstituted C3 to C30 heteroarylamine group, and
the substituted or unsubstituted C6 to C20 arylamine group or the substituted or unsubstituted C3 to C30 heteroarylamine group is represented by —$NR^xR^y$ wherein $R^x$ and $R^y$ are independently one of a substituted or unsubstituted C6 to C30 aryl group or a substituted or unsubstituted C3 to C20 heteroaryl group.

8. The infrared cut filter of claim 1, wherein Chemical Formula 1B one functional group of a plurality of functional groups represented by Chemical Formula 1B-1, Chemical Formula 1B-2, and Chemical Formula 1B-3:

[Chemical Formula 1B-1]

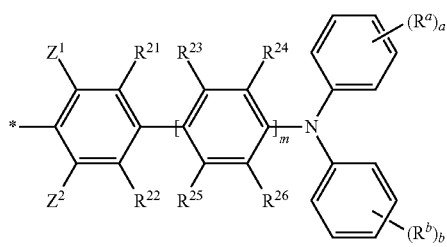

wherein, in Chemical Formula 1B-1,
m is 1 or 2,
$Z^1$ and $Z^2$ are independently hydrogen or a hydroxyl group,
$R^{21}$ to $R^{26}$ are independently one compound of the first set of compounds,
$R^a$ and $R^b$ are independently one compound of the first set of compounds, and
a and b are independently an integer that is inclusively between 0 to 5,

[Chemical Formula 1B-2]

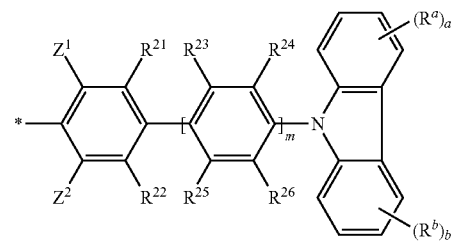

wherein, in Chemical Formula 1B-2,
m is 1 or 2,
$Z^1$ and $Z^2$ are independently one of hydrogen or a hydroxyl group,
$R^{21}$ to $R^{26}$ are independently one compound of the first set of compounds,
$R^a$ and $R^b$ are independently one compound of the first set of compounds, and
a and b are independently an integer that is inclusively between 0 to 4,

[Chemical Formula 1B-3]

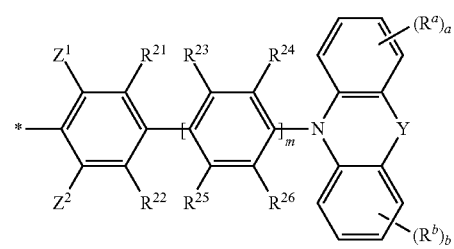

wherein, in Chemical Formula 1B-3,
m is 1 or 2,
$Z^1$ and $Z^2$ are independently one of hydrogen or a hydroxyl group,
$R^{21}$ to $R^{26}$ are independently one compound of the first set of compounds,
$R^a$ and $R^b$ are independently one compound of the first set of compounds,
Y is one of $NR^c$, O, S, Se, or Te, wherein $R^c$ is one of hydrogen or a substituted or unsubstituted C1 to C6 alkyl group, and
a and b are independently an integer that is inclusively between 0 to 4.

9. The infrared cut filter of claim 1, wherein Chemical Formula 1C is one functional group of a plurality of functional groups represented by Chemical Formula 1C-1 and Chemical Formula 1C-2:

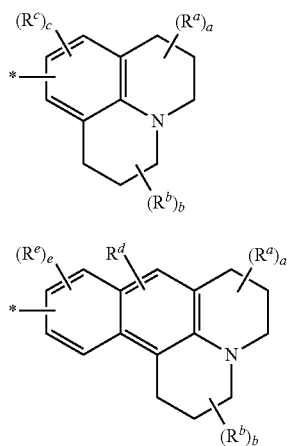

[Chemical Formula 1C-1]

[Chemical Formula 1C-2]

wherein, in Chemical Formula 1C-1 and Chemical Formula 1C-2,
$R^a$, $R^b$, $R^c$, and $R^d$ are independently one compound of the first set of compounds,
a and b are independently an integer that is inclusively between 0 to 6,
c is an integer that is inclusively between 0 to 2, and
e is an integer that is inclusively between 0 to 3.

10. The infrared cut filter of claim 1, wherein Chemical Formula 1D is one functional group of a plurality of functional groups represented by Chemical Formula 1D-1, Chemical Formula 1D-2, and Chemical Formula 1D-3:

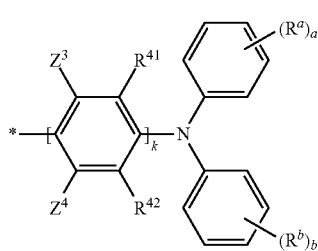

[Chemical Formula 1D-1]

wherein, in Chemical Formula 1D-1,
k is 0 or 1,
$Z^3$ and $Z^4$ are independently one of hydrogen or a hydroxyl group, $R^{41}$ and $R^{42}$ are independently one compound of the first set of compounds,
$R^a$ and $R^b$ are independently one compound of the first set of compounds, and
a and b are independently an integer that is inclusively between 0 to 5;

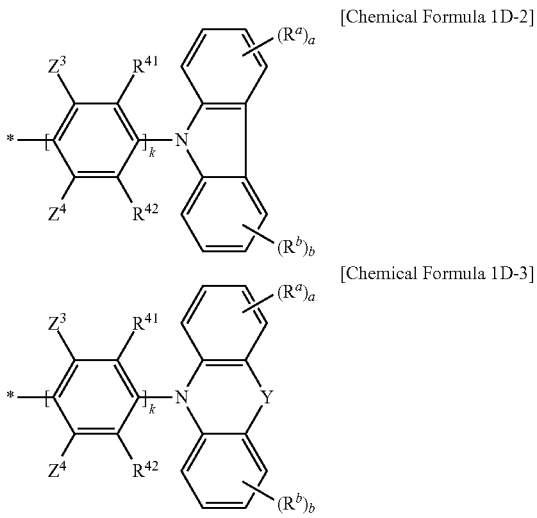

[Chemical Formula 1D-2]

[Chemical Formula 1D-3]

wherein, in Chemical Formula 1D-2 and Chemical Formula 1D-3,
k is 0 or 1,
$Z^3$ and $Z^4$ are independently one of hydrogen or a hydroxyl group,
$R^{41}$ and $R^{42}$ are independently one compound of the first set of compounds,
$R^a$ and $R^b$ are independently one compound of the first set of compounds,
Y is one of $NR^c$, O, S, Se, or Te, wherein $R^c$ is one of hydrogen or a substituted or unsubstituted C1 to C6 alkyl group, and
a and b are independently an integer that is inclusively between 0 to 4.

11. The infrared cut filter of claim 1, wherein the squarylium compound is a particular compound represented by one chemical formula of Chemical Formula 4-1, Chemical Formula 4-2, Chemical Formula 4-3, Chemical Formula 4-4, Chemical Formula 4-5, Chemical Formula 4-6, Chemical Formula 4-7, Chemical Formula 4-8, Chemical Formula 4-9, and Chemical Formula 4-10:

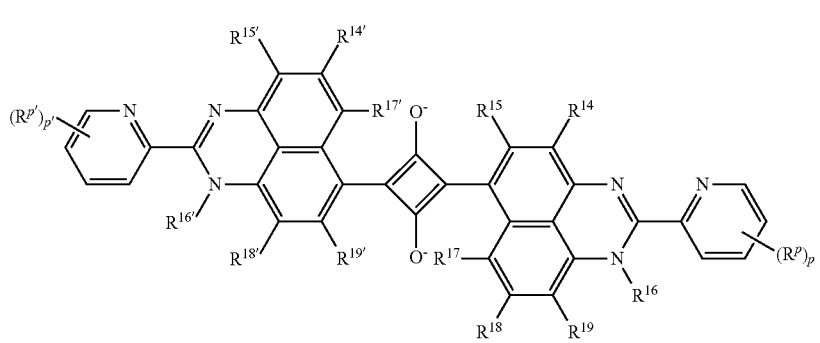

[Chemical Formula 4-1]

wherein, in Chemical Formula 4-1,
   $R^{14}$, $R^{15}$, $R^{16}$, $R^{17}$, $R^{18}$, $R^{19}$, $R^{14'}$, $R^{15'}$, $R^{16'}$, $R^{17'}$, $R^{18'}$, $R^{19'}$, $R^p$, and $R^{p'}$ are independently one compound of the first set of compounds, and
   p and p' are independently an integer that is inclusively between 0 to 4,

[Chemical Formula 4-2]

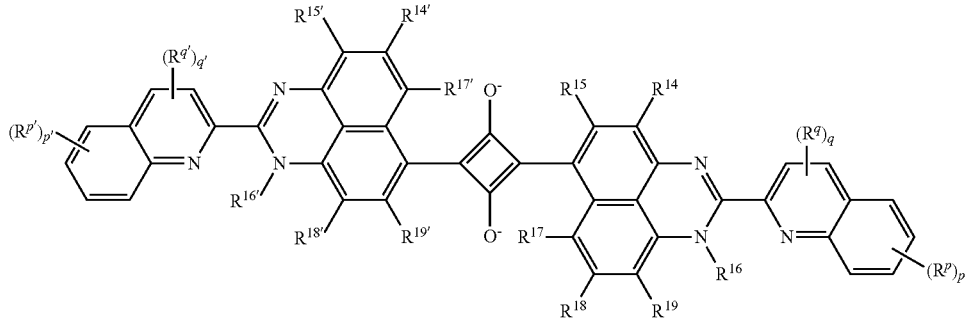

wherein, in Chemical Formula 4-2,
   $R^{14}$, $R^{15}$, $R^{16}$, $R^{17}$, $R^{18}$, $R^{19}$, $R^{14'}$, $R^{15'}$, $R^{16'}$, $R^{17'}$, $R^{18'}$, $R^{19'}$, $R^p$, $R^{p'}$, $R^q$, and $R^{q'}$ are independently one compound of the first set of compounds,
   p and p' are independently an integer that is inclusively between 0 to 4, and
   q and q' are independently an integer that is inclusively between 0 to 2,

[Chemical Formula 4-3]

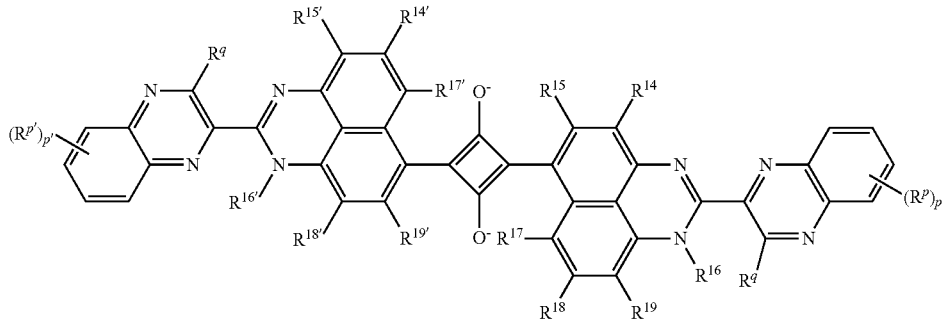

wherein, in Chemical Formula 4-3,
   $R^{14}$, $R^{15}$, $R^{16}$, $R^{17}$, $R^{18}$, $R^{19}$, $R^{14'}$, $R^{15'}$, $R^{16'}$, $R^{17'}$, $R^{18'}$, $R^{19'}$, $R^p$, $R^{p'}$, $R^q$, and $R^{q'}$ are independently one compound of the first set of compounds, and
   p and p' are independently an integer that is inclusively between 0 to 4,

[Chemical Formula 4-4]

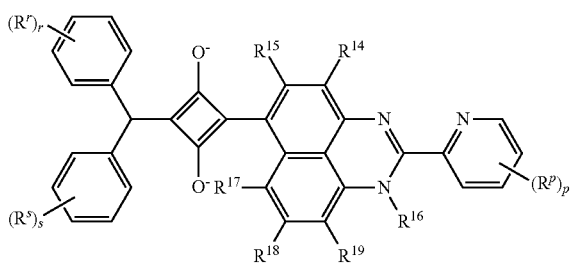

wherein, in Chemical Formula 4-4, $R^{14}$, $R^{15}$, $R^{16}$, $R^{17}$, $R^{18}$, $R^{19}$, $R^p$, $R^r$, and $R^s$ are independently one compound of the first set of compounds,
p is an integer that is inclusively between 0 to 4, and
r and s are independently an integer that is inclusively between 0 to 5,

[Chemical Formula 4-5]

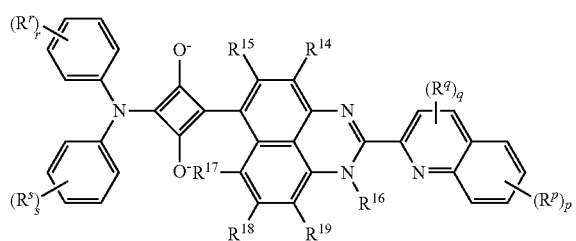

wherein, in Chemical Formula 4-5, $R^{14}$, $R^{15}$, $R^{16}$, $R^{17}$, $R^{18}$, $R^{19}$, $R^p$, $R^q$, $R^r$, and $R^s$ are independently one compound of the first set of compounds, p is an integer that is inclusively between 0 to 4, q is an integer that is inclusively between 0 to 2, and r and s are independently an integer that is inclusively between 0 to 5,

[Chemical Formula 4-6]

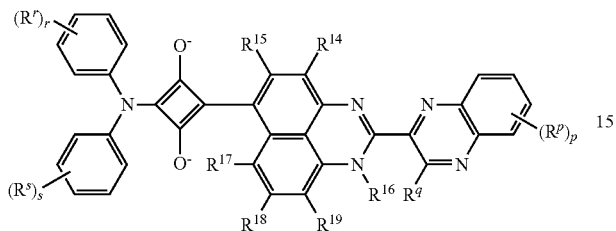

wherein, in Chemical Formula 4-6,
$R^{14}$, $R^{15}$, $R^{16}$, $R^{17}$, $R^{18}$, $R^{19}$, $R^p$, $R^q$, $R^r$, and $R^s$ are independently one compound of the first set of compounds, p is an integer that is inclusively between 0 to 4, q is an integer that is inclusively between 0 to 2, and r and s are independently an integer that is inclusively between 0 to 5,

[Chemical Formula 4-7]

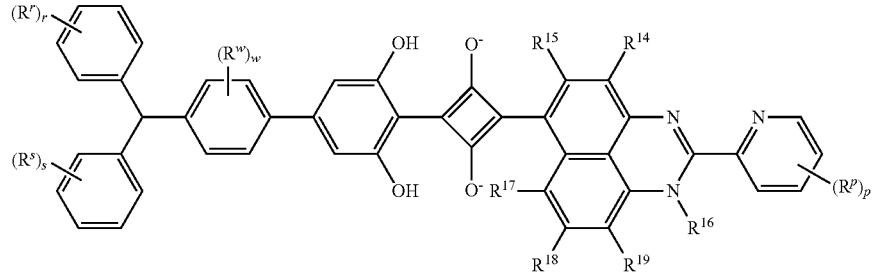

wherein, in Chemical Formula 4-7,
$R^{14}$, $R^{15}$, $R^{16}$, $R^{17}$, $R^{18}$, $R^{19}$, $R^p$, $R^r$, $R^s$, and $R^w$ are independently one compound of the first set of compounds, p and w are independently an integer that is inclusively between 0 to 4, and r and s are independently an integer that is inclusively between 0 to 5,

[Chemical Formula 4-8]

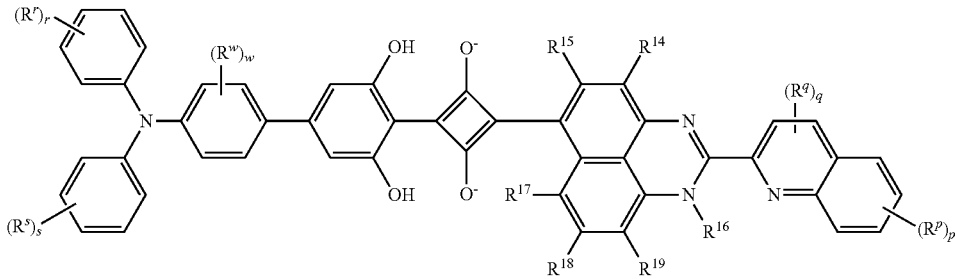

wherein, in Chemical Formula 4-8,
R$^{14}$, R$^{15}$, R$^{16}$, R$^{17}$, R$^{18}$, R$^{19}$, R$^p$, R$^q$, R$^r$, R$^s$, and R$^w$ are independently one compound of the first set of compounds,
p and w are independently an integer that is inclusively between 0 to 4,
q is an integer that is inclusively between 0 to 2, and
r and s are independently an integer that is inclusively between 0 to 5, 14. The infrared cut filter of claim 1, wherein the squarylium compound has a full width at half maximum (FWHM) of at least about 50 nm and less than or equal to about 150 nm based on the squarylium compound being in a thin film state.

15. The infrared cut filter of claim 1, wherein the squarylium compound is associated with a maximum absorption coefficient in an infrared ray (IR) wavelength spectrum of

[Chemical Formula 4-9]

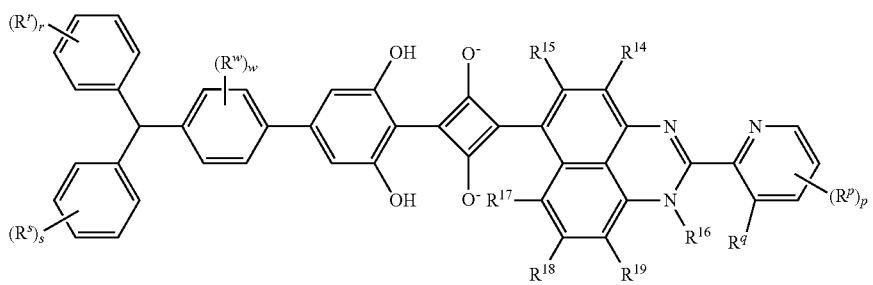

wherein, in Chemical Formula 4-9,
R$^{14}$, R$^{15}$, R$^{16}$, R$^{17}$, R$^{18}$, R$^{19}$, R$^p$, R$^q$, R$^r$, R$^s$ and R$^w$ are independently one compound of the first set of compounds,
p and w are independently an integer that is inclusively between 0 to 4, and
r and s are independently an integer that is inclusively between 0 to 5.

12. The infrared cut filter of claim 1, wherein the squarylium compound is a particular compound represented by Chemical Formula 4-10:

light ($A_{NIR}$) and a maximum absorption coefficient in a visible wavelength spectrum of light ($A_{VIS}$) that satisfy Relationship Equation 1:

$$A_{NIR}/A_{VIS} \geq 8$$ [Relationship Equation 1]

16. The infrared cut filter of claim 1, further comprising an infrared light reflection layer on at least one surface of the infrared cut film.

17. The infrared cut filter of claim 16, wherein the infrared light reflection layer includes an inorganic particulate.

[Chemical Formula 4-10]

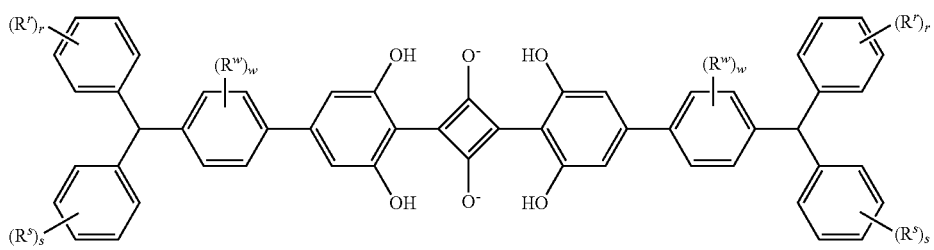

wherein, in Chemical Formula 4-10,
R$^r$, R$^s$, R$^w$, R$^{r'}$, R$^{s'}$, and R$^{w'}$ are independently one compound of the first set of compounds,
w and w' are independently an integer that is inclusively between 0 to 4, and
r, s, r', and s' are independently an integer that is inclusively between 0 to 5.

13. The infrared cut filter of claim 1, wherein the squarylium compound is configured to have a maximum absorption wavelength ($\lambda_{max}$) in a range of greater than or equal to about 700 nm and less than or equal to about 1300 nm based on the squarylium compound being in a thin film state.

18. The infrared cut filter of claim 16, wherein
the infrared light reflection layer is a multi-layered thin film including a first deposition film and a second deposition film, the first deposition film including an inorganic particulate that is at least one particulate of titania (TiO$_2$) and zirconia, the second deposition film including an inorganic particulate that is at least one particulate of silica (SiO$_2$) and alumina.

19. An electronic device comprising the infrared cut filter of claim 1.

* * * * *